(12) United States Patent
Hilbert et al.

(10) Patent No.: US 10,729,159 B2
(45) Date of Patent: Aug. 4, 2020

(54) METHOD OF FEEDING AN ANIMAL

(71) Applicant: CARGILL, INCORPORATED, Wayzata, MN (US)

(72) Inventors: Maxime Hilbert, Chatillon (FR); Irene Van De Linde, Leusden (NL); Yannick Lechevestrier, Betton (FR); Roland Michiel Koedijk, The Hague (NL)

(73) Assignee: CARGILL, INCORPORATED, Wayzata, MN (US)

( * ) Notice: Subject to any disclaimer, the term of this patent is extended or adjusted under 35 U.S.C. 154(b) by 372 days.

(21) Appl. No.: 15/315,184

(22) PCT Filed: May 29, 2015

(86) PCT No.: PCT/US2015/033267
§ 371 (c)(1),
(2) Date: Nov. 30, 2016

(87) PCT Pub. No.: WO2015/184311
PCT Pub. Date: Dec. 3, 2015

(65) Prior Publication Data
US 2017/0119020 A1       May 4, 2017

Related U.S. Application Data

(60) Provisional application No. 62/115,412, filed on Feb. 12, 2015, provisional application No. 62/031,977, filed on Aug. 1, 2014, provisional application No. 62/005,084, filed on May 30, 2014.

(51) Int. Cl.
| | | |
|---|---|---|
| A23K 50/60 | (2016.01) | |
| A23K 10/30 | (2016.01) | |
| A23K 20/174 | (2016.01) | |
| A23K 20/111 | (2016.01) | |
| A23K 50/70 | (2016.01) | |
| A23K 50/75 | (2016.01) | |
| A23K 50/30 | (2016.01) | |
| A61K 31/355 | (2006.01) | |
| A61K 36/53 | (2006.01) | |
| A61K 36/87 | (2006.01) | |
| A61K 36/8962 | (2006.01) | |
| A61K 9/00 | (2006.01) | |

(52) U.S. Cl.
CPC .............. *A23K 50/60* (2016.05); *A23K 10/30* (2016.05); *A23K 20/111* (2016.05); *A23K 20/174* (2016.05); *A23K 50/30* (2016.05); *A23K 50/70* (2016.05); *A23K 50/75* (2016.05); *A61K 9/0056* (2013.01); *A61K 31/355* (2013.01); *A61K 36/53* (2013.01); *A61K 36/87* (2013.01); *A61K 36/8962* (2013.01)

(58) Field of Classification Search
CPC .... A61K 2300/00; A61K 36/53; A61K 36/87; A61K 36/8962; A61K 31/355; A61K 9/0056; A23K 10/30; A23K 20/111; A23K 20/174; A23K 50/30; A23K 50/60; A23K 50/70; A23K 50/75
See application file for complete search history.

(56) References Cited

U.S. PATENT DOCUMENTS

| | | |
|---|---|---|
| 2006/0127530 A1 | 6/2006 | Axelrod |
| 2012/0309829 A1 | 6/2012 | Yamka et al. |

FOREIGN PATENT DOCUMENTS

| | | | |
|---|---|---|---|
| CN | 101385506 A | | 3/2009 |
| CN | 102215700 A | | 10/2011 |
| CN | 102318742 B | * | 4/2013 |
| CN | 103039714 A | | 4/2013 |
| CN | 103349184 A | | 10/2013 |
| CN | 103549150 A | | 2/2014 |
| JP | H08332052 A | | 12/1996 |
| JP | 3233624 B2 | | 9/2001 |
| WO | 2009126976 A1 | | 10/2009 |
| WO | 2010057811 A2 | | 5/2010 |

OTHER PUBLICATIONS

A. Brenes et al: "Effect of Grape Pomace Concentrate and Vitamin E on Digestibility of Polyphenols and Antioxidant Activity in Chickens", Poultry Science, vol. 87, No. 2, Feb. 1, 2008 (Feb. 1, 2008), pp. 307-316, XP055205679, ISSN: 0332-5791, DOI: 10.3382/ps.2007-00297, Sabiqaa Masood; Rao Zahid Abbas; Zafar Iqbal; Muhammad Khalid Mansoor; Zia-Ud-Din Sindhu, Muhammad Anjum Zia; Junaid Ali Khan: Role of Natural Antioxidants for the Control of Coccidiosis in Poultry:, Pakistan Veterinary Journal, Nov. 1, 2013 (Nov. 1, 2013), pp. 401-407, XP055205702.

Demir E et al: "The use of natural feed additives as alternatives for an antibiotic growth promoter in broiler diets", British Poultry Science, Longman Group, GB, vol. 44, No. Suppl. 1, Jan. 1, 2003 (Jan. 1, 2003). pp. S44-S45, XP008104095, ISSN: 0007-1668, DOI: 10.1080/00071660301944.

Kelly E Heim et al: "Flavonoid antioxidants: chemistry, metabolism and structure-activity relationship", J. of Nutr.Biochem., Jan. 1, 2002 (Jan. 1, 2002), pp. 572-584, XP055206323.

International Search Report dated Nov. 19, 2015 for International Application No. PCT/US2015/033267 (6 pages).

Filipovich, E. G., "Vitamins and animal life", Agropromizdat, 1985, p. 67-69.

Liu, Xiaohui , "Research progress on synergism antioxidation mechanism of tea polyphenols and vitamins", Chinese Journal of Tropical Crops., No. 12, Dec. 25, 2012 (pp. 2305-2308)(non-English-language doc.: English title and citations only).

Kocsis I.I.; Petrash, M.G.; Smirnov, S.B., Poultry Farming: a Textbook for University Students Studying in the Specialty of "Livestock", I.I. Kochischa, 2007, pp. 42-47.

(Continued)

*Primary Examiner* — Aaron J Kosar

(57) ABSTRACT

Disclosed is a method of feeding an animal as a part of its feed ration a composition having vitamin E and a polyphenol source. The animals can include an avian or porcine animal.

17 Claims, 6 Drawing Sheets

(56) References Cited

OTHER PUBLICATIONS

Liu, Xiaohui, "Research progress on synergism antioxidation mechanism of tea polyphenols and vitamins", Chinese Journal of Tropical Crops., No. 12, Dec. 25, 2012 (pp. 2305-2308)(non-English-language doc.: Engligh title and citations only).

Zhicheng, Xue, "Effect of Vitamin on Improving Chicken Immune Reaction", China Animal Health, No. 7, Jul. 31, 2005 (p. 37)(non-English-language doc.).

* cited by examiner

METHOD OF FEEDING AN ANIMAL

CROSS-REFERENCE TO RELATED APPLICATIONS

This application is a national phase application of PCT/US2015/033267, filed May 29, 2015, which claims the benefit of U.S. Provisional Patent Application No. 62/005,084, filed May 30, 2014, U.S. Provisional Patent Application No. 62/031,977, filed Aug. 1, 2014 and U.S. Provisional Patent Application No. 62/115,412, filed Feb. 12, 2015, which applications are hereby incorporated by reference herein in their entirety.

TECHNICAL FIELD

The present disclosure relates generally to feeding an animal. Aspects of the disclosure are particularly directed to feeding a monogastric animal a diet including vitamin E with a polyphenol source.

BACKGROUND

Integrated poultry farmers house broiler breeders to produce eggs, incubate the eggs at their own hatchery, and grow out offspring until slaughter. Revenues are largely based on the amount of produced poultry meat minus the costs resulting from feeding the broiler breeders, operating the hatchery, feeding the offspring, and other costs (e.g., poultry housing).

An embryo is dependent for normal growth and development on supply of all required nutrients within the egg. It is known that the supply of nutrients in the egg originates in the maternal nutrition and breeder hen metabolism. When changes can be made in the maternal diet which will influence embryo development and offspring growth, it may be much more cost efficient than changing the offspring diet to improve performance. For example, European Patent Application No. EP2358214 titled "USE OF CANTHAXANTHIN AND/OR 25-OH D3 FOR IMPROVED HATCHABILITY IN POULTRY" assigned to DSM IP Assets B.V. is directed to the use of canthaxanthin for improved hatchability in poultry.

One broiler breeder hen may produce around one hundred broiler chickens per year. Thus, a small improvement in offspring performance, due to a change in breeder nutrition, can have a major impact on the yield resulting from the offspring.

Similarly, the success and profit for animal breeders raising cattle, swine, sheep, and many other animals depends largely upon the ability to produce large numbers of viable offspring. It is, therefore, desirable to increase the birth rate by insuring that a larger percentage of fertilized eggs mature into viable offspring.

SUMMARY

Disclosed is a method of feeding an animal a composition that includes a vitamin E and a polyphenol source. The animals may include monogastric animals such a avian and procine animals. In some embodiments, the feeding of the vitamin E and polyphenol source improves the animal's performance as determined by their reproductive performance and the resultant offspring. In other embodiments, the animal shows improvement in the antioxidant status of the animal as well as its offspring. In some embodiments, the vitamin E can be replaced by a polyphenol source.

In one aspect of the invention is disclosed a method of improving performance in an avian animal, the method comprising:
feeding to the avian animal as a part of its feed ration a composition comprising:
a vitamin E; and
a polyphenol source;
collecting a fertilized egg produced by the avian animal after the start of feeding of the composition to the avian animal;
incubating the fertilized egg until it hatches to provide the offspring; and
growing out the offspring;
wherein performance is improved compared to an avian animal fed a feed ration not containing the composition.

In another aspect of the invention is disclosed a method of improving performance in an avian animal, the method comprising:
feeding to the avian animal as a part of its feed ration a composition comprising:
vitamin E; and
a polyphenol source;
wherein the vitamin E is present in the feed ration at an inclusion level of about 10 ppm to about 200 ppm and the ratio of the vitamin E inclusion level to an inclusion level of the polyphenol source in the composition is about 1:1 vitamin E to polyphenol source,
collecting a fertilized egg produced by the avian animal about 8 weeks after the start of feeding of the composition to the avian animal;
incubating the fertilized egg until it hatches to provide the offspring; and
growing out the offspring,
wherein performance is improved compared to an avian animal fed a feed ration not containing the composition.

In still other aspects of the invention are disclosed a method of improving a porcine animal productivity comprising:
feeding the porcine animal as a part of its feed ration a composition comprising:
vitamin E; and
a polyphenol source, wherein the productivity is improved compared to an animal fed a feed ration not containing the composition.

Other aspects of the invention include a method of improving porcine animal productivity comprising:
feeding to the porcine animal as a part of its feed ration a composition comprising:
vitamin E; and
a polyphenol source;
wherein the vitamin E is present in the feed ration at an inclusion level of about 1 ppm to about 300 ppm and the ratio of the vitamin E inclusion level to an inclusion level of the polyphenol source in the composition is about 1:1 vitamin E to polyphenol source.

DETAILED DESCRIPTION

Figure 1:
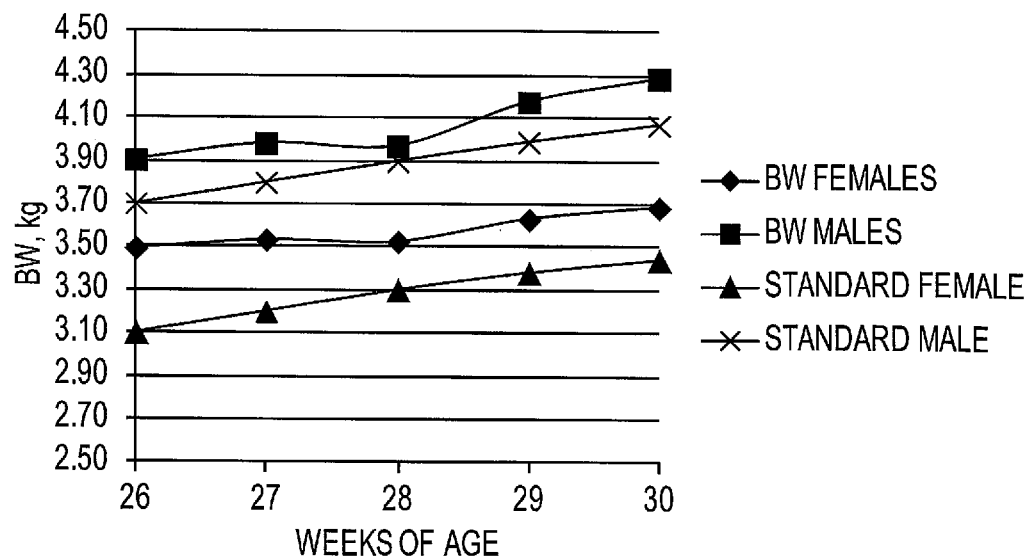
FIG. 1 is a graph of body weight development compared to production standards of Cobb500 FF for Example 1.

Specific details of several embodiments of the disclosure are described below with reference to an animal. Other specific details of several embodiments of the disclosure are described below with reference to a method of improving performance (e.g. offspring performance or animal reproductive performance in an animal (e.g. avian or porcine animal). For example, in one embodiment the method disclosed is a method comprising feeding to the animal as a part of its feed rations a composition comprising vitamin E and a polyphenol source. In some embodiments, the method of feeding the animal its feed ration includes vitamin E present in the feed ration at an inclusion level of about 10 ppm to about 100 ppm and the ratio of the vitamin E inclusion level to an inclusion level of the polyphenol source in the composition is about 1:1 vitamin E to polyphenol source, collecting a fertilized egg produced by the avian animal about five weeks after the start of feeding of the composition to the avian animal, incubating the fertilized egg until it hatches to provide the offspring, and growing out the offspring, wherein offspring performance is improved compared to offspring from an avian animal fed a feed ration not containing the composition.

The term "animals" as used in this disclosure includes monogastric and ruminant animals. As used in this disclosure, the term "monogastric" means any organism having a simple single-chambered stomach. Such monogastric animals include, but are not limited to, porcine, equine, caprine, ovine, avian animals, seafood (aquaculture) animals.

As used in this disclosure, avian monogastric animals include poultry. The term "poultry" as used in this disclosure means domestic fowls, including chickens, turkeys, geese, ducks, ostriches, quails and pheasants raised for the production of meat or eggs. Chickens include "layers" reared for laying eggs, and "broilers" for meat production. Chickens also include "breeders," i.e. birds that have reached the age of sexual maturity and may lay eggs. In some embodiments, the avian animal is selected from the group consisting of a chicken, a turkey, a duck, and a goose. In some embodiments, the avian animal is a chicken.

Chickens suitable for use in embodiments of the present disclosure may belong to one of many possible chicken breeds, including, for example, Ross, Cobb, Isa Brown, Hubbard, Shaver, Atbor Acres, Indian River, Peterson, and Dekalb white. In some embodiments, the chicken may be a Ross chicken.

Porcine monogastric animals include, for example, feeder pigs and breeding pigs, including piglets, sows, gilts, barrows, and boars. As used in this disclosure, the term "ruminant" means any mammal that has a multi-compartment stomach and is associated with digestion by regurgitation and repeated chewing of a bolus or cud. Such ruminant mammals include, but are not limited to, bovine animals such as buffalo, bison, and all cattle, including calves, steers, heifers, cows, and bulls.

While the description is primarily with reference to avian and porcine animals, it is not limited as such and should be understood that the disclosure is applicable to other monogastric and ruminant animals.

Antioxidants, when included in the animal diet, are known to protect cells from damage caused by free radicals and peroxides. There are different types of antioxidants available for feeding an animal (e.g. avian and porcine), including natural dietary antioxidants. Among the natural dietary antioxidants are, for example, vitamins (e.g., E, C), minerals (e.g., Se, Zn), carotenoids, and polyphenols.

Polyphenols are known to help with the regeneration of vitamin E in addition to their free radical scavenging function. Polyphenols useful in embodiments of the present disclosure are commercially available and may be obtained from a variety of sources, including, for example, fruits, vegetables, legumes, nuts, seeds, tea extracts, herbs, spices, and tree barks. Fruits from which polyphenols may be extracted include, for example, apples (red or green), apricots, currants (black or red), blackberries, blueberries, cherries (sweet or sour), chokeberries, cranberries, dates, elderberries, gooseberries, grapes (red or purple) kiwis, lemons, lingonberries, limes, mangoes, marionberries, nectarines, olives, oranges (e.g., navel, tangelos, tangerines, blood), peaches, pears, plums, pomegranates, quinces, raspberries, rhubarb, strawberries, and tomatoes. Vegetables from which polyphenols may be extracted include, for example, artichokes, broccoli, celery, corn, eggplant, fennel, garlic, greens (e.g., kale and turnip), kohlrabi, leeks, lovage, onions (red and yellow), parsnips, peppers, spinach, red cabbage, rutabagas, scallions, shallots, sweet potatoes, and watercress. Legumes, nuts, seeds from which polyphenols may be extracted include, for example, seeds of any of the fruits listed above (e.g., grape seeds), almonds, cashews, chick peas, beans (e.g., black beans, red kidney beans, pinto beans, black-eyed peas), English peas, fava beans, flax seeds, green peas, hazelnuts, lentils, pecans, peanuts, pistachios, pumpkin seeds, snap beans, sunflower seeds, and walnuts. Teas from which polyphenols may be extracted include, for example, green tea, black tea, oolong tea, Earl Gray tea, Ceylon tea, and Darjeeling tea. Herbs, and spices from which polyphenols may be extracted include, for example, basil chives capers (red and green), cinnamon, curry, dill weed, horseradish, oregano, parsley, rosemary, sage, tarragon, and thyme. In some embodiments, the polyphenol source comprises at least one of onion extract, grape seed extract, and rosemary extract. Tree barks from which polyphenols may be extracted include, for example, arjuna bark, aspen bark, birch bark, conifer bark (e.g., cedar, cypress, fir, larch, pine, spruce, yew), eucalyptus bark, and maple bark.

In some embodiments, the polyphenol source may include onion extract, grape seed extract, and rosemary extract.

A polyphenol source suitable for use in embodiments of the present disclosure is available commercially under the trade name PROVIOX 50, available from Cargill, Incorporated, Wayzata, Minn., USA. The formulation of PROVIOX 50 includes a blend of polyphenol grape seed and skin extracts, onion extracts and rosemary extracts. PROVIOX 50 is a standardized product for its total polyphenol content. PROVIOX 50 contains source of compounds with antioxidant properties and can replace or supplement Vitamin E 50, which can save costs and support animal anti-oxidant status and performance. The substitution rate depends on dietary vitamin E level. In some embodiments, vitamin E levels above the National Research Council (NRC) requirements (refer to Tables A & B for Swine and Poultry) can be substituted or replaced by a vitamin E equivalent such as a polyphenol. In some embodiments, the polyphenol is PROVIOX 50.

One aspect of the present disclosure is directed to feeding an animal, as a part of its feed ration, a composition comprising vitamin E and a polyphenol source such as PROVIOX 50.

In some embodiments, for a feed for an avian animal, the vitamin E is present in the feed ration at an inclusion level of about 10 ppm to about 200 ppm, about 20 ppm to about 100 ppm, about 30 ppm to about 90 ppm, or about 35 ppm to about 85 ppm.

In some embodiments for a feed for a porcine animal, the vitamin E is present in the feed ration at an inclusion level of about 1 ppm to about 300 ppm, about 20 ppm to about 250 ppm, about 30 ppm to about 200 ppm, or about 35 ppm to about 150 ppm.

In some embodiments, the ratio of the vitamin E inclusion level to an inclusion level of the polyphenol source in the composition is about 1:1 vitamin E to polyphenol source. Vitamin E in animal diet is typically at least equal to minimum National Research Council (NRC) requirements (refer to below Tables A & B for Swine and Poultry).

In some embodiments, vitamin E levels above the minimum NRC levels can be replaced, substituted with a vitamin E equivalent such as polyphenol. In some embodiments, the polyphenol is PROVIOX 50. While the composition is discussed in relation to a 1:1 ratio of Vitamin E to a vitamin E equivalent, it should be understood that the application contemplates various other ratios of Vitamin E to Vitamin E equivalent such as a polyphenol. In some embodiments, the ratio of the vitamin E to polyphenol source can range from about 1:2 to about 1:5 such as 1:2, 1:3, 1:4 or 1:5.

TABLE A

| Swine (Vit. E) | Minimum NRC Requirement (IU) |
|---|---|
| Piglets 3-5 kg | 20 IU/KG |
| Piglets 5-10 kg | 20 IU/KG |
| Piglets 10-20 kg | 14 IU/KG |
| Pigs 20-50 kg | 14 IU/KG |
| Pigs 50-80 kg | 14 IU/KG |
| Pigs 80-12 kg | 14 IU/KG |
| Sow gestation | 55 IU/KG |
| Sow lactation | 55 IU/KG |

TABLE B

| Poultry (Vit. E) | Minimum NRC Requirement (IU) |
|---|---|
| Broiler 0-7 d | 19 |
| Broiler 0-18 d | 18 |
| Broiler 19-35 d | 15 |
| Broiler 36-42 d | 13 |
| Layers 0-6 wk | 15 |
| Layers 7-16 wk | 12 |
| Layer >17 wk | 10 |

Inclusion rate of the polyphenol source in complete feed varies from 1 ppm to 300 ppm (10 g to 300 g of the polyphenol source per ton of complete feed). For example, 10 ppm to 100 ppm, also for example, 20 ppm to 95 ppm, also for example, 30 ppm to 90 ppm, also for example, 35 ppm to 85 ppm.

In some embodiments, the avian animal is fed the composition comprising vitamin E and a polyphenol source to improve avian productivity. Avian productivity includes breeder performance, offspring performance and antioxidant status.

In some embodiments, the avian animal is fed a composition that includes vitamin E and a polyphenol source for at least about 5 weeks, at least about 6 weeks, at least about 7 weeks, at least about 8 weeks before a fertilized egg is collected for incubation. In one embodiment, the fertilized egg is collected about 6 weeks to about 10 weeks after the start of feeding of the composition to the avian animal. In other embodiments, the fertilized egg is collected about 8 weeks after the start of feeding the composition.

Methods of preparing feed for avian animals are known in the art and are described, for example, in Feeding Poultry: The Classic Guide to Poultry Nutrition for Chickens, Turkeys, Ducks, Geese, Gamebirds, and Pigeons, G. F. Heauser, Norton Creek Press, 2003 and Commercial Poultry Nutrition, 3rd Edition, Leeson et al., University Books, 2005.

Feed rations for avian animals may include a variety of ingredients, such as, for example, corn, wheat, soybean meal, fats and oils (e.g., soya oil), limestone, monocalcium phosphate, sodium bicarbonate, sodium chloride, L-lysine HCl, DL-methionine, L-threonine, and a premix starter or a premix grower including, for example, vitamin A (retinyl-acetate), vitamin D3 (cholecalciferol), vitamin E (DL-α-tocopherol), vitamin K3 (menadione), vitamin B1 (thiamine), vitamin B2 (riboflavin), vitamin B6 (pyridoxine-HCL), vitamin B12 (cyanocobalamine), niacin, D-pantothenic acid, choline chloride, folic acid, biotin, KI, $FeSO_4.H_2O$; $CuSO_4.5H_2O$, MnO, $ZnSO_4.H_2O$, and $Na_2SeO_3$.

In some embodiments, the avian animal may be fed the composition comprising vitamin E and a polyphenol source starting at hatching, starting at 1 week old from hatching, starting at 2 weeks old, starting at 3 weeks old, starting at 4 weeks old, starting at 5 weeks old, starting at 6 weeks old, starting at 7 weeks old, starting at 8 weeks old, starting at 9 weeks old, starting at 10 weeks old, starting at 11 weeks old, starting at 12 weeks old, starting at 13 weeks old, starting at 14 weeks old, starting at 15 weeks old, starting at 16 weeks old, starting at 17 weeks old, starting at 18 weeks old, starting at 19 weeks old, starting at 20 weeks old, starting at 21 weeks old, starting at 22 weeks old, starting at 23 weeks old, starting at 24 weeks old, starting at 25 weeks old, starting at 26 weeks old, starting at 27 weeks old, starting at 28 weeks old, starting at 29 weeks old, or starting at about 30 weeks old from hatching. In some embodiments, the avian animal may be fed the composition comprising vitamin E and a polyphenol source throughout its entire life cycle.

Offspring of a fertilized egg produced by the avian animal fed the composition comprising vitamin E and a polyphenol source may demonstrate improved performance compared to offspring from an avian animal fed a feed ration not containing the composition which may be measured according to methods known to those of ordinary skill in the relevant arts.

In some embodiments, improved offspring performance is at least one of improved offspring weight at hatch, improved offspring final bodyweight, improved offspring average daily gain, improved offspring feed conversion ratio, improved offspring feed intake and antioxidant status. Antioxidant status may be determined by any known methods including measuring the superoxide dismutase or glutathione peroxidase levels and vitamin A and vitamin E levels.

In some embodiments, the improved avian offspring performance is at least 1% higher, at least 1.5% higher, at least 2% higher, at least 2.5% higher, at least 3% higher, at least 3.5% higher, at least 4% higher, at least 4.5% higher, at least 5% higher, at least 5.5% higher, at least 6% higher, at least 6.5% higher, at least 7% higher, at least 7.5% higher, at least 8% higher, at least 8.5% higher, at least 9% higher, at least 9.5% higher, or at least 10% higher compared to offspring from an avian animal fed a feed ration not containing the composition. In other embodiments, the avian offspring performance fed the disclosed composition including a polyphenol source is similar to an avian animal fed vitamin E.

In some embodiments, breeder performance is improved compared to breeder fed a diet without vitamin E. In some embodiments, feeding of the composition comprising vitamin E and a polyphenol source may result in similar or better breeder performance compared to breeders fed only vitamin E. Breeder performance includes, for example, hatchability of fertile eggs and the breakage of the egg shells. In some embodiments, the hatchability improved. In other embodiments, the breakage of eggshells was reduced. In still other embodiments, the antioxidant status is improved.

A similar method may be directed to feeding a porcine animal, as further described in the Examples. In some embodiments, the porcine animal is fed the composition comprising vitamin E and a polyphenol source to improve porcine productivity. Porcine productivity includes reproductive performance, litter performance and antioxidant status.

Reproductive performance includes, for example, the farrowing rate, actual parity, mating, farrowing and weaning and other parameters as measured in Table 44. Litter performance includes, for example, number of porcine animals born alive, weak or born mummified, the litter weight (e.g. at weaning or after lactation) and other parameters as measured in Table 45. Antioxidant status includes determining the activity of superoxide dismutase, glutathione peroxidase and determining the content of vitamin A and E.

The feeding of the composition comprising vitamin E and a polyphenol source may result in improved porcine productivity as porcine fed a diet without vitamin E. In some embodiments, feeding of the composition comprising vitamin E and a polyphenol source may result in similar or better porcine productivity compared to porcine fed only vitamin E.

The feeding of the composition may be administered daily through the initial gestation period up to lactation and farrowing. In some embodiments, feeding may start on the first day of breeding and even during the period 120 days before breeding (prebreeding). The feed fed during the prebreeding period and during breeding are well known in the art. The concentration of the composition comprising vitamin E and polyphenol may be substantially the same during prebreeding as those fed during the gestation period.

A base diet may be any typical swine diet known in the art, including those specially formulated for gestating or lactating swine. For example, a diet will include a selection of the ingredients described in Table 42 of the application. Extensive guidance in formulating diets for the feeding of swine can be found in "Nutrient Requirements of Swine", Nutrient Requirements of Domestic Animals, Number 3, 9th rev. ed. (National Academy of Science, Washington, D.C.: 1988).

A feed schedule and feed rates used may be any standard schedule and rate used in the art. Generally, gestating swine are fed from about 4 to about 6 pounds of the diet per day, and from about 4 to about 5 pounds per day. Lactating swine are generally fed from about 9 to about 15 pounds of the diet per day, and from about 13 to about 14 pounds per day. Generally, the feed is administered from 1 to 2 times a day for gestating swine and from 1 to 2 and up to 4 times a day for lactating swine.

In some embodiments for a feed for a porcine animal, the vitamin E is present in the feed ration at an inclusion level of about 1 ppm to about 300 ppm, about 20 ppm to about 250 ppm, about 30 ppm to about 200 ppm, or about 35 ppm to about 150 ppm.

EXAMPLES

Aspects of certain methods in accordance with aspects of the invention are illustrated in the following Examples. Examples 1-9 are directed to feeding an avian animal, and Example 10 is directed to feeding a porcine animal.

Example 1—Partial Replacement of Vitamin E by PROVIOX 50 in Broiler Breeder Diets Two different breeder diets (Table 1) were tested in a randomized block design. Breeders received a standard control diet or a diet where 50% of the vitamin E was replaced by PROVIOX 50. The two diets were randomly distributed into six cages, resulting in three replicates per treatment with 28, 29, or 30 females and three or four males per replicate.

TABLE 1

Broiler Breeder Diets

| | | Inclusion Level (ppm) | | | Vit E Equivalence In Diet (ppm) | |
|---|---|---|---|---|---|---|
| | | Female Diet | | | | |
| Nr. | Treatment | VitE 50 | PROVIOX 50 | VitE 50 | PROVIOX 50 | Male Diet Female | Male |
| 1 | Control | 160 | — | 120 | — | 80 | 60 |
| 2 | PROVIOX | 80 | 80 | 60 | 60 | 80 | 60 |

The experimental period lasted four weeks; the breeders received a lay start diet during the entire period according to the experimental design. Feed and water were restricted. Feed amount depended on body weight development. The feeding schedule of Example 1 is given in Table 2. Water was provided for two hours a day, crops were checked regularly to ensure the correct amount of water was provided.

TABLE 2

Feeding Schedule
Feed level, g/bird/day

| | Female | Male |
|---|---|---|
| 26-27 weeks of age | 154 | 100.7 |
| 27-28 weeks of age | 156 | 105 |

TABLE 2-continued

Feeding Schedule
Feed level, g/bird/day

|  | Female | Male |
|---|---|---|
| 28-29 weeks of age | 158 | 110.7 |
| 29-30 weeks of age | 160 | 115 |

A total of 24 male and 173 female Cobb 500FF 20-week-breeder chickens were procured. The males and females were randomly assigned to six floor pens (four males per pen, 29 females in pens 1-3, 30 females in pen 4, and 28 females in pens 5 and 6). During the pre-trial period, all breeders received the control diet.

Throughout the trial, breeders were housed in broiler breeder floor pens (2.60×2.40 in) on litter (flax). Each pen was equipped with two bell drinkers adjustable in height. The feed for the females was supplied via two feeder bowls on the raised slatted floor. The feed for the males was supplied via a feeder trough on the other side of the pen.

Day length was set at 14 hours a day until peak production was reached (70%; day 15). After peak production was achieved, day length was set to 15 hours a day. Temperature and ventilation were computer controlled. The temperature was set at 20° C. for the entire experimental period.

Diets were produced by Research Diet Services, Wijk bij Duurstede, The Netherlands. All diets were produced separately, using one basal diet batch for the female diets and one basal diet batch for the male diets. Diets were produced as a mash.

In advance of diet formulation preparation, batches of soybean meal and coarsely ground maize and wheat were reserved and wet chemically analyzed for crude protein, calcium, and phosphorus. In addition, soybean meal was analyzed for potassium. Near-infrared spectroscopy ("NIRS"), using a Bruker MPA, ISO 12099 spectrometer available from Bruker Optik GmbH, Ettlingen, Germany, was used to predict crude ash, crude fat, crude fiber, moisture, and to crosscheck crude protein. Formulation of the diets was based on the analyzed nutrient content of the reserved ingredients.

A basal diet (corn—soybean meal—wheat and wheat middlings) was formulated based on Provimi B.V. nutrient recommendations for broiler breeders. A broiler breeder premix was used without added vitamin E and a specific antioxidant product. Different male and female diets were produced, though using the same experimental design. This was done to be able to feed the males according to their nutritional needs (lower for crude protein, energy, and calcium, and different premix requirements) without compromising the experimental design. The composition of the experimental diets is given in Table 3. Analyses of the experimental diets are shown in Table 4.

TABLE 3

Ingredient and Nutritional Composition of the Experimental Diets

| Feedcode | LT1202-1 | LT1202-2 | LT1202-3 | LT1202-4 |
|---|---|---|---|---|
| Treatment | 1 | 2 | 1 | 2 |
| Sex | Female | Female | Male | Male |
| Diet Form | Mash | Mash | Mash | Mash |
| Ingredient Composition (%) | | | | |
| Corn (A5043) | 44.5 | 44.5 | 30.0 | 30.0 |
| Wheat (A4976) | 20.0 | 20.0 | 26.7 | 26.7 |

TABLE 3-continued

Ingredient and Nutritional Composition of the Experimental Diets

| Feedcode | LT1202-1 | LT1202-2 | LT1202-3 | LT1202-4 |
|---|---|---|---|---|
| Soybean Meal (A4971) | 16.5 | 16.5 | 13.2 | 13.2 |
| Wheat Middlings | 7.5 | 7.5 | 25.0 | 25.0 |
| Limestone Coarse | 5.0 | 5.0 | 1.1 | 1.1 |
| Limestone Fne | 2.5 | 2.5 | 0.6 | 0.6 |
| Monocalcium Phosphate | 1.4 | 1.4 | 1.0 | 1.0 |
| Soya Oil | 1.0 | 1.0 | 1.0 | 1.0 |
| Premix Female[1] (1%) | 1.0 | 1.0 | — | — |
| Premix Male[2] (1%) | — | — | 1.0 | 1.0 |
| Salt | 0.12 | 0.12 | 0.26 | 0.26 |
| Na-Bicarbonate | 0.26 | 0.26 | 0.07 | .017 |
| DL-Methionine | 0.148 | 0.148 | 0.045 | 0.045 |
| L-Lysine HCL | 0.109 | 0.109 | — | — |
| Vitamin E 50% | 0.016 | 0.016 | 0.010 | 0.005 |
| PROVIOX 50 | — | — | — | 0.005 |
| Nutritional Composition (%) - Based on Provimi Nutrient Code System | | | | |
| 1120 Crude Protein | 14.9 | 14.9 | 15.4 | 15.4 |
| 1130 Crude Fat | 3.43 | 3.43 | 3.53 | 3.53 |
| 2250 Crude Fibre | 2.65 | 2.65 | 3.84 | 3.84 |
| 1150 Ash | 11.3 | 11.3 | 5.9 | 5.9 |
| 1110 Dry Matter | 88.4 | 88.4 | 87.4 | 87.4 |
| 1511 Calcium | 3.15 | 3.15 | 0.90 | 0.90 |
| 1513 Phosphorus P | 0.66 | 0.66 | 0.72 | 0.72 |
| 3312 Av. P | 0.42 | 0.42 | 0.35 | 0.35 |
| 3311 Dig. P Layers | 0.39 | 0.39 | 0.35 | 0.35 |
| 1521 Sodium | 0.16 | 0.16 | 0.15 | 0.15 |
| 1522 Potassium | 0.67 | 0.67 | 0.82 | 0.82 |
| 1523 Chloride | 0.14 | 0.14 | 0.20 | 0.20 |
| 1530 dEB | 200 | 200 | 218 | 218 |
| 3110 ME Poultry | 2713 | 2713 | 2686 | 2686 |
| 3112 ME Poultry (FS-R) | 2743 | 2743 | 2710 | 2710 |
| 3120 ME Layer | 2750 | 2750 | 2723 | 2723 |
| 1210 LYS | 0.759 | 0.759 | 0.673 | 0.673 |
| 1211 MET | 0.383 | 0.383 | 0.288 | 0.288 |
| 1213 SAA | 0.657 | 0.657 | 0.583 | 0.583 |
| 1214 THR | 0.534 | 0.534 | 0.539 | 0.539 |
| 1215 TRP | 0.170 | 0.170 | 0.187 | 0.187 |
| 1216 ILE | 0.609 | 0.609 | 0.602 | 0.602 |
| 1219 ARG | 0.903 | 0.903 | 0.948 | 0.948 |
| 1218 VAL | 0.690 | 0.690 | 0.713 | 0.713 |
| 3200 AFD LYSp | 0.630 | 0.630 | 0.540 | 0.540 |
| 03201 AFD METp | 0.346 | 0.346 | 0.247 | 0.247 |
| 3203 AFD SAAp | 0.560 | 0.560 | 0.480 | 0.480 |
| 3204 AFD THRp | 0.422 | 0.422 | 0.419 | 0.419 |
| 3205 AFD TRPp | 0.145 | 0.145 | 0.157 | 0.157 |
| 3206 AFD ILEp | 0.516 | 0.516 | 0.503 | 0.503 |
| 3209 AFD ARGp | 0.791 | 0.791 | 0.827 | 0.827 |
| 3208 AFD VALp | 0.564 | 0.564 | 0.577 | 0.577 |
| 3240 TFD LYSp | 0.671 | 0.671 | 0.572 | 0.572 |
| 3241 TFD METp | 0.358 | 0.358 | 0.258 | 0.258 |
| 3243 TFD SAAp | 0.590 | 0.590 | 0.503 | 0.503 |
| 3244 TFD THRp | 0.456 | 0.456 | 0.450 | 0.450 |
| 3245 TFD TRPp | 0.148 | 0.148 | 0.160 | 0.160 |
| 3246 TFD ILEp | 0.546 | 0.546 | 0.531 | 0.531 |
| 3249 TFD ARGp | 0.825 | 0.825 | 0.860 | 0.860 |
| 3248 TFD VALp | 0.612 | 0.612 | 0.617 | 0.617 |
| 1327 C18:2 | 1.61 | 1.61 | 1.61 | 1.61 |
| Vitamin E Equivalence (IU) | 80.0 | 80.0 | 50.0 | 50.0 |

[1]Supplied per kg diet: riboflavin, 9.0 mg; niacinamide, 40 mg; D-pantothenic acid, 12 mg; choline chloride, 600 mg; DL-α-tocopherol, - IU; menadione, 2.5 mg; retinyl-acetate, 12500 IU; cholecalciferol, 2500 IU; biotin, 150 µg; folic acid, 1.5 mg; Thiamine, 2.0 mg; pyridoxine-HCl, 4.5 mg; cyanocobalamine, 30 µg; FeSO$_4$•H$_2$O, 147 mg; MnO$_2$, 135 mg; CuSO$_4$•5H$_2$O, 40 mg; ZnSo$_4$•H$_2$O, 275 mg; Se(org), 0.88 mg; KJ, 2.6 mg; antioxidant (Oxytrap PXN), - mg.
[2]Supplied per kg diet: riboflavin, 7.5 mg; niacinamide, 30 mg; D-pantothenic acid, 9 mg; choline chloride, 500 mg; DL-α-tocopherol, - IU; menadione, 3.5 mg; retinyl-acetate, 10000 IU; cholecalciferol, 2000 IU; biotin, 100 µg; folic acid, 1.0 mg; Thiamine, 2.0 mg; pyridoxine-HCl, 3.0 mg; cyanocobalamine, 25 µg; FeSO$_4$•H$_2$O, 147 mg; MnO$_2$, 106 mg; CuSO$_4$•5H$_2$O, 40 mg; ZnSo$_4$•H$_2$O, 206 mg; Se(org), 0.88 mg; KJ, 1.9 mg; antioxidant (Oxytrap PXN), - mg.

TABLE 4

Analyzed Nutritional Composition of the Experimental Diets

|  | Females | | Males | |
| --- | --- | --- | --- | --- |
| Diet Code | LT1202-1 | LT202-2 | LT01202-3 | LT1202-4 |
| Calculated Nutrients, % | | | | |
| Crude Protein | 14.9 | 14.9 | 15.4 | 15.4 |
| Crude Fat | 3.4 | 3.4 | 3.5 | 3.5 |
| Crude Fibre | 2.7 | 2.7 | 3.8 | 3.8 |
| Dry Matter | 88.4 | 88.4 | 87.4 | 87.4 |
| Ca | 3.15 | 3.15 | 0.90 | 0.90 |
| P | 0.66 | 0.66 | 0.72 | 0.72 |
| Analysed Nutrients | | | | |
| Crude Protein | 15.3 | 16.1 | 16.6 | 15.8 |
| Crude Protein (NIRS) | 15.8 | 16.0 | 16.3 | 15.7 |
| Crude Fat (NIRS) | 3.2 | 3.2 | 3.9 | 3.7 |
| Crude Fibre (NIRS) | 2.8 | 2.6 | 3.9 | 3.9 |
| Moisture (NIRS) | 11.4 | 11.1 | 11.1 | 11.5 |
| Dry Matter | 88.6 | 88.9 | 88.9 | 88.5 |
| Ca | 3.07 | 3.08 | 1.13* | 0.87 |
| P | 0.65 | 0.66 | 0.70 | 0.64* |
| % of expected | | | | |
| Crude Protein | 103 | 104 | 105 | 103 |
| Crude Fat | 93 | 93 | 110 | 105 |
| Crude Fibre | 106 | 98 | 101 | 101 |
| Dry Matter | 100 | 101 | 102 | 101 |
| Ca | 98 | 98 | 126 | 97 |
| P | 99 | 100 | 98 | 89 |

*Duplicate Analysis

Individual bird weights were recorded weekly from the start of the experiment. Feed amount provided was recorded on a daily basis. Egg production and egg quality data were recorded on a daily basis. Laying % was calculated as number of eggs produced per pen divided by the number of bird days of the experimental period. Egg mass production per pen per week was calculated as laying % (including second-class eggs) times average egg weight of the pen. Average egg weight was determined per pen once a week. Second-class eggs were divided into dirty eggs, broken eggs, shell-less eggs, double-yolk eggs, floor eggs and remaining second-class eggs. Mortality was checked every day; dead animals were not replaced during the experimental period.

For comparison of the different treatments all parameters were subjected to the mixed model procedure using SAS Version 9.2, 2008 (SAS Institute Inc., Cary, N.C., USA) according to the following statistical model:

$$Y_{ij} = \mu + \alpha_i + \varepsilon_{ij}$$

Where:
$Y_{ij}$ = a specific trait per experimental unit (pen)
$\mu$ = overall mean for the specific trait
$\alpha_i$ = fixed treatment effect (i=1 or 2)
$\varepsilon_{ij}$ = error term Differences between means were assumed to be significant based on the probability of P<0.05 (Student t-test for mean separation) unless another probability value is stated.

Nutritional composition of the diets was reasonably in line with the expected values (Table 4) except for the calcium level in the male control diet and the phosphorus level in the male PROVIOX 50 diet (based on duplicate analysis). However, because one diet batch was used to produce both diets, and the same reserved and analyzed ingredients were used as for the female diets, it is expected that these findings relate to errors in the analysis or sampling because the diets were fed as mash.

Figure 2:
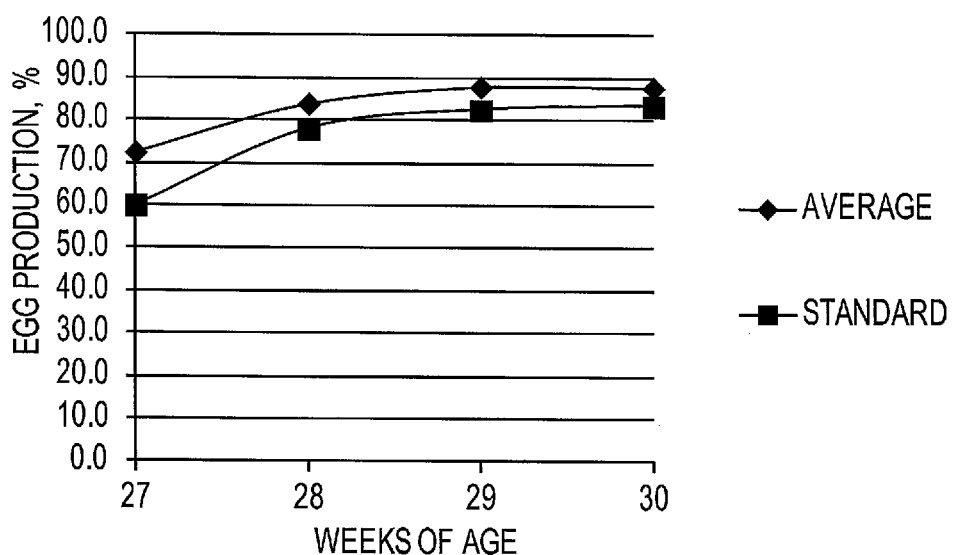
FIG. 2 is a graph of egg production compared to production standards of Cobb500 FF for Example 1.
Figure 3:
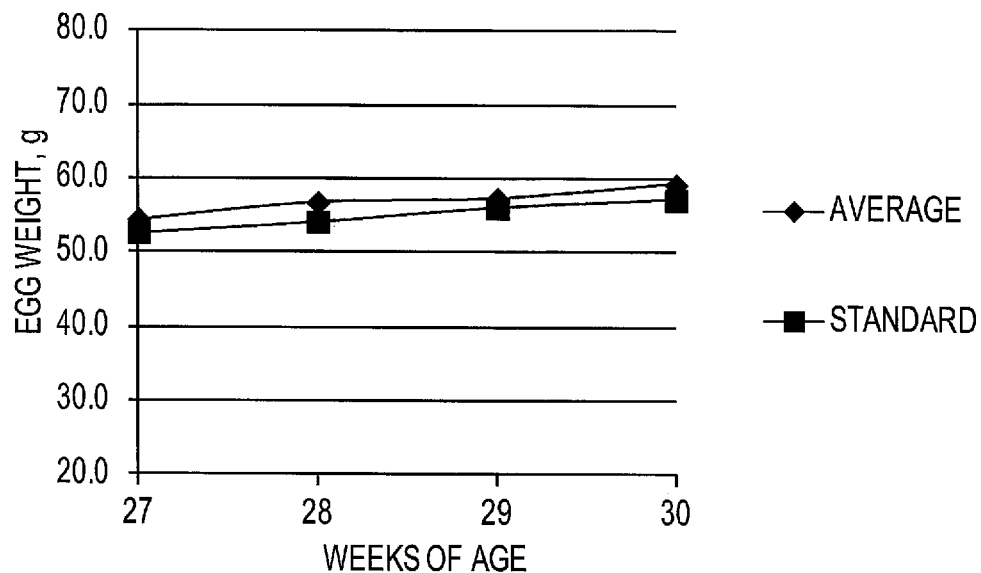
FIG. 3 is a graph of egg weight compared to production standards of Cobb500 FF for Example 1.

Observed health status of the birds was good throughout the experiment. Mortality, including culling, reached 1.5% (Table 5), which is in line with practical levels (1.6% from 26 to 30 weeks of age). Technical performance of the birds was in line with breeder standards of Cobb500 FF (FIGS. 1-3 and Table 6).

TABLE 5

Mortality and Culling Calculated as a Percentage of Animals at Start of the Trial (total 195)

| Period | Mortality | Culling | Total |
| --- | --- | --- | --- |
| d 26-30 | 0.5 | 1 | 1.5 |

TABLE 6

Technical Results of Breeders Fed the Control Diet or the PROVIOX 50 Diet where Half of the Vitamin E Level was Replaced by PROVIOX 50 (26 through 30 weeks of age).

|  | Control | PROVIOX | SEM | P-Value |
| --- | --- | --- | --- | --- |
| Laying Percentage % | 83.6 | 82.4 | 1.654 | 0.631 |
| First Class Eggs % | 77.9 | 77.0 | 1.655 | 0.709 |
| Second Choice Eggs | | | | |
| Broken Eggs % | 1.6 | 1.2 | 0.408 | 0.550 |
| Dirty Eggs % | 0.7 | 0.8 | 0.110 | 0.615 |
| Shell Less Eggs % | 0.1 | 0.0 | 0.060 | 0.375 |
| Double Yolk Eggs % | 1.3 | 1.9 | 0.409 | 0.355 |
| Floor Eggs % | 1.4 | 0.9 | 0.291 | 0.283 |
| Remainder % | 0.5 | 0.5 | 0.142 | 0.976 |
| Egg Weight, g | 56.4 | 55.5 | 0.581 | 0.328 |
| Egg Mass, g/hen/day | 47.1 | 45.7 | 1.039 | 0.382 |
| BW 26 wk Females, kg | 3.50 | 3.49 | 0.026 | 0.787 |
| BW 30 wk Females, kg | 3.68 | 3.69 | 0.035 | 0.756 |
| BW 26 wk Males, kg | 3.91 | 3.90 | 0.107 | 0.939 |
| BW 30 wk Males, kg | 4.19 | 4.38 | 0.111 | 0.273 |

Referring to FIGS. 1-3 and Table 6, no significant differences were found between the two treatment groups on laying performance of the broiler breeders. This might be related to the number of replicates per treatment. Some variation was expected because the breeders were in the starting phase of egg production.

No significant differences were found between the two treatments, indicating that breeder performance was not affected when vitamin E level was 50% replaced by PROVIOX 50.

Example 2—Chicken Production from Eggs of Example 1

For a period of nine days, eggs were collected from the broiler breeder flock of Example 1. The eggs were stored based on breeder pen and storage day. Eggs were allocated to twelve trays and nine blocks, with each block representing a storage day. At E17, all eggs were candled and at E18, eggs were transferred from the incubator setters to hatcher baskets.

A total of 540 eggs (all eggs produced during nine days) derived from 28-29 week broiler breeders of Example 1 were collected and stored in an incubator at 18° C. (64.4° F.) and a relative humidity of 75%. At the start of the incubation period, the eggs were weighed and allocated into blocks, each block representing a storage day. Each block consisted of twelve experimental units, with each experimental unit indicating a group of ten eggs. Only intact eggs were included; cracked, dirty, or eggs with deformed shells were excluded from the experiment.

The eggs were placed in a NatureForm NMC 2340 Incubator with automatic control of temperature and relative humidity. From E0 until E18, the eggs were placed in setter trolleys, which consist of two shelves with a capacity for thirteen trays each. Each tray has three flats of thirty eggs. During this period, the incubator start temperature was set to 37.5° C. and relative humidity to 54%. The temperature was set based on a temperature profile starting at 37.5° C. at E0 and gradually decreasing from E12 to E18 from 37.5° C. to 36.7° C.

After the setter period (E0-E18), eggs were transferred to baskets in the hatchers based on the blocking structure in the setter. The eggs were placed into subdivisions of a hatching crate, per replicate, and following tray order per block. Each hatcher trolley has twelve baskets with a capacity for 180 eggs each. During this period, the incubator temperature was set to 36.7° C. and relative humidity to 70%.

Egg weights were recorded per experimental unit at E0. At hatch (E21) the number of dead chickens, dead embryos and pipped eggs (internal and external) were recorded. Remaining non-hatched eggs were opened to determine age and cause of death. The number of hatched chickens was recorded per replicate, as well as average chick weight. Sex was determined by cloaca sexing, performed by a professional chicken-sexer. Hatchability was calculated as percentage of total and of fertile eggs (eggs which contained living embryos after E17). A total of 102 male chickens per treatment were randomly selected for Example 3 based on broiler breeder pen. Only chickens with an average body weight, completely dry, showing active movement and with a good navel score were selected. Two male chickens from each experimental unit (total of 108 per treatment) were selected for dissection. Sample chickens were individually weighed and killed by cervical dislocation to measure remaining yolk-sac weights, yolk-free body mass ("YFBM"), chick length, and shank length of both shanks. Relative asymmetry was calculated according to the following formula:

$$RA = (|L-R|/[(L+R)/2]) \times 100.$$

where:
L=left shank length
R=right shank length.

For comparison of the different treatments all parameters were subjected to the mixed model procedure using SAS Version 9.2, 2008 (SAS Institute Inc., Cary, N.C., USA) according to the following statistical model:

$$Y_{ijkl} = \mu + \alpha_i + b_j + c_k + ac_{ik} + \varepsilon_{ijkl}$$

where:
$Y_{ijkl}$=a specific trait
$\mu$=overall mean for the specific trait
$\alpha_i$=fixed effect of broiler breeder treatment (i=1 or 2)
$b_j$=random effect of block/storage day (j=1-9)
$c_k$=random effect of whole plot block (k=1, 2 or 3)
$ac_{ik}$=random interaction effect of whole plot block and treatment
$\varepsilon_{ijkl}$=error term The interaction factor whole plot block with treatment was included in the model to correct for the number of experimental units of the broiler breeder treatment used. Due to the design of the trial, storage day effect was completely confounded with block (location in incubator) effect. The parameters fertility, hatchability of total, and hatchability of fertile were considered as binomial data. Differences between means were assumed to be significant based on the probability of P<0.05 (Student t-test for mean separation) unless another probability value is stated.

Average egg weight at the start of the trial was 57.9 gram per egg. Overall fertility (94%) was in line with the breeder guideline of Cobb and hatchability (91%) was above average according to the breeder guideline (respectively 95 and 85% for breeders of 28-29 weeks of age). The higher hatchability results compared to the guideline might result from the smaller incubators used compared to incubators used in practice, resulting in an optimized brooding process and therefore less embryonic mortality.

Fertility and hatchability were not significantly influenced by the broiler breeder treatments (Table 7). However, numerically the eggs produced by the broiler breeders fed the PROVIOX 50 treatment had a 4.6% higher hatchability of total which was mainly related to an increase in fertility of 3.6%.

TABLE 7

Broiler breeder treatment effects on hatchability, fertility, chick weight and relative chick weight.

|  | Vit E 50% | PROVIOX | SEM | p-Value |
| --- | --- | --- | --- | --- |
| n | 3 | 3 | — | — |
| Hatchability of total, % | 88.6 | 92.7 | — | 0.2546 |
| Hatchability of fertile, % | 95.6 | 96.6 | — | 0.5820 |
| Fertility, % | 92.6 | 95.9 | — | 0.1727 |
| Chick Weight, g | 42.4 | 41.2 | 0.545 | 0.3039 |
| Relative Chick Weight[1], % | 72.5 | 71.9 | 0.309 | 0.2351 |

[1]expressed as percentage of average egg weight

The broiler breeder treatments had no significant effect on any of the chick performance and quality parameters which were evaluated (Table 8), indicating that 50% replacement of the vitamin E level in the broiler breeder diet by PROVIOX 50 did not affect performance of hatched chickens.

TABLE 8

Broiler Breeder Treatment Effects on Chick Weight, Yolk-sac Weight, Relative Yolk-sac Weight, Yolk-free Body Mass, Chick Length and Shank Relative Asymmetry ("RA") of the Dissected Chickens.

|  | Vit E 50% | PROVIOX | SEM | p-Value |
| --- | --- | --- | --- | --- |
| n | 3 | 3 | — | — |
| Chick Weight, g | 41.3 | 40.5 | 0.6239 | 0.558 |
| Yolk Weight, g | 4.92 | 4.36 | 0.1778 | 0.248 |
| Relative Chick Weight[1], % | 70.7 | 70.7 | 0.4332 | 0.973 |
| Relative Chick Weight[2], % | 11.8 | 10.7 | 0.2955 | 0.180 |
| YFBM[3], g | 36.2 | 36.0 | 0.4554 | 0.808 |
| Chick Length, cm | 17.9 | 17.8 | 0.0772 | 0.760 |
| Relative Assymetrie | 1.59 | 1.52 | 0.1894 | 0.828 |

[1]expressed as percentage of average egg weight
[2]expressed as percentage of chick weight
[3]yolk free body mass Results indicate that the 50% replacement of vitamin E in the broiler breeder diet by PROVIOX 50 has no significant effect on performance of hatched chickens (e.g., fertility, hatchability, and hatched chicken characteristics).

Example 3—Grow Out of Chickens from Example 2

In this Example, the hatched chickens were grown till slaughter age and performance was evaluated. The objective of the current experiment was to evaluate the effect of broiler breeder diet with vitamin E compared to 50% replacement of vitamin E by PROVIOX 50 on offspring performance.

Two different broiler breeder treatments were tested, as shown in Example 1. In this Example, hatched chickens from Example 2 were grown out from eggs obtained in Example 1, where the breeders received the control diet or a diet in which the vitamin E level was 50% replaced by PROVIOX 50.

The experimental period was divided in a starter phase (0-14 days) and a grower phase (14-35 days). Feed and water were provided ad libitum.

A total of 204 male Cobb500 fast-feathering day-chicks, derived from 28-29 week broiler breeders (Example 1), were selected from the total number of hatched male chickens from Example 2. During selection the chickens were randomly selected from different experimental units in the hatchery, ensuring the experimental unit of the broiler breeder facility was kept intact, placing chickens from one experimental unit of the broiler breeder facility into two pens in the grow out facility. Seventeen chickens were housed per cage. To allocate seventeen chickens per cage, buckets with day—chickens of a selected experimental unit of Example 2 were placed in line; from each of the buckets chickens were randomly selected and placed in the selected cage. This procedure continued for all of the cages of this Example.

After placement of the chickens in cages, the individual weights of all chickens per cage were recorded to determine start weight of the chickens. There was a measurable difference in start weights between the different treatments, respectively 40.9 g (±1.6) and 39.9 g (±0.9) for treatments 1 (vitamin E only) and 2 (50% replacement of vitamin E with PROVIOX 50).

Throughout the experiment, chickens were housed in individual broiler grower cages (100×110 cm) on litter (wood shavings). Each cage was equipped with two nipple drinkers with adjustable height. For the first fourteen days, the feeder was inside the cage, and from fourteen days onward, the feed was supplied via a feeder through in front of the cage.

Day length was set for 23 hours a day during the first three days, 20 hours a day from day four until day seven, and 18 hours a day during the remainder of the experiment. Temperature, humidity and ventilation were computer controlled. Temperature was gradually decreased 2.5° C. per week, from 35° C. on the day of arrival to a final temperature of 20.5° C. at the end of the experiment (day 35). Relative humidity in the research facility was set at 50 percent. The birds were spray-vaccinated against Newcastle Disease (Poulvac NDW-vaccine, available from Intervet, Boxmeer, The Netherlands) at 14 days of age.

In advance of diet formulation, batches of wheat, corn, and soybean meal were reserved and analyzed. The diets were produced by Research Diet Services, Wijk bij Duurstede, The Netherlands. Starter and grower diets were produced using one basal diet batch (for each period). Starter diets were pelleted at 2.5 mm and grower diets at 3 mm with steam addition (about 80° C.). Formulation of diets was based on the analyzed nutrient content of the ingredients. Diets were formulated to meet the nutrient requirements of broilers (CVB, 2006). The starter and grower diets contained 2,750 and 2,850 kcal AME·kg$^{-1}$ and 10.20 and 9.70 g·kg$^1$ apparent fecal digestibly (AFD) lysine, respectively. Composition of the experimental diets is given in Table 9, analyses are shown in Table 10.

TABLE 9

Ingredient and Nutrient Composition of the Starter and Grower Diet

| Diet Code | | BG 1301-1 | BG1301-11 |
|---|---|---|---|
| Phase | | Starter | Grower |
| Diet Form | | Pellet - 2.5 mm | Pellet - 3.0 mm |
| Ingredient Composition (%) | | | |
| Corn | | 42.79 | 44.77 |
| Wheat | | 20.00 | 20.00 |
| Soybean meal >48% | | 30.28 | 27.97 |
| Fats/Oils, Soya Oil | | 2.049 | 3.010 |
| Limestone | | 1.694 | 1.349 |
| Monocalciumphosphate | | 1.355 | 1.149 |
| Sodiumbicarbonate | | 0.246 | 0.181 |
| Salt | | 0.217 | 0.213 |
| L - Lysine HCl | | 0.143 | 0.153 |
| DL - Methlonine | | 0.211 | 0.195 |
| L - Threonine | | 0.018 | 0.018 |
| Broiler Premix Starter[1] | | 1.000 | — |
| Broiler Premixer Grower[2] | | — | 1.000 |
| Nutritional Composition (%) - PNC | | | |
| 1120 | Crude Protein | 20.6 | 19.7 |
| 1130 | OIL (EE) | 4.3 | 5.3 |
| 1140 | Crude Fibre | 2.6 | 2.6 |
| 1150 | Ash | 6.2 | 5.5 |
| 1110 | DM | 88.0 | 88.0 |
| 1511 | Calcium | 0.97 | 0.80 |
| 1513 | Phosphor, total | 0.67 | 0.62 |
| 1521 | Na | 0.16 | 0.14 |
| 1522 | K | 0.82 | 0.78 |
| 1523 | Cl | 0.20 | 0.20 |
| 1530 | dEB | 223 | 205 |
| 3310 | Dig. P Broilers | 0.40 | 0.35 |
| 3312 | aP Broilers | 0.43 | 0.38 |
| 3110 | AME Poultry[3] | 2924 | 3022 |
| 3112 | AME Poultry (FS-R) | 2934 | 3031 |
| 3130 | AME Broiler | 2750 | 2850 |
| 1210 | LYS | 1.183 | 1.127 |
| 1211 | MET | 0.514 | 0.487 |
| 1213 | SAA | 0.850 | 0.810 |
| 1214 | THR | 0.777 | 0.740 |
| 1215 | TRP | 0.244 | 0.230 |
| 1216 | ILE | 0.885 | 0.839 |
| 1218 | VAL | 0.961 | 0.916 |
| 1219 | ARG | 1.334 | 1.261 |
| 3200 | AFD LYSp[4] | 1.020 | 0.970 |
| 3201 | AFD METp | 0.477 | 0.451 |
| 3203 | AFD SAAp | 0.745 | 0.708 |
| 3204 | AFD THRp | 0.643 | 0.611 |
| 3205 | AFD TRPp | 0.212 | 0.200 |
| 3206 | AFD ILEp | 0.769 | 0.727 |
| 3208 | AFD VALp | 0.816 | 0.776 |
| 3209 | AFD ARGp | 1.180 | 1.115 |
| 3240 | TFD LYSp[5] | 1.058 | 1.008 |
| 3241 | TFD METp | 0.483 | 0.457 |
| 3243 | TFD SAAp | 0.768 | 0.732 |
| 3244 | TFD THRp | 0.671 | 0.639 |
| 3245 | TFD TRPp | 0.214 | 0.202 |
| 3246 | TFD ILEp | 0.795 | 0.754 |
| 3248 | TFD VALp | 0.859 | 0.819 |

TABLE 9-continued

Ingredient and Nutrient Composition of the Starter and Grower Diet

| Diet Code | BG 1301-1 | BG1301-11 |
|---|---|---|
| Phase | Starter | Grower |
| Diet Form | Pellet - 2.5 mm | Pellet - 3.0 mm |
| 3249 TFD ARGp | 1.221 | 1.154 |
| 1327 C18:2 | 2.1 | 2.6 |

[1] Supplied per kg diet: Vitamin A (retinyl-acetate), 12,000 IU; vitamin $D_3$ (cholecalciferol), 5,000 IU; vitamin E (DL-α-tocopherol),-mg; vitamin $K_3$ (menadione), 2.3 mg; vitamin $B_1$ (thiamine), 1.0 mg; vitamin $B_2$ (riboflavin), 4.5 mg; vitamin $B_6$ (pyridoxine-HCl), 2.7 mg; vitamin B12 (cyanocobalamine), 20 µg; niacine, 40 mg; D-pantothenic acid, 9 mg; choline chloride, 500 mg; folic acid, 0.5 mg; biotin, 100 µg; $FeSO_4 \cdot H_2O$, 150 mg; $CuSO_4 \cdot 5H_2O$, 40 mg; MnO, 100 mg; $ZnSo_4 \cdot H_2O$, 145 mg;; KJ, 2.0 mg; $Na_2SeO_3$, 0.56 mg; antioxidant (oxytrap PXN), - mg.
[2] Supplied per kg diet: vitamin A (retinyl-acetate), 10,000 IU; vitamin $D_3$ (cholecalciferol), 2,000 IU; vitamin E (DL-α-tocopherol), - mg; vitamin $K_3$ (menadione), 2.3 mg; vitamin $B_1$ (thiamine), 0.8 mg; vitamin $B_2$ (riboflavin), 4.5 mg; vitamin $B_6$ (pyridoxine-HCl), 1.9 mg; vitamin B12 (cyanocobalamine), 20 µg; niacine, 30 mg; D-pantothenic acid, 8 mg; choline chloride, 400 mg; folic acid, 0.5 mg; biotin, 50 µg; $FeSO_4 \cdot H_2O$, 150 mg; $CuSO_4 \cdot 5H_2O$, 40 mg; MnO, 100 mg; $ZnSo_4 \cdot H_2O$, 145 mg; KJ, 1.9 mg; $Na_2SeO_3$, 0.50 mg; antioxidant (oxytrap PXN), - mg.
[3] According to CVB (2006) calculations.
[4] AFD = apparent fecal digestibility, CVB (2006) calculations.
[5] TFD = true fecal digestibility.

TABLE 10

Analyzed Nutritional Composition of the Starter and Grower Diets

| Diet Code | Starter BG1301-1 | Grower BG1301-11 |
|---|---|---|
| Calculated Nutrients, % | | |
| Crude Protein | 20.6 | 19.7 |
| Crude Fat | 4.3 | 5.3 |
| Crude Fibre | 2.6 | 2.6 |
| Dry Matter | 88.0 | 88.0 |
| Ca | 0.97 | 0.80 |
| P | 0.67 | 0.60 |
| Analysed Nutrients | | |
| Crude Protein | 20.8 | 20.0 |
| Crude Protein (NIRS) | 21.3 | 19.7 |
| Crude Fat (NIRS) | 4.6 | 5.4 |
| Crude Fibre (NIRS) | 2.5 | 2.6 |
| Moisture (NIRS) | 12.3 | 12.4 |
| Dry Matter | 87.7 | 87.6 |
| Ca | 0.97 | 0.77 |
| P | 0.68 | 0.61 |
| % of expected | | |
| Crude Protein | 102 | 101 |
| Crude Fat | 107 | 102 |
| Crude Fibre | 96 | 102 |
| Dry Matter | 100 | 100 |
| Ca | 100 | 96 |
| P | 101 | 99 |

Individual bird weights were recorded at the start of the experiment (day 0) and at 3, 14, 28 and 35 days of age. In addition, feed consumption for each pen was recorded on the same day the birds were weighed. Based on calculated body weight gain and feed consumption, feed to gain ratio (F:G) was calculated as kg of feed consumed/kg of weight gain. Total feed consumption per pen was corrected for mortality, culling and outliers. The European Poultry Index was calculated using the following formula:

European Poultry Index=(Final Body Wt (g)×(100%−Mortality %))/((10×period in days)overall FCR)

The European Poultry Index excluding mortality was calculated using the following formula:

European Poultry Index=(Final Body Wt (g)×100)/((10×period in days)×overall FCR)

At day 35 of the experiment, five birds per cage (excluding obvious outliers) were selected at random. The birds were slaughtered the next day. In the morning of day 36 these selected birds were killed by $CO_2/O_2$, and blood samples were collected, after that they were bled.

Statistics were performed according to the Provimi Standards for Hypothesis testing and Means Separation, using ANOVA (revision 1.3). For comparison of the different treatments all parameters were subjected to the MIXED MODEL procedure using SAS (Version 9.3, 2008, SAS Institute Inc., Cary, N.C.) according to the following statistical model:

$$Y_{ijkl}=\mu+\alpha_i+b_j+c_k+\alpha c_{ik}+d_l+e_{ijkl};$$

where:
$Y_{ijkl}$=a specific trait measured for each experimental unit
$\mu$=overall mean for the specific trait
$\alpha_i$=Fixed broiler breeder treatment effect (i=1 or 2)
$b_j$=Random storage effect (j=short or long)
$c_k$=Random whole plot block effect (k=1, 2 or 3)
$\alpha c_{ik}$=Random treatment by whole plot block interaction
$d_l$=Random room effect (l=A or B)
$e_{ijkl}$=error term Whole plot block is the block of two experimental units in the broiler breeder facility. The interaction between whole plot block and treatment were included in the model to correct for number of actual replicates in the broiler breeder unit. Mortality was considered as binomial data. Effects were assumed to be significant based on the probability of $P<0.05$ unless other probability value is stated.

Nutritional composition of the diets was in line with the expected values (limit 5% above or below calculated value; Table 10). Observed health status of the birds was good throughout the experiment, though mortality, including culling, reached 6.9%, was high compared with practical levels (3 to 4%) and with previous broiler grower studies (mean 2012: 4.4%). However, no statistical differences in mortality were found between the two broiler breeder treatments.

Table 11 shows the effects of broiler breeder diet (80 ppm vitamin E or 40 ppm vitamin E+40 ppm PROVIOX 50) on mortality, European Poultry Index, average daily weight gain, average daily feed intake, and Feed:Gain of Cobb 500FF broilers.

TABLE 11

Effects of Broiler Breeder Diet

| | Vitamin E | Vitamin E+ + PROVIOX | pooled SEM | P-value |
|---|---|---|---|---|
| n[1] | 3 | 3 | — | — |
| Mortality, % | 4.6 | 9.2 | — | 0.444 |
| EPI, excl mortality | 369 | 344 | 15.3 | 0.438 |
| EPI excl | 388 | 382 | 6.0 | 0.606 |
| BW 0 d, g | 40.9 | 39.9 | 0.55 | 0.275 |
| BW 3 d, g | 69.4 | 67.3 | 1.29 | 0.087 |
| BW 14 d, g | 451 | 436 | 10.0 | 0.449 |
| BW 35 d. g | 2219 | 2181 | 22.5 | 0.114 |
| CV 3 d, % | 7 | 8 | 1.0 | 0.445 |
| CV 14 d, % | 8.2 | 8.6 | 0.82 | 0.815 |
| CV 35 d, % | 7.1 | 8.0 | 0.62 | 0.490 |
| ADG 0-3 d, g | 9.5 | 9.1 | 0.49 | 0.224 |
| ADG 3-14 d, g | 34.7 | 33.5 | 0.86 | 0.511 |
| ADG 14-28 d, g | 79.6 | 78.9 | 1.68 | 0.508 |
| ADG 28-35 d, g | 93.6 | 91.5 | 3.14 | 0.680 |
| ADG 0-14 d, g | 29.3 | 28.3 | 0.73 | 0.490 |
| ADG 0-28 d, g | 54.4 | 53.6 | 0.97 | 0.496 |
| ADG 0-35 d, g | 62.2 | 61.2 | 0.64 | 0.123 |
| ADG 14-35, g | 84.2 | 83.1 | 0.93 | 0.370 |
| ADFI 0-3 d, g | 10.1 | 10.4 | 0.39 | 0.374 |

TABLE 11-continued

Effects of Broiler Breeder Diet

|  | Vitamin E | Vitamin E+ + PROVIOX | pooled SEM | P-value |
|---|---|---|---|---|
| ADFI 3-14 d, g | 44.5 | 43.2 | 1.14 | 0.421 |
| ADFI 14-28 d, g | 127.0 | 124.6 | 2.71 | 0.537 |
| ADFI 28-35 d, g | 180.3 | 178.3 | 1.71 | 0.146 |
| ADFI 0-14 d, g | 37.1 | 36.2 | 0.97 | 0.474 |
| ADFI 0-28 d, g | 82.1 | 80.4 | 1.66 | 0.505 |
| ADFI 0-35 d, g | 101.7 | 100.0 | 1.63 | 0.443 |
| ADFI 14-35, g | 144.8 | 142.5 | 2.28 | 0.451 |
| F:G 0-3 d | 1.088 | 1.151 | 0.024 | 0.151 |
| F:G 3-14 d | 1.283 | 1.290 | 0.018 | 0.836 |
| F:G 14-28 d | 1.598 | 1.580 | 0.024 | 0.647 |
| F:G 28-35 d | 1.929 | 1.958 | 0.071 | 0.809 |
| F:G 0-14 d | 1.268 | 1.279 | 0.015 | 0.679 |
| F:G 0-28 d | 1.509 | 1.500 | 0.020 | 0.791 |
| F:G 0-35 d | 1.635 | 1.634 | 0.020 | 0.984 |
| F:G 14-35 d | 1.720 | 1.715 | 0.025 | 0.924 |
| F:G corrected for BW[2] | 1.627 | 1.634 | 0.020 | 0.883 |

EPI = European poultry index ((Final Body Wt(g) × (100% − Mortality %))/((10 × period in days) × overall FCR)): EPI excl mortality = European poultry index without mortality ((Final Body Wt(g) × 100%)/((10 × period in days) × overall FCR)): ADG = average daily weight gain: ADFI = average daily feed intake: F:G = feed to gain ratio (kg feed intake:kg gain):
[1]Breeder pens with 27-30 hens and 3-4 cooks
[2]F:G corrected to 2,181 gram body weight at 35 days of age. Correction of −0.02 for each 100 g extra weight Referring to Table 11, performance results, average daily gain ("ADG"), average daily feed intake ("ADFI") and feed to gain ratio (F:G) of the offspring were not significantly influenced by the broiler breeder diets.

The results of the broiler breeder experiment indicated that breeder performance was not significantly influenced when vitamin E level was for 50% replaced by PROVIOX 50.

Example 4—Partial Replacement of Vitamin E by PROVIOX 50 in Broiler Breeder Diets All breeders received the same standard control diet during the pre-experimental period (19-30 weeks of age). During the experimental period, breeders received the control diet, a high vitamin E diet, or a diet where the vitamin E level was for 50% replaced by PROVIOX 50 (Table 12).

TABLE 12

Experimental Design of Broiler Breeder Treatments

|  | Inclusion level (ppm) | | Vit E equivalence in |
|---|---|---|---|
| Treatment | Vit E 50 | PROVIOX 50 | diet (ppm) |
| Vit E dose 1 | 160 | — | 80 |
| Vit E dose 2 | 320 | — | 160 |
| PROVIOX dose 1 | 80 | 80 | 80 |
| PROVIOX dose 2 | 160 | 160 | 160 |

In total there were 24 floor pens with 30 breeder females and 3 males (after allocation). The experimental period lasted 9 weeks; the breeders received a lay phase diet during the entire experimental period. Feed and water were restricted. Feed amount depended on body weight development. Water was provided for two hours a day, crops were checked regularly to ensure the correct amount of water was provided.

In advance of diet formulation, batches of soybean meal, wheat middlings, coarsely ground maize and wheat were reserved and wet chemically analyzed for crude protein content, dry matter ("DM"), calcium and phosphorus. In addition soybean meal was analyzed for potassium content and wheat middlings were wet chemically analyzed for crude fiber, potassium and starch. MRS was used to predict crude ash, crude fat, crude fiber and moisture and to cross-check crude protein. Formulation of diets was based on the analyzed nutrient content of the reserved ingredients. One batch of feed was used for the entire experimental period.

A basal diet (corn—soybean meal—wheat and wheat middlings) was formulated based on Provimi nutrient recommendations for broiler breeders. Diet formulations were optimized according to the Provimi Nutrient Code ("PNC") system. A broiler breeder premix was used with no vitamin E and without added other antioxidants. Different male and female diets were produced, though using the same experimental design and using one premix. This was done to be able to feed the males according to their nutritional needs (lower for crude protein, energy, and calcium requirements). Compositions of the experimental diets and analyses are shown in Table 13 and Table 14 respectively. Diets were produced by Research Diet Services, Wijk bij Duurstede, The Netherlands. Both diets were produced separately, using one basal diet batch for the female diets and one basal diet batch for the male diets. Diets were produced as mash.

TABLE 13

Ingredient and Nutritional Composition of the Experimental Diets

| Feedcode | | | | | | | | | | |
|---|---|---|---|---|---|---|---|---|---|---|
| LT1302-1 | LT1302-2 | LT1302-3 | LT1302-4 | LT1302-5 | LT1302-6 | LT1302-7 | LT1302-8 | LT1302-9 | LT1302-10 | LT1302-11 |
| Phase | | | | | | | | | | |
| Pre-lay | Lay Start | Lay Start | Lay Phase | Lay Phase | Lay Phase Treatment | Lay Phase | Lay Phase | Lay Phase | Lay Phase | Lay Phase |
| — | — | — | 1 | 1 | 2 | 2 | 3 | 3 | 4 | 4 |
| Sex | | | | | | | | | | |
| Female & Male | Female | Male | Female | Male | Female | Male | Female | Male | Female | Male |
| Diet Form | | | | | | | | | | |
| Mash | Mash | Mash | Mash | Mash | Mash | Mash | Mash | Mash | Mash | Mash |

| Ingredient Composition (%) | | | | | | | | | | | |
|---|---|---|---|---|---|---|---|---|---|---|---|
| Corn (A5294) | 37.6 | 43.2 | 39.0 | 44.1 | 39.0 | 44.1 | 39.0 | 44.1 | 39.0 | 44.1 | 39.0 |
| Wheat (A5295) | 20.0 | 20.0 | 20.0 | 20.0 | 20.0 | 20.0 | 20.0 | 20.0 | 20.0 | 20.0 | 20.0 |
| Soybean Meal (A5282) | 10.6 | 15.8 | 10.8 | 14.5 | 10.8 | 14.5 | 10.8 | 14.5 | 10.8 | 14.5 | 10.8 |
| Wheat Middlings (A5296) | 25.0 | 10.0 | 25.0 | 10.0 | 25.0 | 10.0 | 25.0 | 10.0 | 25.0 | 10.0 | 25.0 |
| Limestone Coarse | 2.2 | 5.0 | 1.1 | 5.2 | 1.1 | 5.2 | 1.1 | 5.2 | 1.1 | 5.2 | 1.1 |
| Limestone Fine | 1.1 | 2.5 | 0.6 | 2.6 | 0.6 | 2.6 | 0.6 | 2.6 | 0.6 | 2.6 | 0.6 |
| Monocalcium Phosphate | 1.0 | 1.1 | 1.0 | 1.1 | 1.0 | 1.1 | 1.0 | 1.1 | 1.0 | 1.1 | 1.0 |
| Soya Oil | 1.0 | 1.0 | 1.0 | 1.0 | 1.0 | 1.0 | 1.0 | 1.0 | 1.0 | 1.0 | 1.0 |
| Premix[1] (1%) | 1.0 | 1.0 | 1.0 | 1.0 | 1.0 | 1.0 | 1.0 | 1.0 | 1.0 | 1.0 | 1.0 |
| Salt | 0.17 | 0.25 | 0.19 | 0.21 | 0.19 | 0.21 | 0.19 | 0.21 | 0.19 | 0.21 | 0.19 |
| Na-Bicarbonate | 0.15 | 0.01 | 0.13 | 0.063 | 0.13 | 0.063 | 0.13 | 0.063 | 0.13 | 0.063 | 0.13 |
| DL-Methionine | 0.075 | 0.118 | 0.068 | 0.120 | 0.068 | 0.120 | 0.068 | 0.120 | 0.068 | 0.120 | 0.068 |
| L-Lysine HCL | 0.089 | 0.049 | 0.053 | 0.063 | 0.053 | 0.063 | 0.053 | 0.063 | 0.053 | 0.063 | 0.053 |
| L-Threoine | 0.004 | — | — | — | — | — | — | — | — | — | — |
| Vitamin E 50% | 0.010 | 0.012 | 0.012 | 0.016 | 0.016 | 0.032 | 0.032 | 0.008 | 0.008 | 0.016 | 0.016 |
| Proviox 50 | — | — | — | — | — | — | — | 0.008 | 0.008 | 0.016 | 0/016 |
| Nutritional Composition (%) - based on Provimi Nutrient Code System | | | | | | | | | | | |
| 1120 Crude Protein | 14.5 | 15.0 | 14.6 | 14.5 | 14.6 | 14.5 | 14.6 | 14.5 | 14.6 | 14.5 | 14.6 |
| 1130 Crude Fat | 3.80 | 3.53 | 3.85 | 3.53 | 3.85 | 3.53 | 3.85 | 3.53 | 3.85 | 3.53 | 3.85 |
| 1140 Crude Fibre | 3.75 | 2.86 | 3.79 | 2.83 | 3.79 | 2.83 | 3.79 | 2.83 | 3.79 | 2.83 | 3.79 |
| 1150 Ash | 7.2 | 11.2 | 5.7 | 11.5 | 5.7 | 11.5 | 5.7 | 11.5 | 5.7 | 11.5 | 5.7 |
| 1110 Dry Matter | 88.1 | 88.5 | 87.9 | 88.6 | 87.9 | 88.6 | 87.9 | 88.6 | 87.9 | 88.6 | 87.9 |
| 1511 Calcium | 1.50 | 3.10 | 0.90 | 3.25 | 0.90 | 3.25 | 0.90 | 3.25 | 0.90 | 3.25 | 0.90 |
| 1513 Phosphorus P | 0.70 | 0.62 | 0.70 | 0.61 | 0.70 | 0.61 | 0.70 | 0.61 | 0.70 | 0.61 | 0.70 |
| 3312 Av. P | 0.35 | 0.36 | 0.35 | 0.35 | 0.35 | 0.35 | 0.35 | 0.35 | 0.35 | 0.35 | 0.35 |
| 3311 Dig. P Layers | 0.35 | 0.34 | 0.35 | 0.33 | 0.35 | 0.33 | 0.35 | 0.33 | 0.35 | 0.33 | 0.35 |
| 1521 Sodium | 0.14 | 0.14 | 0.14 | 0.14 | 0.14 | 0.14 | 0.14 | 0.14 | 0.14 | 0.14 | 0.14 |
| 1522 Potassium | 0.73 | 0.68 | 0.73 | 0.66 | 0.73 | 0.66 | 0.73 | 0.66 | 0.73 | 0.66 | 0.73 |
| 1523 Chloride | 0.16 | 0.20 | 0.17 | 0.18 | 0.17 | 0.18 | 0.17 | 0.18 | 0.17 | 0.18 | 0.17 |
| 1530 dEB | 200 | 178 | 200 | 177 | 200 | 177 | 200 | 177 | 200 | 177 | 200 |
| 3110 ME Poultry | 2710 | 2712 | 2759 | 2712 | 2759 | 2712 | 2759 | 2712 | 2759 | 2712 | 2759 |
| 3112 ME Poultry (FS-R) | 2713 | 2733 | 2763 | 2732 | 2763 | 2732 | 2763 | 2732 | 2763 | 2732 | 2763 |
| 3120 ME Layer | 2750 | 2750 | 2800 | 2750 | 2800 | 2750 | 2800 | 2750 | 2800 | 2750 | 2800 |
| 1210 LYS | 0.689 | 0.729 | 0.670 | 0.705 | 0.670 | 0.705 | 0.670 | 0.705 | 0.670 | 0.705 | 0.670 |
| 1211 MET | 0.304 | 0.354 | 0.301 | 0.349 | 0.301 | 0.349 | 0.301 | 0.349 | 0.301 | 0.349 | 0.301 |
| 1213 SAA | 0.577 | 0.623 | 0.577 | 0.611 | 0.577 | 0.611 | 0.577 | 0.611 | 0.577 | 0.611 | 0.577 |
| 1214 THR | 0.506 | 0.535 | 0.509 | 0.515 | 0.509 | 0.515 | 0.509 | 0.515 | 0.509 | 0.515 | 0.509 |
| 1215 TRP | 0.170 | 0.173 | 0.172 | 0.166 | 0.172 | 0.166 | 0.172 | 0.166 | 0.172 | 0.166 | 0.172 |
| 1216 ILE | 0.538 | 0.590 | 0.546 | 0.566 | 0.546 | 0.566 | 0.546 | 0.566 | 0.546 | 0.566 | 0.546 |
| 1218 VAL | 0.664 | 0.693 | 0.674 | 0.669 | 0.674 | 0.669 | 0.674 | 0.669 | 0.674 | 0.669 | 0.674 |
| 1219 ARG | 0.887 | 0.933 | 0.898 | 0.893 | 0.898 | 0.893 | 0.898 | 0.893 | 0.898 | 0.893 | 0.898 |
| 3200 AFD LYSp | 0.560 | 0.600 | 0.540 | 0.580 | 0.540 | 0.580 | 0.540 | 0.580 | 0.540 | 0.580 | 0.540 |
| 3201 AFD METp | 0.267 | 0.320 | 0.263 | .0316 | 0.263 | 0.316 | 0.263 | 0.316 | 0.263 | 0.316 | 0.263 |
| 3203 AFD SAAp | 0.480 | 0.530 | 0.480 | 0.520 | 0.480 | 0.520 | 0.480 | 0.520 | 0.480 | 0.520 | 0.480 |
| 3204 AFD THRp | 0.390 | 0.424 | 0.393 | 0.406 | 0.393 | 0.406 | 0.393 | 0.406 | 0.393 | 0.406 | 0.393 |
| 3205 AFD TRPp | 0.141 | 0.147 | 0.143 | 0.140 | 0.143 | 0.140 | 0.143 | 0.140 | 0.143 | 0.140 | 0.143 |
| 3206 AFD ILEp | 0.448 | 0.501 | 0.456 | 0.480 | 0.456 | 0.480 | 0.456 | 0.480 | 0.456 | 0.480 | 0.456 |
| 3208 AFD VALp | 0.538 | 0.572 | 0.547 | 0.551 | 0.547 | 0.551 | 0.547 | 0.551 | 0.547 | 0.551 | 0.547 |
| 3209 AFD ARGp | 0.771 | 0.817 | 0.782 | 0.781 | 0.782 | 0.781 | 0.782 | 0.781 | 0.782 | 0.781 | 0.782 |
| 3240 TFD LYSp | 0.592 | 0.636 | 0.572 | 0.616 | 0.572 | 0.616 | 0.572 | 0.616 | 0.572 | 0.616 | 0.572 |

| | | | | | | | | | | |
|---|---|---|---|---|---|---|---|---|---|---|
| 3241 TFD METp | 0.275 | 0.328 | 0.272 | 0.324 | 0.272 | 0.324 | 0.272 | 0.324 | 0.272 | 0.324 | 0.272 |
| 3243 TFD SAAp | 0.502 | 0.556 | 0.501 | 0.546 | 0.501 | 0.546 | 0.501 | 0.546 | 0.501 | 0.546 | 0.501 |
| 3244 TFD THRp | 0.421 | 0.455 | 0.423 | 0.438 | 0.423 | 0.438 | 0.423 | 0.438 | 0.423 | 0.438 | 0.423 |
| 3245 TFD TRPp | 0.145 | 0.150 | 0.146 | 0.144 | 0.146 | 0.144 | 0.146 | 0.144 | 0.146 | 0.144 | 0.146 |
| 3246 TFD ILEp | 0.474 | 0.528 | 0.481 | 0.507 | 0.481 | 0.507 | 0.481 | 0.507 | 0.481 | 0.507 | 0.481 |
| 3248 TFD VALp | 0.572 | 0.613 | 0.581 | 0.591 | 0.581 | 0.591 | 0.581 | 0.591 | 0.581 | 0.591 | 0.581 |
| 3249 TFD ARGp | 0.803 | 0.852 | 0.814 | 0.815 | 0.814 | 0.815 | 0.814 | 0.815 | 0.814 | 0.815 | 0.814 |
| 1327 C18:2 | 1.75 | 1.65 | 1.77 | 1.66 | 1.77 | 1.66 | 1.77 | 1.66 | 1.77 | 1.66 | 1.77 |
| Vitamen E equivalent (IU) | 50 | 60 | 60 | 80 | 80 | 160 | 160 | 80 | 80 | 160 | 160 |

[1]Supplied per kg diet Pre-Lay: riboflavin, 7.5 mg; niacinamide, 30 mg; D-pantothenic acid, 9 mg; choline chloride, 500 mg; DL-α-tocopherol, - IU; menadione, 3.5 mg; retinyl-acetate, 10000 IU; cholecalciferol, 2000 IU; biotin, 100 μg; folic acid, 1.0 mg; Thiamine, 2.0 mg; pyridoxine-HCl, 3.0 mg; cyanocobalamine, 25 μg; $FeSO_4 \cdot H_2O$, 147 mg; $MnO_2$, 106 mg; $CuSO_4 \cdot 5H_2O$, 40 mg; $ZnSO_4 \cdot H_2O$, 206 mg; $Na_2SeO_3$, 0.88 mg; KJ, 1.9 mg; antioxidant (Oxytrap PXN), - mg. Supplied per kg diet Lay start: riboflavin, 9.0 mg; niacinamide, 40 mg; D-pantothenic acid, 12 mg; choline chloride, 600 mg; DL-α-tocopherol, - IU; menadione, 2.5 mg; retinyl-acetate, 12500 IU; cholecalciferol, 2500 IU; biotin, 150 μg; folic acid, 1.5 mg; Thiamine, 2.0 mg; pyridoxine-HCl, 4.5 mg; cyanocobalamine, 30 μg; $FeSO_4 \cdot H_2O$, 147 mg; $MnO_2$, 130 mg; $CuSO_4 \cdot 5H_2O$, 40 mg; $ZnSO_4 \cdot H_2O$, 206 mg; $Na_2SeO_3$, 0.88 mg; KJ, 2.6 mg; antioxidant (Oxytrap PXN), - mg. Supplied per kg diet Lay phase: riboflavin, 6.0 mg; niacinamide, 30 mg; D-pantothenic acid, 9 mg; choline chloride, 350 mg; DL-α-tocopherol, - IU; menadione, 2.5 mg; retinyl-acetate, 12500 IU; cholecalciferol, 2500 IU; biotin, 100 μg; folic acid, 1.0 mg; Thiamine, 1.0 mg; pyridoxine-HCl, 2.5 mg; cyanocobalamine, 25 μg; $FeSO_4 \cdot H_2O$, 147 mg; $MnO_2$, 114 mg; $CuSO_4 \cdot 5H_2O$, 40 mg; $ZnSO_4 \cdot H_2O$, 206 mg; $Na_2SeO_3$, 0.88 mg; KJ, 2.6 mg; antioxidant (Oxytrap PXN), - mg.

TABLE 14

Analyzed Nutritional Composition of the Experimental Diets[1]

| | \multicolumn{8}{c}{Feedcode} | | | | | | | |
|---|---|---|---|---|---|---|---|---|
| | LT1302-1 | LT1302-2 | LT1302-3 | LT130-4 Batch 1 | LT1302-4 Batch 2 | LT1302-5 | LT1302-6 Batch 1 | LT1302-6 Batch 2 |
| \multicolumn{9}{c}{Calculated Nutrients, %} | | | | | | | | |
| Crude Protein | 14.5 | 15.0 | 14.6 | 14.5 | 14.5 | 14.6 | 14.5 | 14.5 |
| Crude Fat | 3.8 | 3.5 | 3.9 | 3.5 | 3.5 | 3.9 | 3.5 | 3.5 |
| Crude Fibre | 3.7 | 2.9 | 3.8 | 2.8 | 28 | 3.8 | 2.8 | 2.8 |
| Dry Matter | 88.1 | 88.5 | 87.9 | 88.6 | 88.6 | 87.9 | 88.6 | 88.6 |
| Ca | 1.50 | 3.10 | 0.90 | 3.25 | 3.25 | 0.90 | 3.25 | 3.25 |
| P | 0.70 | 0.62 | 0.70 | 0.61 | 0.61 | 0.70 | 0.61 | 0.61 |
| \multicolumn{9}{c}{Analysed Nutrients} | | | | | | | | |
| Crude Protein | 14.6 | 14.9 | 14.6 | 15.0 | 14.6 | 15.4 | 15.2 | 14.8 |
| Crude Protein (NIRS) | 14.7 | 14.8 | 14.5 | 15.4 | 15.0 | 15.4 | 15.4 | 15.3 |
| Crude Fat (NIRS) | 3.5 | 2.9 | 3.6 | 2.9 | 2.8 | 3.6 | 2.8 | 2.9 |
| Crude Fibre (NIRS) | 3.7 | 2.9 | 4.0 | 2.9 | 3.0 | 4.0 | 2.8 | 3.0 |
| Moisture (NIRS) | 11.7 | 11.4 | 11.6 | 11.5 | 11.4 | 11.8 | 11.7 | 11.4 |
| Dry Matter | 88.3 | 88.6 | 88.4 | 88.5 | 88.6 | 88.2 | 88.3 | 88.6 |
| Ca | 1.6 | 2.8 | 0.8 | 3.4 | 3.6 | 1.1 | 3.2 | 3.6 |
| P | 0.7 | 0.6 | 0.6 | 0.6 | 0.6 | 0.7 | 0.6 | 0.6 |
| \multicolumn{9}{c}{% of expected} | | | | | | | | |
| Crude Protein | 101 | 99 | 99 | 105 | 102 | 105 | 106 | 104 |
| Crude Fat | 92 | 82 | 94 | 82 | 79 | 94 | 79 | 82 |
| Crude Fibre | 99 | 101 | 106 | 102 | 106 | 106 | 99 | 106 |
| Dry Matter | 100 | 100 | 101 | 100 | 100 | 100 | 100 | 100 |
| Ca | 105 | 90 | 92 | 106 | 111 | 123 | 99 | 111 |
| P | 104 | 99 | 91 | 102 | 104 | 105 | 101 | 104 |

| | \multicolumn{7}{c}{Feedcode} | | | | | | |
|---|---|---|---|---|---|---|---|
| | LT1302-7 | LT1302-8 Batch 1 | LT1302-8 Batch 2 | LT1302-9 | LT1302-10 Batch 1 | LT1302-10 Batch 2 | LT1302-11 |
| \multicolumn{8}{c}{Calculated Nutrients, %} | | | | | | | |
| Crude Protein | 14.6 | 14.5 | 14.5 | 14.6 | 14.5 | 14.5 | 14.6 |
| Crude Fat | 3.9 | 3.5 | 3.5 | 3.9 | 3.5 | 3.5 | 3.9 |
| Crude Fibre | 3.8 | 2.8 | 2.8 | 3.8 | 2.8 | 2.8 | 3.8 |
| Dry Matter | 87.9 | 88.6 | 88.6 | 87.9 | 88.6 | 88.6 | 87.9 |
| Ca | 0.90 | 3.25 | 3.25 | 0.90 | 3.25 | 3.25 | 0.90 |
| P | 0.70 | 0.61 | 0.61 | 0.70 | 0.61 | 0.61 | 0.70 |

TABLE 14-continued

Analyzed Nutritional Composition of the Experimental Diets[1]

Analysed Nutrients

| | | | | | | | |
|---|---|---|---|---|---|---|---|
| Crude Protein | 15.0 | 14.7 | 14.5 | 14.8 | 15.4 | 14.8 | 14.8 |
| Crude Protein (NIRS) | 15.0 | 15.2 | 15.2 | 15.3 | 15.6 | 15.5 | 15.0 |
| Crude Fat (NIRS) | 3.6 | 2.9 | 2.9 | 3.6 | 3.0 | 2.9 | 3.7 |
| Crude Fibre (NIRS) | 4.0 | 3.0 | 3.0 | 3.8 | 2.9 | 2.9 | 4.0 |
| Moisture (NIRS) | 11.9 | 11.5 | 11.6 | 11.8 | 11.4 | 11.5 | 11.9 |
| Dry Matter | 88.1 | 88.5 | 88.4 | 88.2 | 88.6 | 88.5 | 88.1 |
| Ca | 1.1 | 3.6 | 3.0 | 1.1 | 3.5 | 3.2 | 1.0 |
| P | 0.7 | 0.7 | 0.6 | 0.7 | 0.7 | 0.6 | 0.7 |
| % of expected | | | | | | | |
| Crude Protein | 103 | 103 | 102 | 103 | 107 | 104 | 102 |
| Crude Fat | 94 | 82 | 82 | 94 | 85 | 82 | 96 |
| Crude Fibre | 106 | 106 | 106 | 100 | 102 | 102 | 106 |
| Dry Matter | 100 | 100 | 100 | 100 | 100 | 100 | 100 |
| Ca | 120 | 111 | 93 | 117 | 109 | 99 | 108 |
| P | 105 | 114 | 99 | 104 | 111 | 98 | 105 |

[1]The amount of female diets for the lay period was too much to produce in one batch, therefore two batches were produced with the same ingredients.
A total of 730 female and 92 male Ross 308 19-week-breeders were procured. On arrival (at the start of the pre-experiment period) the males and females were randomly assigned to the floor pens (3-4 males and 30-31 females per pen). Breeders were reallocated at the start of experimental period (30 females and 3 males per pen, remaining healthy males were placed in a spare pen, remaining females were culled).
Throughout the experiment breeders were housed in individual broiler breeder floor pens (2.60 × 2.40 m) on litter (flax). Each pen was equipped with one bell drinker, adjustable in height. The feed for the females was supplied via two feeder bowls on the raised slatted floor; the feed for the males was supplied via a feeder trough on the other side of the pen. Breeders were light stimulated during the pre-experimental period according to breed standards. During the experimental period day length was set for 15 hours a day. Temperature and ventilation was computer controlled. Temperature was set to 20° C. for the complete period. Individual bird weights were recorded weekly from the start of the pre-experimental period. At 31, 33, and 36 weeks of age 50% of the females were weighed, and at 35, 37 and 38 weeks of age only the first four pens were weighed to determine proper weight development. Feed amount provided was recorded on a daily basis. Egg production and egg quality data were recorded on a daily basis. Laying % was calculated as number of eggs produced per pen divided by the number of bird days of the experimental period. Egg mass production per pen per week was calculated as laying % (including second class eggs) times average egg weight of the pen. Average egg weight was determined per pen once a week. Second class eggs were divided into dirty eggs, broken eggs, shell-less eggs, double yolk eggs, floor eggs and remaining second-class eggs. Mortality was checked every day; dead animals were not replaced during the experimental period.

Eggs were shipped to University Gent, Belgium, for ORAC and vitamin E analysis on the yolk. The method used for the determination of polyphenols was the Folin-Ciocalteu Methodology which is described in the European Pharmacopoeia, using a spectrophotometry UV-visible. For the ORAC analysis the method was used as described by Ou et al. "Development and validation of an improved oxygen radical absorbance capacity assay using fluorescein as the fluorescent probe," Journal of Agricultural and Food Chemistry 49: 4619-4626, (2001) and Huang et al. "High-throughput assay of oxygen radical absorbance capacity (ORAC) using a multichannel liquid handling system coupled with a microplate fluorescence reader in 96-well format," Journal of Agricultural and Food Chemistry 50: 4437-4444, (2002).

Statistics were performed according to the Provimi Standards for Hypothesis testing and Means Separation, using ANOVA (revision 1.3). For comparison of the different treatments all parameters were subjected to the MIXED MODEL procedure using SAS (Version 9.2, 2008, SAS Institute Inc., Cary, N.C., USA) according to the following statistical model:

$$Y_{ij} = \mu + \alpha_i + b_j + \varepsilon_{ij}$$

where:
$Y_{ij}$=a specific trait per experimental unit (pen)
$\mu$=overall mean for the specific trait
$\alpha_i$=fixed treatment effect (i=1, 2, 3 or 4)
$b_j$=random block effect (j=1, 2, . . . , 6)
$\varepsilon_{ij}$=error term Contrasts were used to compare treatment effects. The contrast descriptions are given below and the contrast specifications to answer each question are shown in Table 15.
1) Was there a linear vitamin E effect?
2) Was there a PROVIOX 50 replacement effect?
3) Was the PROVIOX 50 replacement effect dependent on dose?
4) Was there an additive effect of adding PROVIOX 50 on top of vitamin E?

TABLE 15

Contrast Statements Used for Statistical Analysis.

| | Vit E dose 1 | Vit E dose 2 | PROVIOX dose 1 | PROVIOX dose 2 |
|---|---|---|---|---|
| 1) | −1 | 1 | 0 | 0 |
| 2) | −1 | −1 | 1 | 1 |
| 3) | −1 | 1 | 1 | −1 |
| 4) | −1 | 0 | 0 | 1 |

Nutritional composition of the diets was reasonably in line with the expected values (Table 14). Observed health status of the birds was good throughout the experiment. Mortality, including culling, reached 6.1%, which is on the high side compared to breeding standards (total mortality and culling during the laying period 8%). This was mainly due to a relatively high culling percentage due to leg problems around 30 weeks of age, which is more often observed with Ross breeders. Technical performance was in line with breeder standards of Ross 308 (data not shown). During the overall experimental period (30-39 weeks of age), percentage of broken eggs was significantly 47% lower when vitamin E was partially replaced (50%) by PROVIOX 50 (Table 16). This suggest there was an improvement in egg shell strength which is important as the number of settable eggs will increase, resulting in a higher revenue per broiler breeder for the farmer.

Technical results of breeders fed the experimental diets (weeks 30 through 39 of age) are shown in Table 16.

TABLE 16

Technical results of breeders fed the experimental diets (week 30 through 39 of age)

| Vitamin E equivalence (ppm) | Vit E dose 1 80 | Vit E dose 2 160 | Proviox 50% 80 | Proviox 50% 160 | Pooled SEM | Overall P-Value | Linear Vit E effect | Proviox Replacement Effect | Proviox Replacement Depended On Dose | Additive Effect of Proviox Adding on Top |
|---|---|---|---|---|---|---|---|---|---|---|
| n | 6 | 6 | 6 | 6 | — | — | — | — | — | — |
| Laying in percentage 30-34 wks, % | 87.1 | 87.0 | 83.7 | 84.8 | 1.1842 | 0.143 | 0.931 | 0.029 | 0.604 | 0.175 |
| Laying in percentage 34-39 wks, % | 81.5 | 83.0 | 77.0 | 80.5 | 1.6050 | 0.087 | 0.511 | 0.041 | 0.532 | 0.657 |
| Laying in percentage 30-39 wks, % | 84.3 | 85.0 | 80.4 | 82.7 | 1.1941 | 0.054 | 0.689 | 0.015 | 0.494 | 0.319 |
| First Class Eggs 30-34 wks, % | 80.2 | 78.6 | 76.5 | 76.5 | 1.6123 | 0.299 | 0.476 | 0.081 | 0.601 | 0.115 |
| First Class Eggs 34-39 wks, % | 73.8 | 74.4 | 69.5 | 71.1 | 2.0875 | 0.254 | 0.824 | 0.060 | 0.807 | 0.317 |
| First Class Eggs 30-39 wks, % | 77.0 | 76.5 | 73.0 | 73.8 | 1.6706 | 0.198 | 0.818 | 0.040 | 0.671 | 0.149 |
| Second Choice Eggs | | | | | | | | | | |
| Broken Eggs 30-34 wks, % | 1.2 | 1.2 | 0.4 | 0.7 | 0.4041 | 0.359 | 0.877 | 0.101 | 0.592 | 0.330 |
| Broken Eggs 34-39 wks, % | 1.2 | 1.5 | 0.4 | 1.1 | 0.3242 | 0.026 | 0.429 | 0.024 | 0.303 | 0.843 |
| Broken Eggs 30-39 wks, % | 1.2 | 1.3 | 0.4 | 0.9 | 0.3186 | 0.071 | 0.795 | 0.025 | 0.377 | 0.411 |
| Dirty Eggs 30-34 wks, % | 1.4 | 1.8 | 1.6 | 1.6 | 0.2805 | 0.836 | 0.372 | 0.942 | 0.502 | 0.634 |
| Dirty Eggs 34-39 wks, % | 1.9 | 1.7 | 1.6 | 1.4 | 0.2631 | 0.711 | 0.600 | 0.343 | 0.918 | 0.267 |
| Dirty Eggs 30-39 wks, % | 1.7 | 1.8 | 1.6 | 1.5 | 0.2360 | 0.944 | 0.821 | 0.618 | 0.740 | 0.717 |
| Shell less Eggs 30-34 wks, % | 0.2 | 0.3 | 0.2 | 0.1 | 0.0901 | 0.751 | 0.524 | 0.731 | 0.315 | 0.745 |
| Shell less Eggs 34-39 wks, % | 0.0 | 0.2 | 0.1 | 0.1 | 0.0537 | 0.116 | 0.021 | 0.992 | 0.167 | 0.138 |
| Shell less Eggs 30-39 wks, % | 0.1 | 0.2 | 0.2 | 0.1 | 0.0579 | 0.429 | 0.124 | 0.779 | 0.162 | 0.705 |
| 0Double yolk Eggs 30-34 wks, % | 1.3 | 1.1 | 1.3 | 1.3 | 0.2363 | 0.923 | 0.590 | 0.720 | 0.804 | 0.911 |
| Double yolk Eggs 34-39 wks, % | 0.4 | 0.5 | 0.5 | 0.4 | 0.1216 | 0.888 | 0.759 | 0.959 | 0.473 | 0.867 |
| Double yolk Eggs 30-39 wks, % | 0.9 | 0.8 | 0.9 | 0.8 | 0.1698 | 0.960 | 0.788 | 0.790 | 0.939 | 0.893 |
| Floor eggs, 30-34 wks, % | 2.3 | 3.3 | 3.0 | 3.5 | 0.9608 | 0.508 | 0.255 | 0.426 | 0.685 | 0.162 |
| Floor eggs, 34-39 wks, % | 3.4 | 4.1 | 4.3 | 5.4 | 1.3350 | 0.572 | 0.608 | 0.291 | 0.862 | 0.175 |
| Floor eggs, 30-39 wks, % | 2.8 | 3.7 | 3.7 | 4.5 | 1.1179 | 0.526 | 0.430 | 0.310 | 0.967 | 0.148 |
| Remainder 30-34 wks, % | 0.5 | 0.8 | 0.5 | 1.0 | 0.2043 | 0.334 | 0.342 | 0.675 | 0.672 | 0.133 |
| Remainder 34-39 wks, % | 0.8 | 0.6 | 0.6 | 0.9 | 0.1630 | 0.485 | 0.543 | 0.616 | 0.176 | 0.469 |
| Remainder 30-39 wks, % | 0.6 | 0.7 | 0.6 | 0.9 | 0.1499 | 0.262 | 0.756 | 0.546 | 0.257 | 0.133 |
| Egg weight 30-34 wks, g | 60.1 | 60.3 | 60.2 | 59.6 | 0.3530 | 0.520 | 0.695 | 0.431 | 0.264 | 0.336 |
| Egg weight 34-39 wks, g | 62.4 | 62.9 | 63.1 | 62.4 | 0.3324 | 0.392 | 0.318 | 0.752 | 0.103 | 0.975 |
| Egg weight 30-39 wks, g | 61.2 | 61.6 | 61.7 | 61.0 | 0.3284 | 0.497 | 0.472 | 0.803 | 0.156 | 0.626 |
| Egg mass 30-34 wks, g/h/d | 52.4 | 52.5 | 50.4 | 50.5 | 0.7345 | 0.088 | 0.931 | 0.013 | 0.994 | 0.076 |
| Egg mass 34-39 wks, g/h/d | 50.9 | 52.2 | 48.7 | 50.2 | 1.0783 | 0.169 | 0.379 | 0.069 | 0.919 | 0.688 |
| Egg mass 30-39 wks, g/h/d | 51.6 | 52.4 | 49.5 | 50.4 | 0.7964 | 0.089 | 0.519 | 0.020 | 0.948 | 0.272 |
| Bodyweight 30 wks, kg | 3.51 | 3.48 | 3.51 | 3.51 | 0.0230 | 0.513 | 0.192 | 0.476 | 0.351 | 0.869 |
| Bodyweight 39 wks, kg | 3.88 | 3.83 | 3.85 | 3.81 | 0.0239 | 0.307 | 0.176 | 0.348 | 0.765 | 0.078 |
| CV Bodyweight 30 wk, % | 7.9 | 7.5 | 7.7 | 7.3 | 0.4641 | 0.888 | 0.657 | 0.723 | 0.951 | 0.464 |
| CV Bodyweight 39 wk, % | 8.6 | 8.2 | 8.7 | 7.8 | 0.5199 | 0.673 | 0.663 | 0.841 | 0.624 | 0.361 |
| Average daily gain 30-34 wk, g | 5.36 | 5.65 | 5.35 | 4.94 | 0.4223 | 0.654 | 0.610 | 0.377 | 0.384 | 0.461 |
| Average daily gain 34-39 wk, g | 5.96 | 5.40 | 5.25 | 4.66 | 0.3624 | 0.081 | 0.240 | 0.041 | 0.966 | 0.012 |
| Average daily gain 30-39 wk, g | 5.79 | 5.60 | 5.38 | 4.86 | 0.2857 | 0.022 | 0.500 | 0.010 | 0.403 | 0.004 |

Table 17 shows the results of analysis of egg yolk contents for ORAC and vitamin E level. Referring to Table 17, the evaluation of the egg yolk for ORAC and vitamin E content showed no significant differences between the treatment groups on ORAC, vitamin E content, however, showed linear increased due to increases in vitamin E level in the diet. The found proportionality index was around 50% for the transfer of vitamin E from the diet to the egg which is in agreement with previous studies (Hossain et al., 1998).

placed in incubator machine 2. During this period, the incubator temperature was set at 36.7° C. and relative humidity at 70%.

Group egg weights were recorded at E0. At E7 and E18, all eggs were candled and empty eggs or eggs containing dead embryos were removed (early dead E0-E7, mid dead E8-E18). At E18 eggs were transferred to the hatching baskets after candling. At hatch (E21) the number of dead chickens, late dead embryos (E19-E21) and pipped eggs

TABLE 17

Results of Analysis of Egg Yolk Contents for ORAC and Vitamin E Level

| Vitamin E equivalence (ppm) | Vit E dose 1 80 | Vit E dose 2 160 | Proviox 50% 80 | Proviox 50% 160 | Pooled SEM | Overall P-Value | Linear vit E Effect | Proviox Replacement Effect | Proviox Replacement Depended On Dose | Additive Effect of Proviox Adding on Top |
|---|---|---|---|---|---|---|---|---|---|---|
| n | 6 | 6 | 6 | 6 | — | — | — | — | — | — |
| ORAC, □mol TE/g | 33.8 | 33.5 | 34.2 | 35.1 | 1.35 | 0.7682 | 0.8417 | 0.3789 | 0.6124 | 0.4341 |
| Vitamin E, □g □□tocoferol/g | 139.7 | 231.6 | 92.0 | 165.5 | 15.0 | 0.0004 | 0.0018 | 0.0047 | 0.5989 | 0.3052 |

Results of this Example showed no beneficial effects on any of the evaluated parameters for using PROVIOX 50 in the breeder diet.

Example 5—Chicken Production from Eggs of Example 4

For a period of six days, eggs were collected from the broiler breeder flock of Example 4 above. The eggs were stored based on breeder pen and storage day for an additional three days before the brooding period started. All eggs were incubated until hatch. All eggs were distributed over 24 trays and 6 blocks, with each block representing a storage day. Breeders received one of the four experimental diets, as shown in Table 12.

A total of 2160 eggs derived from the 37-38 week broiler breeders (Ross 308) of Example 4 were collected and stored in the egg storage unit of the broiler breeder facility. At the start of the incubation period, the eggs were weighed and allocated into blocks, each block representing a storage day. Each block consisted of 24 experimental units, with each experimental unit indicating a group of 15 eggs. Only intact eggs were included and eggs that were cracked, dirty or that had deformed shells were excluded from the trial.

The eggs were placed in a Nature Form NMC 2340 Incubator with automatic control of temperature and relative humidity. From E0 till E18 the eggs were placed in setter trolleys, which consist of two shelves with a capacity for 13 trays each. Each tray has three flats of 30 eggs each. During this period, the incubator start temperature was set at 37.5° C. and relative humidity at 54%. Temperature started at 37.5° C. at E0 and gradually decreased From E12 till E18 from 37.5° C. to 36.7° C.

After the setter period (E0-E18), eggs were transferred to baskets in the hatchers based on the blocking and tray structure in the setter. The eggs were placed into subdivisions of a hatching crate (per experimental unit of 15 eggs), and following tray order per block (starting with 1AO ending with 24CI). Each hatcher trolley has twelve baskets with a capacity of 180 eggs each. Eggs of tray 1-12 were placed in incubator machine 1, eggs of tray 13-24 were placed in incubator machine 2. During this period, the incubator temperature was set at 36.7° C. and relative humidity at 70%.

were recorded. The number of hatched chickens was recorded per replicate, as well as average chick weight. Hatchability was calculated as percentage of total eggs set. Sex was determined by feather sexing, female chickens were euthanized by $CO_2$ and disposed according to local regulations. Per experimental unit, five male chickens were selected for the grow-out period and allocated to broiler grower pens. Only chickens with an average body weight, completely dry, showing active movement and with a good navel score were selected. After this selection one male chicken per experimental unit was selected for dissection. Sample chickens were individually weighed and killed by cervical dislocation to measure remaining yolk-sac weights, yolk-free body mass ("YFBM"), liver weight, chick length, and shank length of both shanks. The livers were immediately placed on dry ice and after dissection stored at −20° C. for further analysis ("SOD and GSSG"). Relative asymmetry was calculated according to the following formula:

$$RA=(|L-R|/[(L+R)/2])\times 100.$$

where:
L=left shank length
R=right shank length.

To evaluate if there were significant differences between the different broiler breeder treatments, all parameters we also subjected to Mixed Model analysis, using SAS (Version 9.3, SAS Institute Inc., Cary, N.C., 2008) according to the following statistical model:

$$Y_{ijk}=\mu+\alpha_i+b_j+\alpha(c)_{ik}+\varepsilon_{ijk}$$

where:
$Y_{ijk}$=a specific trait per experimental unit (replicate of 15 eggs)
$\mu$=overall mean for the specific trait
$\alpha_i$=fixed effect of treatment (i=1-4)
$b_j$=random effect of block/storage day (j=1-6)
$\alpha(c)_{ik}$=random nested effect of breeder pen within treatment (k=1-24)
$\varepsilon_{ijk}$=error term The nested effect of breeder pen within treatment was included in the model to correct for the number of experimental units of the broiler breeder treatment used. Due to the design of the experiment, a storage day effect was completely confounded with block (location in incubator) effect. Contrasts were used to compare treatment effects. The contrast descriptions are given below and the contrasts specifications to answer each question are shown in Table 18.
1) Was there a linear vitamin E effect?
2) Was there a quadratic vitamin E effect?
3) Was there a PPROVIOX 50 replacement effect?
4) Was the PROVIOX 50 replacement effect depended on dose?
5) Was there an additive effect of adding PROVIOX 50 on top of vitamin E?

TABLE 18

| Contrast Statements Used for Statistical Analysis | | | |
|---|---|---|---|
| Vit E dose 1 | Vit E dose 2 | PROVIOX dose 1 | PROVIOX dose 2 |
| 1) −1 | 1 | 0 | 0 |
| 2) −1 | −1 | 1 | 1 |

TABLE 18-continued

| Contrast Statements Used for Statistical Analysis | | | |
|---|---|---|---|
| Vit E dose 1 | Vit E dose 2 | PROVIOX dose 1 | PROVIOX dose 2 |
| 3) −1 | 1 | 1 | −1 |
| 4) −1 | 0 | 0 | 1 |

Figure 4:
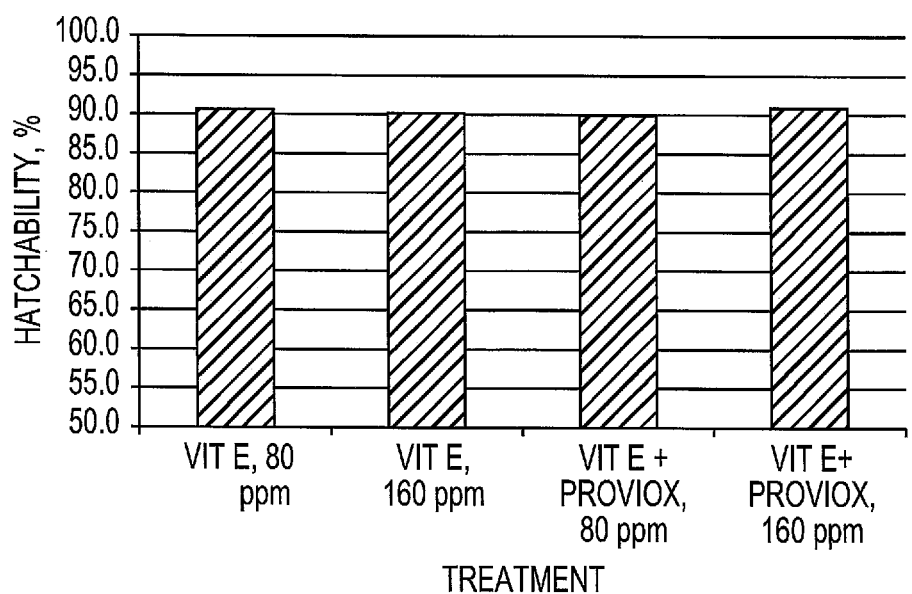
FIG. 4 is a graph of hatchability of total results based on broiler breeder treatment for Example 5.
Figure 5:
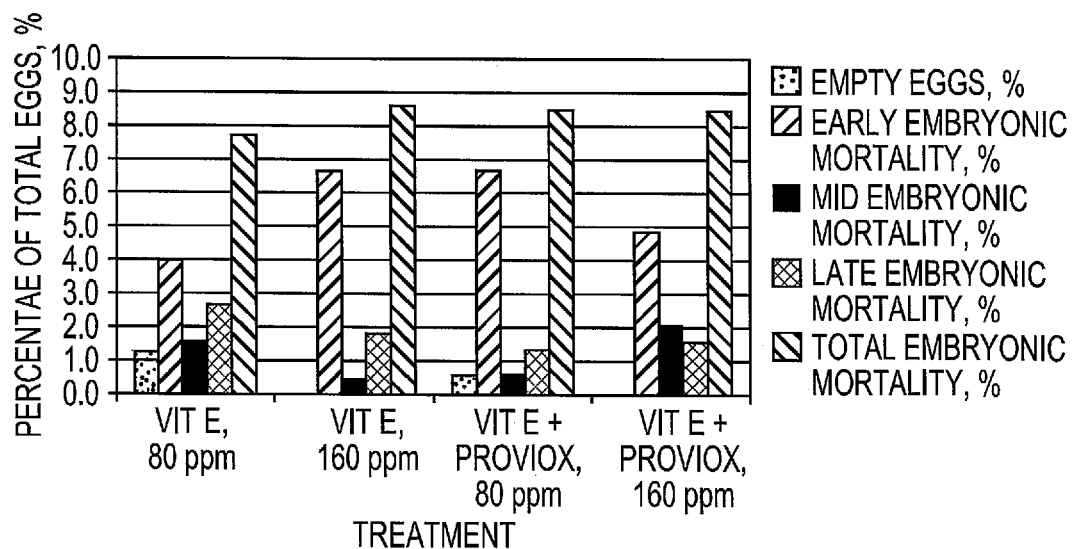
FIG. 5 is a graph of the percentage of empty eggs, early, mid, late, and total embryonic mortality based on broiler breeder treatment for Example 5.

Average egg weight at the start of the trial was 63.1 gram per egg. Average hatchability (90.4% of total) was above average compared to breeder standards for 38 week Ross breeders (87.2% of total). These results indicate that the average fertility and hatchability and the brooding process was good in the current experiment Candling results indicated a relatively high early embryonic mortality and a very low number of empty eggs (respectively 5.5 and 0.5% of total set eggs; Table 19), indicating that sperm production of the males was good. No significant differences on hatchability, empty eggs, early, mid or late embryonic mortality percentage were observed (FIGS. 4 and 5, Table 19).

TABLE 19

The Broiler Breeder Treatment Effects on Embryonic Mortality and Hatchability Data of Ross 308 Embryos

| Vitamin E equivalence (ppm) | Vit E Dose 1 80 | Vit E Dose 2 160 | Proviox 50% 80 | Proviox 50% 160 | Overall P-Value | Linear Vit E Effect | Quadratic Vit E Effect | Proviox Replacement Effect | Proviox Replacement Depended On Dose | Additive Effect Of Proviox Adding on Top |
|---|---|---|---|---|---|---|---|---|---|---|
| n | 24 | 24 | 24 | 24 | — | — | — | — | — | — |
| Hatchability of total, % | 90.6 | 90.2 | 89.9 | 90.9 | 0.974 | 0.994 | 0.659 | 0.988 | 0.669 | 0.898 |
| Hatchability of fertile, % | 91.8 | 90.2 | 90.4 | 90.9 | 0.898 | 0.803 | 0.548 | 0.831 | 0.522 | 0.692 |
| Empty eggs, % | 1.2 | 0.0 | 0.6 | 0.0 | 0.274 | 0.373 | 0.954 | 0.906 | 0.841 | 0.204 |
| Early Embryonic Mortality, % | 4.0 | 6.6 | 6.7 | 4.8 | 0.363 | 0.680 | 0.099 | 0.676 | 0.092 | 0.583 |
| Mid Embryonic Mortality, % | 1.6 | 0.5 | 0.6 | 2.1 | 0.125 | 0.432 | 0.030 | 0.569 | 0.023 | 0.600 |
| Late Embryonic Mortality, % | 2.7 | 1.8 | 1.3 | 1.6 | 0.423 | 0.666 | 0.364 | 0.210 | 0.418 | 0.226 |
| Total Embryonic Mortality, % | 7.7 | 8.6 | 8.5 | 8.5 | 0.978 | 0.907 | 0.790 | 0.841 | 0.775 | 0.740 |

Hatched chickens showed no significant differences in average and relative chick weight (Table 20). Furthermore, no treatment effects were found on several chick quality parameters (YFBM, chick length, and relative asymmetry). OXISELECT Superoxide Dismutase Activity Assay ("SOD") and OXISELECT Total Glutathione (GSSG/GSH) Assay ("GSSG") kits, available commercially from Cell Biolabs, Inc., San Diego, Calif., USA, were used to analyze chick livers. No significant effects were found upon the SOD and GSSG analysis of the liver. However, when comparing numerical differences it was found that partially replacing vitamin E by PROVIOX 50 at the low level (80 ppm vitamin E) increased antioxidant status of the embryos.

TABLE 20

The Broiler Breeder Treatment Effects on Embryonic Development
and Chick Quality Parameters at Hatch of Ross 308 Embryos

| Vitamin E equivalence (ppm) | Vit E Dose 1 80 | Vit E Dose 2 160 | Proviox 50% 80 | Proviox 50% 160 | Pooled SEM | Overall P-Value | Linear Vit E Effect | Quadratic Vit E Effect | Proviox Replacement Effect | Proviox Replacement Depended On Dose | Additive Effect Of Proviox On Top |
|---|---|---|---|---|---|---|---|---|---|---|---|
| n | 24 | 24 | 24 | 24 | — | — | — | — | — | — | — |
| Egg weight EQ, g | 62.9 | 63.0 | 63.3 | 63.1 | 0.3212 | 0.701 | 0.472 | 0.473 | 0.306 | 0.593 | 0.553 |
| Chick weight average, g | 43.8 | 43.7 | 44.1 | 43.6 | 0.2831 | 0.428 | 0.268 | 0.299 | 0.641 | 0.447 | 0.503 |
| Relative chick weight[1], % | 69.7 | 69.4 | 69.7 | 69.1 | 0.4038 | 0.255 | 0.377 | 0.430 | 0.655 | 0.571 | 0.103 |
| Chick weight dissected chicks, g | 42.8 | 43.6 | 43.8 | 43.0 | 0.5057 | 0.409 | 0.952 | 0.102 | 0.657 | 0.108 | 0.763 |
| Yolk weight, g | 4.2 | 4.2 | 4.2 | 4.0 | 0.3299 | 0.846 | 0.889 | 0.553 | 0.655 | 0.538 | 0.530 |
| Relative yolk weight[2], % | 9.7 | 9.4 | 9.5 | 9.2 | 0.6998 | 0.846 | 0.888 | 0.975 | 0.599 | 0.950 | 0.385 |
| Liver weight, g | 1.2 | 1.2 | 1.2 | 1.2 | 0.0361 | 0.708 | 0.816 | 0.544 | 0.677 | 0.591 | 0.337 |
| Relative liver weight[2], % | 2.8 | 2.7 | 2.7 | 2.9 | 0.0942 | 0.470 | 0.554 | 0.188 | 0.533 | 0.158 | 0.539 |
| YFBM[2], g | 39.6 | 40.6 | 40.5 | 40.1 | 0.4181 | 0.127 | 0.424 | 0.059 | 0.517 | 0.045 | 0.222 |
| Chick length, cm | 18.3 | 18.4 | 18.4 | 18.4 | 0.1534 | 0.802 | 0.895 | 0.846 | 0.431 | 0.872 | 0.344 |
| Relative asymmetry, % | 2.4 | 2.3 | 2.7 | 2.7 | 0.3456 | 0.760 | 0.384 | 0.848 | 0.300 | 0.990 | 0.557 |
| SOD units | 0.776 | 0.777 | 0.777 | 0.776 | 0.0010 | 0.663 | 0.981 | 0.227 | 0.945 | 0.241 | 0.836 |
| GSSG, □M | 4.27 | 4.48 | 4.69 | 4.56 | 1.010 | 0.688 | 0.667 | 0.432 | 0.331 | 0.505 | 0.424 |

[1]Expressed as percentage of egg weight at EO
[2]Expressed as percentage of chick weight
[3]Yolk free body mass No significant treatment effects were found on any of the parameters evaluated. Furthermore, no significant effects were found on hatched chicken parameters. No significant effects were found on liver enzyme analysis for SOD and GSSG. However, at the low vitamin E level, replacement seemed to be efficient in increasing antioxidant capacity of the embryo. It can be concluded that replacement up to 50% of the dietary vitamin E by PROVIOX 50 can be used to reduce total compound feed costs in these diets without compromising hatchability and fertility rates or hatched chicken quality, at least in the experimental period between 30-38 weeks of age.

Example 6—Grow Out of Chickens from Example 5

In this Example, the hatched chickens were grown till slaughter age and performance was evaluated. The objective of the current experiment was to evaluate the effect of broiler breeder diet with vitamin E compared to 50% replacement of vitamin E by PROVIOX 50 on offspring performance.

Four broiler breeder treatments were evaluated (Table 12). Hatched chickens from Example 5 were grown out resulting from the broiler breeder experiment of Example 4, where the breeders received a control diet, a high vitamin E diet, or a diet in which the vitamin E level (at both levels) was for 50% replaced by PROVIOX 50. In the current experiment the same basal diet was fed to all broilers. The experimental period was divided in a starter phase (0-14 days) and a grower phase (14-35 days). At 14 days of age, all birds changed to their grower diet until 35 days of age.

In advance of diet formulation, ingredients (corn and soybean meal) were reserved and analyzed for crude protein ("CP") (ISO 16634) and calcium (ISO 27085:2009; in duplicate) content at Provimi B.V. laboratory, Rotterdam, the Netherlands. In addition, corn was analyzed for phosphorus content (ISO 27085:2009; in duplicate) and soybean meal for potassium (ISO 27085:2009). Near-infrared reflectance spectroscopy analysis (ISO 12099) was applied to estimate dry matter ("DM"), crude fat, crude fiber, and crude ash content.

The starter and grower diet were produced by Research Diet Services (RDS, Wijk bij Duurstede, the Netherlands). Starter diets were pelleted at 2.5 mm and grower diets at 3 mm with steam addition (about 80° C.). Diets were formulated based on the analyzed ingredient values and to meet the nutrient requirements of broilers (Cargill, Incorporated CPN EMEA guidelines). The starter and grower diets contained 2,750 and 2,850 kcal AME broiler g·kg$^{-1}$ and 10.20 and 9.70 g·kg$^{-1}$ apparent fecal digestibly (AFD) lysine, respectively. Composition of the experimental starter and grower diets are provided in Table 21. Analyses of the diets are shown in Table 22.

TABLE 21

Ingredient and nutrient composition of the starter and grower diets

| Feeding Phase Feed Code | Starter BG1305-1 | Grower BG1305-10 |
|---|---|---|
| Ingredient Composition (%) | | |
| Corn | 45.58 | 47.20 |
| Wheat | 20.00 | 20.00 |
| Soybean Meal >48% | 28.87 | 26.71 |
| Limestone | 1.56 | 1.22 |
| Monocalciumphosphate | 1.35 | 1.14 |
| Broiler Premix 1%[1] | 1.00 | 1.00 |
| Fat, Animal | 0.41 | 1.48 |
| Fats/Oils, Soya Oil | 0.41 | 0.49 |

TABLE 21-continued

Ingredient and nutrient composition of the starter and grower diets

| Feeding Phase Feed Code | | Starter BG1305-1 | Grower BG1305-10 |
|---|---|---|---|
| | Sodiumbicarbonate | 0.253 | 0.186 |
| | Salt | 0.212 | 0.209 |
| | DL-Methionine | 0.199 | 0.184 |
| | L-Lysine HCI | 0.152 | 0.160 |
| | L-Threonine | 0.016 | 0.017 |
| Nutritional Composition (%) | | | |
| 1120ac | Crude Protein | 20.7 | 19.8 |
| 1130ac | Crude Fat | 3.3 | 4.4 |
| 1140 | Crude Fibre | 2.3 | 2.3 |
| 1150ac | Ash | 6.2 | 5.5 |
| 1110ac | DM | 88.7 | 88.8 |
| 1511ac | Ca | 0.97 | 0.80 |
| 1513ac | P | 0.67 | 0.61 |
| 1521ac | Na | 0.16 | 0.14 |
| 1522ac | K | 0.86 | 0.82 |
| 1523ac | Cl | 0.20 | 0.20 |
| 1530 | dEB | 233 | 214 |
| 3310 | Dig P Poultry | 0.393 | 0.349 |
| 3312 | Av P Poultry | 0.43 | 0.38 |
| 3110 | AME Poultry | 2931 | 3032 |
| 3112 | AME Poultry (FS-R) | 2969 | 3069 |
| 3130 | AME Broiler (CVB)[2] | 2750 | 2850 |
| 1210 | LYS | 1.182 | 1.125 |
| 1211 | MET | 0.509 | 0.482 |
| 1213 | SAA | 0.851 | 0.810 |
| 1214 | THR | 0.776 | 0.740 |
| 1215 | TRP | 0.244 | 0.231 |
| 1216 | ILE | 0.862 | 0.818 |
| 1218 | VAL | 0.960 | 0.915 |
| 1219 | ARG | 1.357 | 1.283 |
| 3240 | TFD LYSp[3] | 1.057 | 1.007 |
| 3241 | TFD METp | 0.477 | 0.451 |
| 3243 | TFD SAAp | 0.767 | 0.730 |
| 3244 | TFD THRp | 0.671 | 0.639 |
| 3245 | TFD TRPp | 0.215 | 0.203 |
| 3246 | TFD ILEp | 0.775 | 0.735 |
| 3248 | TFD VALp | 0.859 | 0.818 |
| 3249 | TFD ARGp | 1.242 | 1.174 |
| 3200 | AFD LYSp[4] | 1.020 | 0.970 |
| 3201 | AFD METp | 0.471 | 0.445 |
| 3203 | AFD SAAp | 0.745 | 0.708 |
| 3204 | AFD THRp | 0.643 | 0.611 |
| 3205 | AFD TRPp | 0.213 | 0.201 |
| 3206 | AFD ILEp | 0.749 | 0.710 |
| 3208 | AFDVALp | 0.816 | 0.776 |
| 3209 | AFD ARGp | 1.201 | 1.134 |
| 1327 | C18:2 | 1.374 | 1.528 |

[1]Supplied per kg starter diet. Vitamin A (retinyl-acetate), 12,000 IU; vitamin D3 (cholecalciferol), 5000 IU; vitamin E (DL-☐-tocopherol), 30 mg; vitamin K3 (menadione), 2.3 mg; vitamin B1 (thiamine), 1.0 mg; vitamin B2 (riboflavin), 4.5 mg; vitamin B6 (pyridoxine-HCL), 2.7 mg; vitamin B12 (cyanocobalamine), 20 ☐g; niacin, 40 mg; D-pantothenic acid, 9 mg; choline chloride, 500 mg; folic acid, 0.5 mg; biotin, 100 ☐g; FeSO4•H2O, 150 mg; CuSO4•5H2O, 40 mg; MO, 100 mg; nSo4•H2O, 145 mg; KJ, 2.0 mg; Na2SeO3, 0.56 mg; antioxidant (oxytrap PXN), 125 mg. Supplied per kg grower diet: vitamin A (retinyl-acetate), 10,000 IU; vitamin D3 (cholecalciferol), 2,000 IU; vitamin E (DL-☐-tocopherol), 20 mg; vitamin K3 (menadione), 2.3 mg; vitamin B1 (thiamine), 0.8 mg; vitamin B2 (riboflavin), 4.5 mg; vitamin B6 (pyridoxine-HCL), 1.9 mg; vitamin B12 (cyanocobal amine), 20 ☐g; niacine, 30 mg; D-pantothenic acid, 8 mg; choline chloride, 400 mg; folic acid, 0.5 mg; biotin, 50 ☐g; FeSO4•H2O, 150 mg; CuSO4•5H2O, 40 mg; MnO, 100 mg; ZnSo4•H2O, 145 mg; KJ, 1.9 mg; Na2SeO3, 0.50 mg; antioxidant (oxytrap PXN), 125 mg.

TABLE 22

Calculated and Analyzed Nutritional Composition of the Starter and Grower Diets.

| Diets | BG1305-1 | BG1305-10 |
|---|---|---|
| Calculated Nutrients, % | | |
| CP | 20.7 | 19.8 |
| Crude Fat | 3.28 | 4.44 |
| Crude Fibre | 2.31 | 2.27 |
| DM | 88.7 | 88.8 |
| Ca | 0.97 | 0.80 |
| P | 0.67 | 0.61 |
| Analyzed Nutrients 0.80 | | |
| CP | 21.5 | 20.2 |
| CP[1] | 20.6 | 19.1 |
| Crude Fat[1] | 3.40 | 4.3 |
| Crude Fiber[1] | 2.50 | 2.6 |
| DM[1] | 89.3 | 88.4 |
| Ca | 0.92 | 0.76 |
| P | 0.68 | 0.60 |
| % of Expected | | |
| CP | 103.7 | 102.1 |
| Crude Fat | 103.8 | 96.8 |
| Crude Fibre | 108.2 | 114.3 |
| DM | 100.7 | 99.6 |
| Ca | 95.0 | 95.2 |
| P | 102.3 | 98.5 |

[1]NIRS analysis

The experiment was performed in the broiler grower unit consisting of two rooms with 36 pens each. A total of 720 Ross 308 male 1-day-chickens, derived from 38-week-broiler breeders (Example 4) were randomly selected from the total number of hatched male chickens from Example 5. During selection the chickens were randomly selected from different experimental units in the hatchery, ensuring the experimental unit of the broiler breeder facility was kept intact, placing chickens from one experimental unit of the broiler breeder facility into one pen in the grow out facility. Each pen consisted of 30 chicks with an initial individual BW of 43.3±0.81 and 43.3±0.68 g for respectively unit A and unit B.

The pens (90×225 cm) had a raised floor, consisting of plastic wires covered with a 2-cm layer of wood shavings. Each pen was equipped with two sets of two adjustable nipple drinkers and a feeder that was positioned inside the pen for the first 13 days. From day 14 onwards, feed was supplied via a feeder trough in front of the pen. Both feed and water were provided ad libitum throughout the study. Continuous artificial lighting was maintained for 23 hours per day for the first three days of the experiment, 20 hours per day between days four and seven and 18 hours per day for the remainder of the experiment. Temperature, relative humidity, and ventilation were computer controlled with the temperature gradually decreasing by 0.5° C. per day the first thirteen days, from day fourteen until day 35 the temperature gradually decreased by approximately 0.4° from 34.0° C. on the day of arrival (1-day-chickens) to a final temperature of 20.4° C. at the end of the experiment (day 35).

The chickens were spray-vaccinated against Newcastle Disease (Poulvac NDW-vaccine, Intervet, Boxmeer, The Netherlands) at 15 days of age.

Individual bird weights were recorded at the start of the experiment (day 0) and at 14, 21, 28 and 35 days of age. In addition, feed consumption for each pen was recorded on the same day the birds were weighed. Based on calculated body weight gain and feed consumption, feed to gain ratio (F:G) was calculated as kg of feed consumed/kg of weight gain. Total feed consumption per pen was corrected for mortality, culling and outliers. The European Poultry Index was calculated using the following formula:

European Poultry Index=(Final Body Wt (g)×(100%−Mortality %))/((10×period in days)overall FCR)

The European Poultry Index excluding mortality was calculated using the following formula:

European Poultry Index=(Final Body Wt (g)×100)/((10×period in days)×overall FCR)

All data were subjected to the MIXED MODEL procedure in SAS (Version 9.3, SAS Institute Inc., Cary, N.C., USA) according to the following statistical model:

$$Y_{ij} = \mu + \alpha_i + b_j + \varepsilon_{ij}$$

where:
$Y_{ij}$=a specific trait measured for each experimental unit
$\mu$=overall mean for the specific trait
$\alpha_i$=fixed effect of broiler breeder treatment (i=1-4)
$b_j$=random block effect (j=1-6)
$e_{ij}$=residual error term Contrasts were used to compare treatment effects. The contrast descriptions are given below and the contrasts specifications to answer each question are shown in Table 23.
1) Was there a linear vitamin E effect?
2) Was there a PROVIOX 50 replacement effect?
3) Was the PROVIOX 50 replacement effect depended on dose?
4) Was there an additive effect of adding PROVIOX 50 on top of vitamin E?

TABLE 23

Contrast Statements Used for Statistical Analysis.

| | Vit E dose 1 | Vit E dose 2 | PROVIOX dose 1 | PROVIOX dose 2 |
|---|---|---|---|---|
| 1) | −1 | 1 | 0 | 0 |
| 2) | −1 | −1 | 1 | 1 |
| 3) | −1 | 1 | 1 | −1 |
| 4) | −1 | 0 | 0 | 1 |

Nutritional composition of the diets was in line with the expected values (Table 22). Observed health status of the birds was good throughout the experiment. Mortality, including culling, reached 1.4%, which is low compared with practical levels (3 to 4%) and with previous broiler grower studies (mean 2012: 4.5%).

Surprisingly, offspring final bodyweight, average daily gain, and feed intake were significantly higher when vitamin E was partially replaced by PPROVIOX 50 in the broiler breeder diet (respectively 4.2, 4.8 and 3.8%), this was independent of inclusion level, as shown in Table 24.

TABLE 24

Broiler breeder treatment effects on offspring mortality, BW, European poultry index (EPI), average daily gain (ADG), average daily feed intake (ADFI), and feed to gain ratio (F:G)

| | Vit E Dose 1 | Vit E Dose 2 | Proviox Dose 1 | Proviox Dose 2 | Pooled SEM | P-value | Linear vit E effect | Proviox replacement effect | Replacement depended on dose | Additive effect of Proviox on top |
|---|---|---|---|---|---|---|---|---|---|---|
| n[1] | 6 | 6 | 6 | 6 | — | — | — | — | — | — |
| Mortality, % | 2.9 | 0.9 | 2.4 | 3.4 | — | 0.469 | ns | ns | ns | ns |
| BW 0 d, g | 43.5 | 42.9 | 43.5 | 43.2 | 0.30 | 0.518 | ns | ns | ns | ns |
| BW 35 d, g[2] | 2206 | 2133 | 2276 | 2245 | 46.90 | 0.094 | ns | ** | ns | ns |
| CV 35 d, % | 11.5 | 11.8 | 12.0 | 10.6 | 1.06 | 0.712 | ns | ns | ns | ns |
| EPI[3] | 403 | 392 | 414 | 419 | 8.47 | 0.009 | ns | *** | ns | * |
| EPI excl mortality[3] | 419 | 396 | 427 | 434 | 11.15 | 0.011 | ** | *** | * | ns |
| ADG 0-14 d, g | 27.3 | 26.7 | 28.5 | 28.2 | 0.81 | 0.241 | ns | * | ns | ns |
| ADG 14-21 d, g[4] | 59.5 | 53.3 | 60.4 | 63.1 | 4.04 | 0.097 | ns | * | ns | ns |
| ADG 21-28 d, g[4] | 83.0 | 84.3 | 88.6 | 88.2 | 2.71 | 0.167 | ns | ** | ns | * |
| ADG 28-35 d, g[3] | 113.2 | 107.5 | 113.0 | 111.5 | 3.44 | 0.493 | ns | ns | ns | ns |
| ADG 0-35 d, g[3] | 62.3 | 59.7 | 63.8 | 64.1 | 1.50 | 0.017 | * | *** | ns | ns |
| ADG 14-35 d, g[3] | 84.7 | 81.7 | 87.3 | 86.2 | 1.94 | 0.146 | ns | * | ns | ns |
| ADFI 0-14 d, g | 33.5 | 33.0 | 35.3 | 35.0 | 0.90 | 0.121 | ns | ** | ns | ns |
| ADFI 14-21 d, g | 89.9 | 83.9 | 91.6 | 93.8 | 4.14 | 0.069 | ns | ** | ns | ns |
| ADFI 21-28 d, g | 131.9 | 133.0 | 138.1 | 135.6 | 3.46 | 0.300 | ns | * | ns | ns |
| ADFI 28-35 d, g[5] | 183.0 | 176.1 | 185.9 | 180.6 | 3.60 | 0.179 | ns | ns | ns | ns |
| ADFI 0-35 d, g[5] | 94.3 | 91.8 | 97.2 | 96.0 | 1.86 | 0.029 | ns | ** | ns | ns |
| ADFI 14-35 d, g[5] | 134.9 | 131.0 | 138.5 | 136.7 | 2.64 | 0.043 | ns | ** | ns | ns |
| F:G 0-14 d | 1.228 | 1.236 | 1.237 | 1.242 | 0.008 | 0.696 | ns | ns | ns | ns |
| F:G 14-21 d | 1.524 | 1.606 | 1.526 | 1.491 | 0.047 | 0.177 | ns | ns | ns | ns |
| F:G 21-28 d[4] | 1.589 | 1.580 | 1.561 | 1.547 | 0.023 | 0.458 | ns | ns | ns | ns |
| F:G 28-35 d[3] | 1.614 | 1.641 | 1.647 | 1.641 | 0.029 | 0.827 | ns | ns | ns | ns |
| F:G 0-35 d[3] | 1.517 | 1.537 | 1.524 | 1.508 | 0.009 | 0.022 | ** | * | *** | ns |
| F:G 14-35 d[3] | 1.579 | 1.604 | 1.587 | 1.564 | 0.012 | 0.017 | ** | ** | *** | ns |

TABLE 24-continued

Broiler breeder treatment effects on offspring mortality, BW,
European poultry index (EPI), average daily gain (ADG), average daily feed
intake (ADFI), and feed to gain ratio (F:G)

|  | Vit E Dose 1 | Vit E Dose 2 | Proviox Dose 1 | Proviox Dose 2 | Pooled SEM | P-value | Contrasts | | | |
|---|---|---|---|---|---|---|---|---|---|---|
|  |  |  |  |  |  |  | Linear vit E effect | Proviox replacement effect | Replacement depended on dose | Additive effect of Proviox on top |
| F:G corrected for BW[5,6] | 1.507 | 1.546 | 1.504 | 1.485 | 0.016 | 0.007 | ** | *** | ** | ns |

Mortality = percentage of total mortality and culling relative to the number of birds at day 0;
EPI = ((Final Body Wt(g) xx 100% – Mortality %))/((10 × period in days) × overall FCR));
EPI excl. mortality = ((Final Body Wt (g) × 100%)/((10 × period in days) × overall FCR));
F; G = g feed intake:g gain.
[1]Individual pen with 30 birds.
[2]n = 5 for vit E dose 1 and Proviox dose 2.
[3]n = 5 for vit E dose 1, and n = 4 for Proviox dose 2.
[4]n = 5 Proviox dose 2.
[5]n = 5 vor vit E dose 1.
[7]F:G corrected for BW = F:G corrected to 2,176 gram bodyweight at 35 d age. Correction of –0.02 for each 100 g extra weight.
NS = P > 0.10;
* = P < 0.10;
** = P < 0.01.

Figure 6:
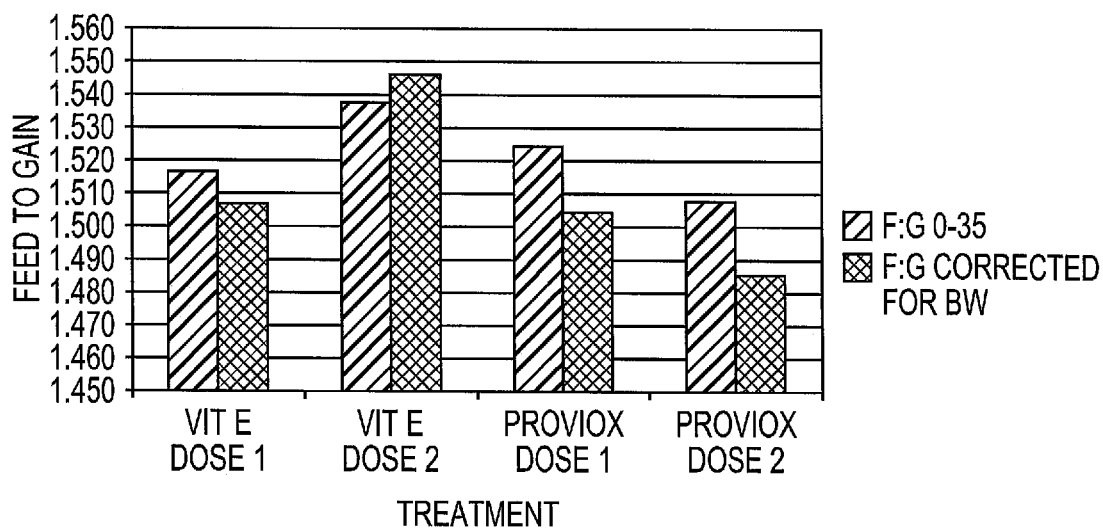
FIG. 6 is a graph showing broiler breeder treatment effects on offspring overall feed to gain and corrected for final bodyweight feed to gain for Example 6.

Referring to Table 24, feed to gain improvement was significantly better at the high inclusion level replacement, where replacement lead to a 1.9% more efficient use of feed. This effect was even more pronounced when corrected for final bodyweight (3.9% more efficient offspring; FIG. 6). Overall feed to gain was significantly (1.4%) worse for the high vitamin E treatment compared to the low vitamin E treatment. Also this effect was more pronounced when corrected for final bodyweight (2.6%).

It is unclear why the higher level of vitamin E in the broiler breeder diet would result in less efficient offspring. Published research on broiler breeder diets following offspring performance mainly report used vitamin E levels between 0 and 100 ppm, the high inclusion level in the current study was 160 ppm. In practice, even higher levels are sometimes used, however, focus remains on number of hatched chickens per breeder and less, or even none, on offspring performance. A possible explanation for the lower offspring performance could be that vitamin E was overdosed in the breeder diet, thereby programming the offspring to be less efficient on vitamin E absorption, or less efficient in antioxidant defense. By supplying PROVIOX 50 in the broiler breeder diet, other antioxidant sources are available for the offspring (water soluble sources). This might increase the antioxidant status of the offspring, thereby enabling them to grow more and more efficient.

Results of the current study show that increasing vitamin E in the broiler breeder diet from 80 to 160 ppm results in less efficient offspring. It was surprisingly found that partially replacing vitamin E by 50% with PROVIOX 50 resulted in a significantly higher overall growth and feed intake (independent of dose), and to more efficient offspring at the high inclusion level.

Example 7—Partial Replacement of Vitamin E in Broiler Breeder Diets

All breeders received the same diet during the pre-experimental period (49-56 weeks of age). During the experimental period, breeders received the control diet, or a diet where 50% of the vitamin E was replaced by PROVIOX 50 (see Table 25).

TABLE 25

Experimental Design Broiler Breeder Treatments

| Treatment | Vitamin E 50 (ppm) | PROVIOX 50 (ppm)* |
|---|---|---|
| Control | 160 | — |
| PROVIOX | 80 | 80 |

*Vitamin E 50 equivalence

Figure 7:
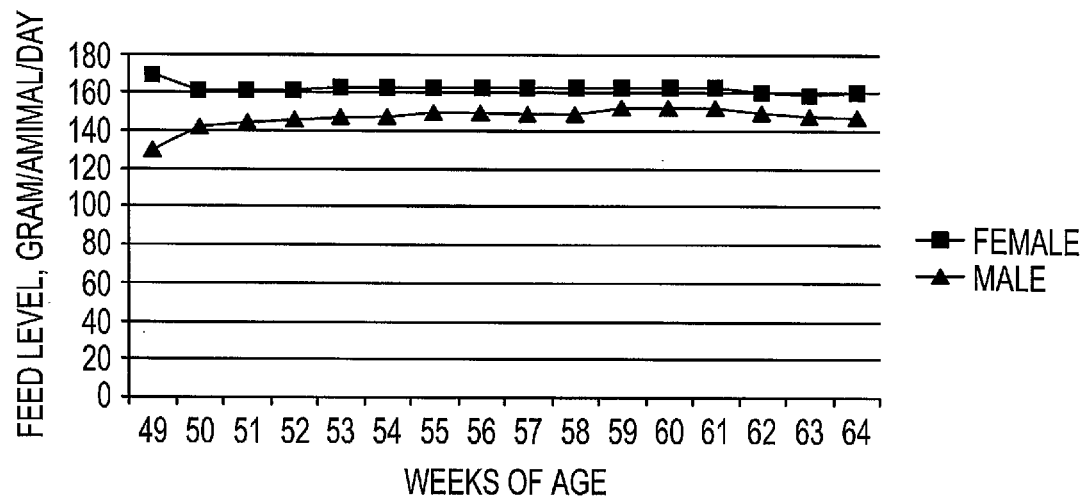
FIG. 7 is a graph showing provided feed amounts during the pre-experimental period (49-56 weeks) and experimental period (56-64 weeks) for Example 7.

In total, there were twelve floor pens with approximately thirty breeder females and three males per pen used. The experimental period lasted eight weeks; the breeders received a lay phase diet during the entire experimental period. Feed and water were restricted. Feed amount depended on average body weight development. Feeding levels during the pre-experimental period and experimental period are shown in FIG. 7. Water was provided for two hours a day, crops were checked regularly to ensure the correct amount of water was provided.

In advance of diet formulation, batches of soybean meal, wheat middlings, coarsely ground maize, and wheat were reserved and wet chemically analyzed for crude protein content, dry matter, calcium, and phosphorus. In addition, soybean meal was analyzed for potassium content and wheat middlings were wet chemically analyzed for crude fiber, potassium, and starch. Near-infrared reflectance spectroscopy ("NIRS") analysis was used to predict crude ash, crude fat, crude fiber, moisture, and to crosscheck crude protein. The formulation of diets was based on the analyzed nutrient content of the reserved ingredients. One batch of feed was used for the entire experimental period.

A basal diet (corn—soybean meal—wheat and wheat middlings) was formulated based on Provimi nutrient recommendations for broiler breeders. Diet formulations were optimized according to the Provimi Nutrient Code ("PNC") system. Different male and female diets were produced, though using the same experimental design and premix composition. This was done to be able to feed the males according to their nutritional needs (lower for crude protein, energy, and calcium requirements). Compositions of the experimental diets and analyses are shown in Tables 26 and 27, respectively. Diets were produced by Research Diet Services (RDS, Wijk bij Duurstede, the Netherlands). Diets were produced separately, using one basal diet batch for the female diets and one basal diet batch for the male diets. Diets were produced as mash.

TABLE 26

Ingredient and Nutritional Composition of the Experimental Diets

| | Feedcode | | | | | |
|---|---|---|---|---|---|---|
| | LT1304-Pre-1 | LT1304-Pre-2 | LT1304-1 | LT1304-2 | LT1304-3 | LT1304-4 |
| | | | Treatment | | | |
| | — | — | 1 | 2 | 1 | 2 |
| | | | Sex | | | |
| | Female | Male | Female | Female | Male | Male |
| | | | Diet Form | | | |
| | Mash | Mash | Mash | Mash | Mash | Mash |
| | Ingredient Composition (%) | | | | | |
| Corn | 44.8 | 38.2 | 44.98 | 44.98 | 40.08 | 40.08 |
| Wheat | 20.0 | 20.0 | 20.0 | 20.0 | 20.0 | 20.0 |
| Soybean meal | 13.3 | 6.6 | 14.7 | 14.7 | 6.6 | 6.6 |
| Wheat middlings | 10.0 | 30.0 | 9.1 | 9.1 | 28.0 | 28.0 |
| Limestone Coarse | 5.6 | — | 5.2 | 5.2 | | 0.0 |
| Limestone Fine | 2.8 | 1.7 | 2.6 | 2.6 | 1.7 | 1.7 |
| Monocalcium - Phosphate | 1.1 | 1.0 | 1.1 | 1.1 | 1.3 | 1.3 |
| Soya Oil | 1.0 | 1.0 | 1.0 | 1.0 | 1.0 | 1.0 |
| Premix[1] (1%) | 1.0 | 1.0 | 1.0 | 1.0 | 1.0 | 1.0 |
| Salt | 0.21 | 0.17 | 0.21 | 0.21 | 0.22 | 0.22 |
| Na-Bicarbonate | 0.06 | 0.16 | 0.062 | 0.062 | 0.092 | 0.092 |
| L-Lysine HCL | 0.072 | 0.024 | 0.060 | 0.060 | 0.009 | 0.009 |
| DL-Methionine | 0.118 | 0.039 | 0.123 | 0.123 | 0.047 | 0.047 |
| Vitamin E50 | — | — | 0.016 | 0.008 | 0.016 | 0.008 |
| PROVIOX 50 | — | — | — | 0.008 | — | 0.008 |
| Nutritional Composition (%) - based on Provimi Nutrient Code System | | | | | | |
| 1120 Crude Protein | 14.5 | 13.5 | 14.5 | 14.5 | 13.0 | 13.0 |
| 1130 Crude Fat | 3.43 | 3.87 | 3.59 | 3.59 | 3.88 | 3.88 |
| 1140 Crude Fibre | 2.58 | 3.91 | 2.80 | 2.80 | 4.06 | 4.06 |
| 1150 Ash | 11.9 | 5.6 | 11.3 | 11.3 | 5.7 | 5.7 |
| 1110 Dry Matter | 88.4 | 87.7 | 88.1 | 88.1 | 87.2 | 87.2 |
| 1511 Calcium | 3.43 | 0.90 | 3.20 | 3.20 | 0.90 | 0.90 |
| 1513 Phosphorous P | 0.59 | 0.72 | 0.59 | 0.59 | 0.75 | 0.75 |
| 3312 Av. P | 0.35 | 0.35 | 0.35 | 0.35 | 0.40 | 0.40 |
| 3311 Dig. Players | 0.33 | 0.35 | 0.33 | 0.33 | 0.39 | 0.39 |
| 1521 Sodium | 0.14 | 0.14 | 0.14 | 0.14 | 0.14 | 0.14 |
| 1522 Potassium | 0.63 | 0.68 | 0.64 | 0.64 | 0.67 | 0.67 |
| 1523 Chloride | 0.18 | 0.16 | 0.18 | 0.18 | 0.18 | 0.18 |
| 1530 dEB | 171 | 190 | 174 | 174 | 180 | 180 |
| 3110 ME Poultry | 2712 | 2730 | 2710 | 2710 | 2707 | 2707 |
| 3112 ME Poultry (FS-R) | 2733 | 2735 | 2741 | 2741 | 2737 | 2737 |
| 3120 ME Layer | 2750 | 2772 | 2750 | 2750 | 2750 | 2750 |
| 1210 LYS | .0705 | 0.563 | 0.704 | 0.704 | 0.530 | 0.530 |
| 1211 MET | 0.348 | 0.259 | 0.352 | 0.352 | 0.260 | 0.260 |
| 1213 SAA | 0.611 | 0.524 | 0.613 | 0.613 | 0.515 | 0.515 |
| 1214 THR | 0.513 | 0.462 | 0.516 | 0.516 | 0.446 | 0.446 |
| 1215 TRP | 0.165 | 0.158 | 0.165 | 0.165 | 0.151 | 0.151 |
| 1216 ILE | 0.564 | 0.488 | 0.568 | 0.568 | 0.470 | 0.470 |
| 1218 VAL | 0.667 | 0.620 | 0.669 | 0.669 | 0.598 | 0.598 |
| 1219 ARG | 0.886 | 0.809 | 0.892 | 0.892 | 0.776 | 0.776 |
| 3200 AFD LYSp | 0.580 | 0.440 | 0.580 | 0.580 | 0.410 | 0.410 |
| 3201 AFD METp | 0.315 | 0.222 | 0.319 | 0.319 | 0.224 | 0.224 |
| 3203 AFD SAADp | 0.520 | 0.429 | 0.523 | 0.523 | 0.423 | 0.423 |
| 3204 AFD THRp | 0.404 | 0.349 | 0.408 | 0.408 | 0.338 | 0.338 |
| 3205 AFD TRPp | 0.139 | 0.130 | 0.140 | 0.140 | 0.124 | 0.124 |
| 3206 AFD ILEp | 0.478 | 0.402 | 0.482 | 0.482 | 0.388 | 0.388 |
| 3208 AFD VALp | 0.549 | 0.497 | 0.552 | 0.552 | 0.479 | 0.479 |
| 3209 AFD ARGp | 0.774 | 0.701 | 0.781 | 0.781 | 0.673 | 0.673 |
| 3240 TFD LYSp | 0.616 | 0.470 | 0.616 | 0.616 | 0.440 | 0.440 |
| 3241 TFD METp | 0.324 | 0.230 | 0.327 | 0.327 | 0.232 | 0.232 |
| 3243 TFD SAAp | 0.547 | 0.449 | 0.549 | 0.549 | 0.444 | 0.444 |
| 3244 TFD THRp | 0.436 | 0.380 | 0.439 | 0.439 | 0.367 | 0.367 |
| 3245 TFD TRPp | 0.143 | 0.133 | 0.143 | 0.143 | 0.127 | 0.127 |

TABLE 26-continued

Ingredient and Nutritional Composition of the Experimental Diets

| | Feedcode | | | | | |
|---|---|---|---|---|---|---|
| | LT1304-Pre-1 | LT1304-Pre-2 | LT1304-1 | LT1304-2 | LT1304-3 | LT1304-4 |
| | | | Treatment | | | |
| | — | — | 1 | 2 | 1 | 2 |
| | | | Sex | | | |
| | Female | Male | Female | Female | Male | Male |
| | | | Diet Form | | | |
| | Mash | Mash | Mash | Mash | Mash | Mash |
| 3246 TFD ILEp | 0.505 | 0.427 | 0.509 | 0.509 | 0.412 | 0.412 |
| 3248 TFD VALp | 0.590 | 0.529 | 0.592 | 0.592 | 0.511 | 0.511 |
| 3249 TFD ARGp | 0.808 | 0.730 | 0.815 | 0.815 | 0.700 | 0.700 |
| 1327 C18:2 | 1.62 | 1.78 | 1.70 | 1.70 | 1.80 | 1.80 |
| Vitamin E equivalent (IU) | 80.00 | 80.00 | 80.00 | 80.00 | 80.00 | 80.00 |

[1]Supplied per kg diet Lay phase: riboflavin, 6.0 mg; niacinamide, 30 mg; D-pantothenic acid, 9 mg; choline chloride, 350 mg; DL-α-tocopherol, - IU; menadione, 2.5 mg; retinyl-acetate, 12500 IU; cholecalciferol, 2500 IU; biotin, 100 µg; folic acid, 1.0 mg; Thiamine, 1.0 mg; pyridoxine-HCI, 2.5 mg; cyanocobalamine, 25 µg; FeSO4•H2O, 147 mg; MnO2, 114 mg; CuSO4, 40 mg; ZnSo4•H2O, 206 mg; Na2SeO3, 0.88 mg; KJ, 2.6 mg; antioxidant (Oxytrap PXN), - mg

TABLE 27

Analyzed Nutritional Composition of the Experimental Diets

| | Feedcode | | | | | |
|---|---|---|---|---|---|---|
| | LT 1304-Pre-1 | LT 1304-Pre-2 | LT 1304-1 | LT 1304-2 | LT 1304-3 | LT 1304-4 |
| | Calculated Nutrients, % | | | | | |
| Crude Protein | 14.5 | 13.5 | 14.5 | 14.5 | 13.0 | 13.0 |
| Crude Fat | 3.4 | 3.9 | 3.6 | 3.6 | 3.9 | 3.9 |
| Crude Fibre | 2.6 | 3.9 | 2.8 | 2.8 | 4.1 | 4.1 |
| Dry Matter | 88.4 | 87.7 | 88.1 | 88.1 | 87.2 | 87.2 |
| Ca | 3.43 | 0.90 | 3.20 | 3.20 | 0.90 | 0.90 |
| P | 0.59 | 0.72 | 0.59 | 0.59 | 0.75 | 0.75 |
| | Analysed Nutrients | | | | | |
| Crude Protein | 14.7 | 13.7 | 14.9 | 14.9 | 13.4 | 13.2 |
| Crude Protein (NIRS) | 14.7 | 13.7 | 14.8 | 15.0 | 13.0 | 13.2 |
| Crude Fat (NIRS) | 3.2 | 4.1 | 3.5 | 3.4 | 3.8 | 3.8 |
| Crude Fibre (NIRS) | 2.8 | 4.5 | 3.1 | 2.9 | 4.2 | 4.4 |
| Moisture (NIRS) | 11.8 | 12.1 | 11.9 | 12.0 | 12.4 | 12.4 |
| Dry Matter | 88.2 | 87.9 | 88.1 | 88.0 | 87.6 | 87.6 |
| Ca | 3.62 | 1.02 | 3.40 | 3.42 | 0.94 | 0.92 |
| P | 0.65 | 0.79 | 0.65 | 0.62 | 0.80 | 0.82 |
| | % of expected | | | | | |
| Crude Protein | 101 | 101 | 102 | 103 | 102 | 102 |
| Crude Fat | 93 | 106 | 97 | 95 | 98 | 98 |
| Crude Fibre | 109 | 115 | 111 | 104 | 103 | 108 |
| Dry Matter | 100 | 100 | 100 | 100 | 100 | 100 |
| Ca | 106 | 113 | 106 | 107 | 104 | 102 |
| P | 110 | 110 | 109 | 104 | 106 | 109 |

A total of 730 female and 92 male Ross 308 19-week-old breeders were purchased via a commercial breeding organization (Pluvita B.V., Apeldoorn, The Netherlands). On arrival (at the start of the pre-experiment period), the males and females were randomly assigned to the floor pens (3-4 males and 30-31 females per pen). Breeders were reallocated at the start of the laying period (30 females and 3 males per pen). Remaining healthy males were placed in a spare pen, while remaining females were culled. Animals were not reallocated at the start of the following (pre-) experimental periods.

Throughout the experiment, breeders were housed in broiler breeder floor pens (2.60×2.40 m) on litter (flax). Each pen was equipped with one automatic water drinker adjustable in height. The feed for the females was supplied via two feed bowls on the raised slatted floor; the feed for the males was supplied via a feeder through on the other side of the pen.

Breeders were light stimulated during the first pre-experimental period according to breed standards. During the experimental period, day length was set for 15 hours a day. Temperature and ventilation were computer controlled.

Temperature was set to 20° C. for the complete period. Room temperature was recorded continuously throughout the experiment using a data logger placed inside the facility. Individual bird weights were recorded at 49, 55, 60, and 64 weeks of age. At 51, 53, 58, and 62 weeks of age, 50% of the females were weighed and all males, and at the remaining weeks, only the first four pens were weighed to determine proper weight development. Feed amount provided was recorded on a daily basis. Egg production and egg quality data were recorded on a daily basis. Laying % was calculated as number of eggs produced per pen divided by the number of bird days of the experimental period. Egg mass production per pen per week was calculated as laying % (including second class eggs) times average egg weight of the pen. Average egg weight was determined per pen once a week. Second-class eggs were divided into dirty eggs, broken eggs, shell-less eggs, double-yolk eggs, floor eggs, and remaining second-class eggs. Mortality was checked every day; dead animals were not replaced during the experimental period.

Statistics

Statistics were performed according to the Provimi Standards for Hypothesis testing and Means Separation, using ANOVA (revision 1.3). For comparison of the different treatments all parameters were subjected to the MIXED MODEL procedure using SAS (Version 9.2, SAS Institute Inc., Cary, N.C., 2008) according to the following statistical model:

$$Y_{ij} = \mu + \alpha_i + b_j + \varepsilon_{ij}$$

where:

$Y_{ij}$ = a specific trait per experimental unit (pen)

$\mu$ = overall mean for the specific trait $\alpha_i$ = fixed treatment effect (i=1 or 2)

$b_j$ = random block effect (j=1, 2, . . . , 6)

$\varepsilon_{ij}$ = error term

Contrasts were used to compare treatment effects. The contrast description is given below and the contrasts specification to answer the question is shown in Table 28.

1) Was there a PROVIOX 50 effect?

TABLE 28

Contrast Statement Used for Statistical Analysis

|  | Control | PROVIOX |
|---|---|---|
| 1) | −1 | 1 |

Nutritional composition of the diets was in line with the expected values as shown in Table 27. Observed health status of the birds was good throughout the experiment. Mortality, including culling, reached 6.7%, which is average compared to breeding standards (total mortality and culling during a 40 week laying period 8%). Technical performance was in line with breeder standards of Ross 308. Variation within treatments (LSD), expressed as a percentage of average bird performance, was for the overall experimental period 13.0% and 1.6% for respectively laying percentage and egg weight.

No significant treatment or carry-over effects of treatments were found on any of the performance data for the pre-experimental period (data not shown). No significant effects of any of the treatments were found on laying percentage compared to the control treatment, as shown in Table 29.

TABLE 29

Technical Results of Breeders Fed the Experimental Diets

|  | Control | PROVIOX | Pooled SEM | Overal P-value | PROVIOX effect |
|---|---|---|---|---|---|
| n | 6 | 6 | — | — | — |
| Laying percentage 56-64 wks, % | 50.4 | 54.8 | 2.2122 | 0.458 | 0.193 |
| Laying perc $1^{st}$ choice 56-64 wks, % | 45.1 | 49.0 | 2.4724 | 0.600 | 0.241 |
| Second Choice Eggs |  |  |  |  |  |
| Broken eggs 56-64 wks, % | 1.5 | 0.8 | 0.4942 | 0.662 | 0.277 |
| Dirty eggs 56-64 wks, % | 2.1 | 1.8 | 0.2878 | 0.184 | 0.551 |
| Shell less eggs 56-64 wks, % | 0.0 | 0.1 | 0.0908 | 0.371 | 0.936 |
| Double yolk eggs 56-64 wks, % | 0.2 | 0.1 | 0.0720 | 0.650 | 0.469 |
| Floor eggs 56-64 wks, % | 0.4 | 1.7 | 1.0741 | 0.708 | 0.382 |
| Remainder 56-64 wks, % | 1.0 | 1.3 | 0.1897 | 0.750 | 0.312 |
| Egg weight 56-64 wks, g | 71.3 | 71.9 | 0.3499 | 0.385 | 0.294 |
| Eggmass 56-64 wks, g/h/d | 35.9 | 39.4 | 1.5316 | 0.401 | 0.134 |
| Bodyweight 56 wks, kg | 4.29 | 4.25 | 0.0403 | 0.175 | 0.433 |
| Bodyweight 64 wks, kg | 4.45 | 4.37 | 0.0442 | 0.066 | 0.237 |
| CV bodyweight 56 wk, % | 9.4 | 11.3 | 0.6126 | 0.115 | 0.057 |
| CV bodyweight 64 wk, % | 10.1 | 11.3 | 0.6111 | 0.372 | 0.211 |

Figure 8:
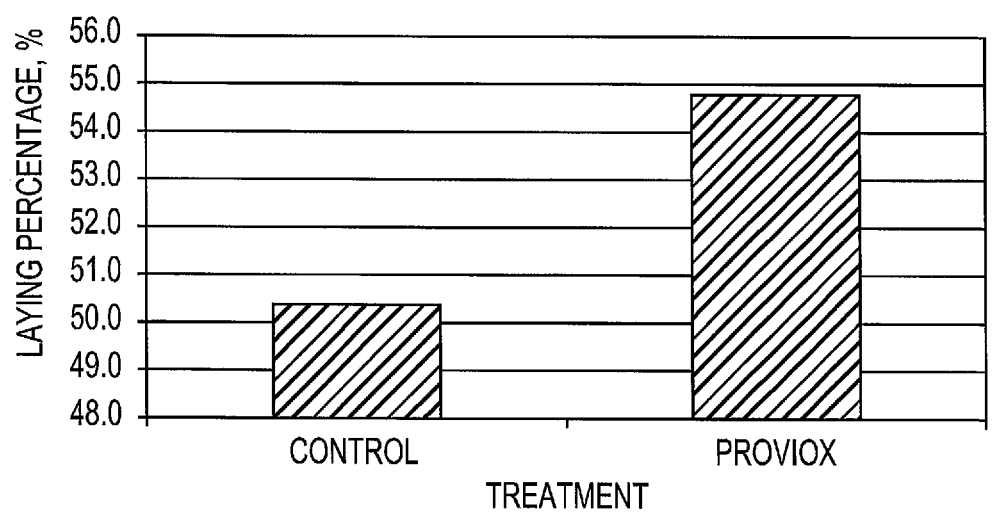
FIG. 8 is a graph showing the average laying percentage for breeders having various diets during the experimental period (56-64 weeks) for Example 7.

However, as shown in FIG. 8, when using PROVIOX 50 in the breeder diet, the laying percentage increased numerically by 8.8% compared to the control diet. For the overall experimental period, no significant effects were found on egg weight, which is in accord with previous studies.

Referring to Table 30, relative egg shell weight significantly increased by 3.8% when vitamin E was partially replaced (50%) by PROVIOX 50. This also relates to the numerical improvement of the egg breaking strength (7.9%). Numerically there were also 50% fewer broken eggs in the experimental period when vitamin E was partially replaced by PROVIOX 50.

TABLE 30

Egg Parameter Results of Breeders Fed the Experimental Diets

|  | Control | PROVIOX | Pooled SEM | Overal P-value | PROVIOX effect |
|---|---|---|---|---|---|
| n | 6 | 6 | — | — | — |
| Break strength, N | 33.7 | 36.3 | 1.2540 | 0.492 | 0.183 |

TABLE 30-continued

Egg Parameter Results of Breeders Fed the Experimental Diets

| | Control | PROVIOX | Pooled SEM | Overal P-value | PROVIOX effect |
|---|---|---|---|---|---|
| Albumen height, cm | 6.66 | 6.39 | 0.2863 | 0.002 | 0.298 |
| Egg weight, g | 70.8 | 72.2 | 0.6862 | 0.118 | 0.152 |
| Egg white weight, g | 36.7 | 37.9 | 0.8763 | 0.794 | 0.348 |
| Egg yolk weight, g | 23.7 | 23.7 | 0.3320 | 0.778 | 0.956 |
| Egg shell weight, g | 6.27 | 6.64 | 0.0832 | 0.039 | 0.008 |
| Relative egg white weight, % | 51.4 | 52.6 | 1.0871 | 0.790 | 0.409 |
| Relative egg yolk weight, % | 33.7 | 33.3 | 0.3373 | 0.285 | 0.541 |
| Relative egg shell weight, % | 8.89 | 9.23 | 0.0883 | 0.082 | 0.031 |
| Colour fan | 7.72 | 7.85 | 0.1849 | <.0001 | 0.580 |
| Minolta L 62 wks | 52.6 | 52.0 | 0.3665 | <.0001 | 0.194 |
| Minolta a 62 wks | 1.24 | 1.19 | 0.2461 | <.0001 | 0.820 |
| Minolta b 62 wks | 38.4 | 37.9 | 0.4640 | <.0001 | 0.209 |
| Minolta L 64 wks | 51.9 | 52.4 | 0.2602 | <.0001 | 0.194 |
| Minolta a 64 wks | 0.92 | 0.90 | 0.2513 | <.0001 | 0.944 |
| Minolta b 64 wks | 37.2 | 37.3 | 0.4207 | <.0001 | 0.865 |

Laying percentage numerically increased by 8.8% when vitamin E was partially replaced (50%) by PROVIOX 50. No significant effects were found for the overall average egg weight. Relative egg shell weight increased by 3.8% when vitamin E was partially replaced (50%) by PROVIOX 50; this also relates to the numerical improvement of the egg breaking strength (7.9%).

Example 8—Chicken Production from Eggs of Example 7

For a period of eleven days, eggs were collected from the broiler breeder flock of Example 7. They were stored based on breeder pen and storage day. All eggs were incubated until hatch. The eggs were distributed over 12 trays and 6 blocks, with each block representing storage days. Breeders received one of the two experimental diets, as shown in Table 31.

TABLE 31

Experimental Design Broiler Breeder Treatments

| Nr | Breeder Treatment | Vitamin E 50 (ppm) | PROVIOX 50 (ppm)* |
|---|---|---|---|
| 1 | Control | 160 | — |
| 2 | PROVIOX | 80 | 80 |

** Vitamin E 50 equivalence

A total of 1,080 eggs derived from the 63-week-old broiler breeders of Example 7 were collected and stored in the egg storage unit of the broiler breeder facility at Innovation Center Velddriel. At the start of the incubation period, the eggs were weighed and allocated into blocks, each block representing a storage day combination. Each block consisted of 12 experimental units, with each experimental unit indicating a group of 15 eggs. Only intact eggs were included; cracked, dirty, or eggs with deformed shells were excluded from the trial.

The eggs were placed in a NatureForm NMC 2340 Incubator with automatic control of temperature and relative humidity. From E0 till E18 the eggs were placed setter trolleys, which consist of two shelves with a capacity for 13 trays each. Each tray holds three flats of 30 eggs each. During this period, the incubator start temperature was set at 37.5° C. and relative humidity at 54%. Temperature was set based on a temperature profile starting at 37.5° C. at E0 and gradually decreasing from E12 until E18 from 37.5° C. to 36.7° C.

After the setter period (E0-E18), eggs were transferred to baskets in the hatchers based on the blocking and tray structure in the setter. The incubator temperature was set at 36.7° C. and relative humidity at 70%. Incubator temperature was recorded continuously throughout the experiment using data loggers placed at different positions inside the incubator.

Group egg weights were recorded at E0, E7 and E18. At E7 and E18 all eggs were candled and empty eggs or eggs containing dead embryos were removed (early dead E0-E7, mid dead E8-E18). At E18 eggs were transferred to the hatching baskets after candling. At hatch (E21), the number of dead chickens, late dead embryos (E19-E21), and pipped eggs were recorded. The number of hatched chickens was recorded per replicate, as well as average chick weight. Hatchability was calculated as percentage of total eggs set. Sex was determined by feather sexing, female chickens were used for dissection. All male chickens were selected for the grow out period and allocated to broiler grower pens. Only completely dry chickens, showing active movement and with a good navel score were selected. One female chicken per experimental unit was selected for dissection. Remaining chickens were euthanized by CO2 and disposed of according to local regulations. Chickens used for dissection were individually weighed and killed by cervical dislocation to measure remaining yolk-sac weight, yolk-free body mass ("YFBM"), chick length, and shank length of both shanks. Relative asymmetry was calculated according to the following formula:

$$RA=(|L-R|/[(L+R)/2])\times 100.$$

where:
L=left shank length
R=right shank length.

For comparison of the different treatments, the performance parameters (normally distributed) and hatchability and embryonic mortality (binomial distributed) were subjected to Mixed Model analysis, using SAS Version 9.3, 2008 (SAS Institute Inc., Cary, N.C.) according to the following statistical model:

$$Y_{ijk}=\mu+\alpha i+bj+a(c)ik+\varepsilon ijk$$

where:
Yijk=a specific trait per experimental unit (replicate of 15 eggs)
μ=overall mean for the specific trait
αi=fixed effect of breeder treatment (i=1-2)
bj=random effect of block/storage day (j=1-6)
a(c)ik=random nested effect of breeder pen within treatment (k=1-12)
εijk=error term The nested effect of breeder pen within treatment was included in the model to correct for the number of experimental units of the broiler breeder treatment used. Due to the design of the experiment a storage day effect was completely confounded with block (location in incubator) effect. Contrasts were used to compare treatment effects. The contrast description is given below and the contrast specification to answer the question is shown in Table 32.

1) Was there PROVIOX 50 effect?

TABLE 32

Contrast Statement Used for Statistical Analysis

|    | Control | PROVIOX |
|----|---------|---------|
| 1) | −1      | 1       |

Average egg weight at the start of the trial was 71.2 gram per egg, slightly above the breeder standards for 63-week-old Ross broiler breeders of 70.3 gram per egg. Average hatchability (72.0% of total) was slightly below average compared to breeder standards for 63 week old Ross breeders (73% of total). Variation within treatments (LSD), expressed as a percentage of average bird performance, was high for chick weight and yolk-free body mass (respectively 6.7 and 6.4%) compared to previous trials (respectively 3.5% and 3.7%) based on nine replicates per treatment).

Referring to Table 33, no significant broiler breeder treatment effects were found for hatchability of total or hatchability of fertile eggs. Late embryonic mortality (E18-E21) was significantly lower for the PROVIOX 50 treatment compared to the control diet. However, early during incubation (E0-E7) mortality was slightly higher for the PROVIOX 50 treatment compared to the control diet; therefore, no significant effects were found on hatchability.

TABLE 33

Broiler Breeder Treatment and Incubator Effects on Embryonic Mortality and Hatchability*

|                              | Control           | PROVIOX           | Overall P-value | PROVIOX effect ? |
|------------------------------|-------------------|-------------------|-----------------|------------------|
| n                            | 6                 | 6                 | —               | —                |
| Hatchability of total, %     | 78.4 (69.4-85.3)  | 72.2 (62.0-80.5)  | 0.490           | 0.297            |
| Hatchability of fertile, %   | 88.7 (83.4-92.5)  | 89.2 (83.9-93.0)  | 0.400           | 0.867            |
| Empty eggs, %                | 10.8 (6.2-18.2)   | 18.7 (11.4-29.0)  | 0.401           | 0.126            |
| Early embryonic mortality, % | 2.7 (1.4-5.0)     | 3.6 (2.1-6.4)     | 0.303           | 0.436            |
| Mid embryonic mortality, %   | 2.2 (1.1-4.6)     | 2.3 (1.1-4.8)     | 0.438           | 0.943            |
| Late embryonic mortality, %  | 2.6 (1.5-4.5)     | 0.8 (0.3-2.1)     | 0.077           | 0.042            |
| Total embryonic mortality, % | 7.6 (5-11.4)      | 6.7 (4.3-10.4)    | 0.218           | 0.674            |

Referring to Table 34, average chick weight at hatch was significantly higher for the PROVIOX 50 treatment compared to the control treatment. When corrected for initial egg weight it was still significantly higher compared to the control treatment. Relative remaining yolk sac weight at hatch was significantly lower for the PROVIOX 50 treatment compared to the control treatment, suggesting an increased yolk usage.

TABLE 34

Broiler Breeder Treatment Effects on Embryonic Development and Chick Quality Parameters at Hatch of Ross 308 Embryos

|                                    | Control | PROVIOX | Overall SEM | Overall P-Value | PROVIOX effect? |
|------------------------------------|---------|---------|-------------|-----------------|-----------------|
| n                                  | 6       | 6       | —           | —               | —               |
| Egg weight E0, g                   | 70.8    | 71.4    | 0.4998      | 0.783           | 0.322           |
| Egg weight E7, g                   | 68.0    | 68.6    | 0.5049      | 0.733           | 0.380           |
| Egg weight E18, g                  | 64.3    | 65.0    | 0.5232      | 0.531           | 0.383           |
| Moisture Loss E0-E7, %             | 3.9     | 3.9     | 0.2394      | 0.374           | 0.865           |
| Moisture Loss E0-E18, %            | 9.1     | 9.1     | 0.2842      | 0.111           | 0.854           |
| Chick weight average, g            | 47.7    | 50.1    | 0.7240      | 0.079           | 0.018           |
| Relative chick weight[1], %        | 67.3    | 70.2    | 0.9620      | 0.049           | 0.012           |
| Chick weight dissected chicks, g   | 48.9    | 49.0    | 0.5955      | 0.168           | 0.883           |
| Yolk weight, g                     | 6.1     | 5.4     | 0.3023      | 0.239           | 0.067           |
| Relative yolk weight[2], %         | 12.5    | 10.9    | 0.5553      | 0.084           | 0.032           |
| YFBM[3], g                         | 42.5    | 43.2    | 0.4874      | 0.010           | 0.281           |
| Chick length, cm                   | 19.4    | 19.4    | 0.0994      | 0.540           | 0.404           |
| Relative asymmetry, %              | 1.4     | 1.3     | 0.1301      | 0.089           | 0.444           |
| Shank color                        |         |         |             |                 |                 |
| Minolta, L (lightness)             | 61.7    | 61.6    | 0.3775      | <.0001          | 0.684           |
| Minolta, a (redness)               | 8.3     | 8.2     | 0.3580      | <.0001          | 0.765           |
| Minolta, b (yellowness)            | 13.2    | 14.2    | 0.4386      | <.0001          | 0.116           |

[1]Expressed as percentage of egg weight at E0
[2]Expressed as percentage of chick weight
[3]Yolk free body mass No significant effects were found on hatchability of total or fertile eggs. Supplementing the breeder diet with PROVIOX 50 resulted in significant heavier offspring and an increased yolk usage.

Example 9—Grow Out of Chickens from Example 8

Two broiler breeder feed treatments were evaluated (Table 35).

TABLE 35

Experimental Design Broiler Breeder Treatments

| Treatment | Vitamin E 50 (ppm) | PROVIOX 50 (ppm)* |
|---|---|---|
| Control | 160 | — |
| PROVIOX | 80 | 80 |

*Vitamin E 50 equivalence

Hatched chickens from Example 8 were grown out that resulted from the broiler breeder experiment of Example 7, where the breeders received a control diet or a diet where 50% of the vitamin E was replaced by PROVIOX 50. In this Example, the same basal diet was fed to all broilers. The experimental period was divided into a starter phase (0-14 days) and a grower phase (14-34 days). At 14 days of age, all birds changed to their grower diet.

In advance of diet formulation, ingredients (corn and soybean meal) were reserved and analyzed for crude protein ("CP") (ISO 16634) and calcium (ISO 27085:2009) content at the Provimi B.V. laboratory, Rotterdam, the Netherlands. Corn was analyzed for phosphorus content (ISO 27085:2009) and soybean meal for potassium (ISO 27085:2009). Near-infrared reflectance spectroscopy analysis (ISO 12099) was applied to estimate dry matter, crude fat, crude fiber, and crude ash content.

Starter and grower diets were optimized within and based upon the new Cargill Nutrient System ("CNS") and the poultry shadow feeds (TD 2014 1). The starter and grower diet formulations were derived from shadow feeds P_BRHIGH51 and P_BRHIGH52, respectively. In accordance with the CNS matrix, an AME uplift was attributed to the used NSP enzyme (Hostazyme X, 100 g/MT; +40 kcal/kg). A phytase enzyme (Phzyme 10000 TPT) was included in both diets at PHY IDX 9. Composition of the experimental starter and grower diets are provided in Table 36. Analyses of the diets are shown in Table 37. The starter and grower diet were produced by Research Diet Services (RDS, Wijk bij Duurstede, the Netherlands). Starter diets were pelleted at 2.5 mm and grower diets at 3 mm with steam addition (about 80° C.).

TABLE 36

Ingredient and Nutrient Composition of Diets

| | | Feeding Phase | |
|---|---|---|---|
| | | Starter | Grower |
| | | Feedcode | |
| | | BG 1402-1 | BG 1402-10 |
| | | Diet Form | |
| Ingredient Composition (g/kg) | | Pellet - 2.5 mm | Pellet - 3.0 mm |
| Wheat (A5734) | | 20.000 | 20.000 |
| Maize (A5733) | | 41.394 | 44.212 |
| Soybean Meal HP (A5714) | | 33.665 | 30.915 |
| Fat, from Animals | | 0.498 | 0.636 |
| Fats/Oils, Soybean Oil | | 0.498 | 0.636 |
| Sodiumbicarbonate | | 0.000 | 0.010 |
| Salt | | 0.379 | 0.347 |
| Monocalciumphosphate | | 0.737 | 0.612 |
| Limestone | | 1.378 | 1.191 |
| L-Threonine | | 0.037 | 0.044 |
| L-Lysine HCL | | 0.166 | 0.164 |
| DL-Methionine | | 0.230 | 0.215 |
| PHY9 Natup D10000 P | | 0.008 | 0008 |
| ENZ C HOstx D 100 P-CORN | | 0.010 | 0.010 |
| Broiler Premix 1%[1] | | 1.000 | 1.000 |
| Total | | 100.00 | 100.00 |
| Nutritional Composition (%) | | | |
| 1110ac | Dry Matter | 87.5 | 87.4 |
| 1111ac | Moisture | 12.5 | 12.6 |
| 1120ac | Crude Protein | 21.8 | 20.7 |
| 1130ac | Crude Fat | 3.6 | 3.9 |
| 1140 | Crude Fibre | 2.6 | 2.6 |
| 1140ac | <FIBER | 2.5 | 2.5 |
| 1511ac | Calcium | 0.78 | 0.68 |
| 1513ac | Phosphorus P | 0.55 | 0.51 |
| 1521ac | Sodium | 0.16 | 0.15 |
| 1522ac | Potassium | 0.97 | 0.92 |
| 1523ac | Chloride | 0.30 | 0.28 |
| 1530 | dEB | 233 | 221 |
| 3317 | PO RETP | 0.39 | 0.36 |
| 3335 | <PLT DEB | 230 | 218 |
| 6300 | PHY IDX | 9.0 | 9.0 |
| 3110 | ME Poultry | 2858 | 2912 |
| 3130 | ME Broiler | 2669 | 2727 |
| 3132ac | PME 0 21 | 2800 | 2850 |
| 3134ac | PME 22 42 | 2880 | 293 |
| 3136ac | PME42+ | 2950 | 3006 |
| 1209ac | <lYSINE | 1.300 | 1.225 |
| 1211ac | <METHION | 0.571 | 0.543 |
| 1213ac | <MET + CYS | 0.971 | 0.928 |
| 1214ac | <THREONINE | 0.823 | 0.789 |
| 1215ac | <TRYPTOPHIN | 0.278 | 0.261 |
| 1216ac | <ISOLEUC | 0.918 | 0.867 |
| 1218ac | <VALINE | 1.037 | 0.985 |
| 1219ac | <ARGININE | 1.430 | 1.347 |
| 3200ac | PO TFD LYS | 1.200 | 1.130 |
| 3201ac | PO TFD MET | 0.545 | 0.518 |
| 3203ac | PO TFD MC | 0.890 | 0.850 |
| 3204ac | PO TFD THR | 0.740 | 0.710 |
| 3205ac | PO TFD TRP | 0.255 | 0.240 |
| 3206ac | PO TFD ILE | 0.844 | 0.798 |
| 3208ac | PO TFD VAL | 0.936 | 0.890 |
| 3209ac | PO TFD ARG | 1.345 | 1.267 |
| x3201a | PO TFD MET/LYS | 0.454 | 0.458 |
| x3203a | PO TFD M + C/LYS | 0.742 | 0.752 |
| x3204a | PO TFD THR/LYS | 0.617 | 0.628 |
| x3205a | PO TFD TRP/LYS | 0.212 | 0.212 |
| x3206a | PO TFD ILE/LYS | 0.703 | 0.706 |
| x3208a | PO TFD VAL/LYS | 0.780 | 0.788 |
| x3209a | PO TFD ARG/LYS | 1.120 | 1.121 |
| 1210 | Lysine | 1.274 | 1.199 |
| 1211 | Methionine | 0.557 | 0.529 |
| 1213 | Meth. + Cyst. | 0.919 | 0.877 |
| 1214 | Threonine | 0.842 | 0.807 |
| 1215 | Tryptophan | 0.256 | 0.241 |
| 1216 | Isoleucine | 0.921 | 0.869 |
| 1218 | Valine | 1.021 | 0.970 |
| 1219 | Arginine | 1.454 | 1.368 |

TABLE 36-continued

Ingredient and Nutrient Composition of Diets

| | | Feeding Phase | |
|---|---|---|---|
| | | Starter | Grower |
| | | Feedcode | |
| | | BG 1402-1 | BG 1402-10 |
| | | Diet Form | |
| | Ingredient Composition (g/kg) | Pellet - 2.5 mm | Pellet - 3.0 mm |
| 1230 | Glycine + Serine | 1.979 | 1.877 |
| 3200 | Dig. Lysine (poultry) | 1.105 | 1.037 |
| 3201 | Dig. Methionine (poultry) | 0.517 | 0.491 |
| 3203 | Dig. Meth. + Cyst (poultry) | 0.808 | 0.769 |
| 3204 | Dig. Threonine (poultry) | 0.703 | 0.673 |
| 3205 | Dig. Tryptophan (poultry) | 0.224 | 0.210 |
| 3206 | Dig. Isoleudine (poultry) | 0.802 | 0.756 |
| 3208 | Dig. Valine (poultry) | 0.870 | 0.824 |
| 3209 | Dig. Arginine (poultry) | 1.287 | 1.211 |
| 3219 | Dig. Glycine + Serine (poultry) | 1.657 | 1.570 |
| 1327 | C18:2 (Linoleic acid) | 1.5 | 1.6 |
| 1327ac | <lINOLEIC | 1.8 | 1.9 |

[1]Supplied per kg starter diet: Vitamin A (retinyl-acetate), 12,000 IU; vitamin D3 (cholecalciferol), 5,000 IU; vitamin E (DL-α-tocopherol), 30 mg; vitamin K3 (menadione), 2.3 mg; vitamin B1 (thiamine), 1.0 mg; vitamin B2 (riboflavin), 4.5 mg; vitamin B6 (pyridoxine-HCL), 2.7 mg; vitamin B12 (cyanocobalamine), 20 μg; niacine, 40 mg; D-pantothenic acid, 9 mg; choline chloride, 500 mg; folic acid, 0.5 mg; biotin, 100 μg; FeSO4•H2O, 150 mg; CuSO4•5H2O, 40 mg; MnO, 100 mg; ZnSo4•H2O, 145 mg;; KJ, 2.0 mg; Na2SeO3, 0.56 mg; antioxidant (oxytrap PXN), 125 mg.
Supplied per kg grower diet: vitamin A (retinyl-acetate), 10,000 IU; vitamin D3 (cholecalciferol), 2,000 IU; vitamin E (DL-α-tocopherol), 20 mg; vitamin K3 (menadione), 2.3 mg; vitamin B1 (thiamine), 0.8 mg; vitamin B2 (riboflavin), 4.5 mg; vitamin B6 (pyridoxine-HCL), 1.9 mg; vitamin B12 (cyanocobalamine), 20 μg; niacine, 30 mg; D-pantothenic acid, 8 mg; choline chloride, 400 mg; folic acid, 0.5 mg; biotin, 50 μg; FeSO4•H2O, 150 mg; CuSO4•5H2O, 40 mg; MnO, 100 mg; ZnSo4•H2O, 145 mg; KJ, 1.9 mg; Na2SeO3, 0.50 mg; antioxidant (oxytrap PXN), 125 mg.
[2]According to CVB (2006) calculations; 3AFD = apparent fecal digestibility; 4TFD = true fecal digestibility.

TABLE 37

Calculated and Analyzed Nutritional Composition of the Starter and Grower Diets

| Diet Code | BG1402-1 | BG1402-10 |
|---|---|---|
| Calculated Nutrients, % | | |
| Crude Protein | 21.8 | 20.7 |
| Crude Fat | 3.6 | 3.9 |
| Crude Fibre | 2.5 | 2.5 |
| Dry Matter | 87.5 | 87.4 |
| Ca | 0.78 | 0.68 |
| P | 0.55 | 0.51 |
| Analysed Nutrients | | |
| Crude Protein | 22 | 21.3 |
| Crude Protein (NIRS) | 22.1 | 20.8 |
| Crude Fat (NIRS) | 3.5 | 3.8 |
| Crude Fibre (AOCS Ba 6a-05) | 2.2 | 2.1 |
| Crude Fibre (NIRS) | 2.6 | 2.4 |
| Moisture (NIRS) | 11.6 | 12.2 |
| Dry Matter | 88.4 | 87.8 |
| Ca | 0.86 | 0.67 |
| P | 0.61 | 0.55 |
| % of expected | | |
| Crude Protein | 101 | 103 |
| Crude Fat | 97 | 97 |
| Crude Fibre | 102 | 96 |
| Dry Matter | 101 | 100 |
| Ca | 110 | 98 |
| P | 111 | 108 |

A total of 252 Ross 308 male one-day-old chickens, derived from 63-week-old broiler breeders of Example 7, were selected from the total number of hatched male chickens from Example 8. Chickens were randomly selected from different experimental units in the hatchery, ensuring the experimental unit of the broiler breeder facility was kept intact, placing chickens from one experimental unit of the broiler breeder facility into one pen in the grow out facility. Each pen consisted of 21 chicks with an initial individual body weights of 49.1 g±1.0 g and 48.5 g±1.0 g for respectively units A and B.

The pens (90 cm×225 cm) had a raised floor, consisting of stainless steel covered with a 2-cm layer of wood shavings. Each pen was equipped with two sets of two adjustable nipple drinkers and a feeder that was positioned inside the pen for the first 13 days. From day 14 onwards, feed was supplied via a feeder trough in front of the pen. Both feed and water were provided ad libitum throughout the study. Continuous artificial lighting was maintained for 23 hours/day for the first three days of the experiment, 20 hours/day between day four and day seven, and 18 hours/day for the remainder of the experiment. Temperature, relative humidity, and ventilation were computer controlled, with the temperature gradually decreasing by 0.5° C. per day the first 13 days, from day 14 until day 35 the temperature gradually decreased by approximately 0.4° from 34.0° C. on the day of arrival (1-day-old chickens) to a temperature of 19.6° C. at day 35 and was kept constant at 19.6° C. until the end of the experiment (day 35). Room temperature was recorded continuously using data loggers, and relative humidity was set at 50% throughout the experiment. The chickens were spray-vaccinated against Newcastle Disease with the Poulvac NDW-vaccine (Poulvac NDW-vaccin, Intervet, Boxmeer, The Netherlands) at 14 days of age.

Room temperature was recorded continuously throughout the experiment using data loggers placed inside the facility, one per room. Individual body weights were recorded at the start of the experiment (day 0) and at 7, 14, 21, 28, and 34 days of age. In addition, feed consumption for each pen was recorded on the same day the chickens were weighed. Based on calculated body weight gain and feed consumption, feed to gain ratio (F:G) was calculated as kg of feed consumed/kg of weight gain. Total feed consumption per pen was corrected for mortality, culling and outliers. The European Poultry Index (De Herdt et al., 1999) was calculated with (1) and without mortality (2) using the following formulas:

European Poultry Index=(Final Body Wt (g)×(100%-Mortality %))/((10×period in days)×overall FCR)     1.

European Poultry Index=(Final Body Wt (g)×100)/((10×period in days)×overall FCR)     2.

To determine immune status development of the chicks, all chicks were individually inoculated with HuSA, according to the method described by Parmentier et al. (2008), at 14 days of age in the trachea, and blood samples (6 chicks per pen, color coded) were collected at days 14, 21, 28, and 34. Blood plasma was stored for further analysis of IgT, IgA, IgY, and IgM content (Wageningen University laboratory, Wageningen, The Netherlands). On a weekly basis, starting at 21 days of age, litter quality was given a score between 1 and 5 by multiple observers. At day 34 of the experiment, five birds per pen (excluding obvious outliers) were selected at random. Excreta was collected overnight and sampled in the morning (day 35).

After collection, excreta were thoroughly mixed and a 10 ml plastic test tube (heparin blood tube) was filled for free water analysis and an NW bag was filled for NIR analysis (Provimi laboratory, Rotterdam, The Netherlands). Free water was analyzed by centrifuging the filled test tubes at 3,000 rpm for 12 minutes. The water (g) on top of solids was expressed as percentage of excreta weight (g) before centrifuging. At 35 days of age, the birds were starved overnight (approximately 8 hours) and slaughtered the next day. In the morning of day 36, these selected birds were successively weighed, killed by $CO_2/O_2$, bled, and the feathers were removed. The weight of the carcass (whole bird without feathers, blood, organs, intestines, head and legs below the hock) was determined and carcass yield was calculated as a percentage of the feed-deprived bird weight (whole bird weight before slaughtering). In addition, the breast (pectoralis major, pectoralis minor, sternum and clavicle), and the abdominal fat pad weight were determined and their yields were calculated as a percentage of the carcass weight. Spleen and liver weights were also determined and were also expressed relatively, as percentage of the individual body weight.

All normally distributed performance data were subjected to the PROC MIXED statement procedure in SAS Version 9.3 (SAS Institute Inc., Cary, N.C.) according to the following statistical model:

$$Yij = \mu + \alpha i + bj + \epsilon ij$$

where:
Yij=a specific trait measured for each experimental unit
μ=overall mean for the specific trait
αi=fixed effect of broiler breeder treatment (i=1-2)
bj=random block effect (j=1-6)
eij=residual error term Mortality was analyzed as binomial, litter scores as ordinal data using PROC GLIMMIX statement procedure in SAS Version 9.3 (SAS Institute Inc., Cary, N.C.) using the same model. To account for day effect of the repeated litter scores, for these analysis day was taken into account in the statistical model as a covariate. To correct for person effect in the litter scoring, the variable person was considered as a random effect in the statistical model. Blood results were analyzed using repeated measurements, with an individual bird as subject. Contrasts were used to compare treatment effects. The contrast description is given below and the contrast specification to answer the question is shown in Table 38.

1) Was there a PROVIOX 50 effect?

TABLE 38

Contrast Statements Used for Statistical Analysis

|  | Control | PROVIOX |
|---|---|---|
| 1) | −1 | 1 |

Nutritional composition of the diets was in line with the expected values (Table 37). Observed health status of the birds was good throughout the experiment. Although mortality, including culling, reached 5.7%, which is somewhat high compared with practical levels (3 to 4%) and with previous broiler grower studies (mean 3.9%). Average technical performance (mean body weight at 34 days: 2,516 g) was high compared to other experiments carried out at the broiler facilities of Innovation Center Velddriel (mean BW: 2,383 g). Variation within blocks (LSD), expressed as a percentage of average bird performance, was average for weight gain and FCR, with 4.2 and 1.7% respectively (max. 21 chickens per pen and 6 replicates—data not shown) compared to previous data (mean LSD BW and FCR: 4.0 and 1.8%).

Offspring growth performance was not significantly affected by any of the broiler breeder diets. In a previous study evaluating the effect of PROVIOX 50 in the breeder diet on offspring growth performance, a 2.4% improvement of ADG was found at the inclusion level that was also used in the current trial. Now the numerical increase was only 1.3% (see Table 39). In the previous study, the effect of replacement was more pronounced at the high vitamin E level (160 ppm; improving ADG and F:G). Current and previous results suggest that the combination of antioxidants in the broiler breeder diet is beneficial for offspring growth performance, and the effects seem to be most pronounced for offspring of younger broiler breeders and with a basal vitamin E level of 80 ppm.

TABLE 39

Broiler Breeder Treatment Effects on Offspring Mortality, Body Weight, European Poultry Index ("EPI"), Average Daily Gain ("ADG"), Average Daily Feed Intake ("ADFI"), and Feed to Gain Ratio (F:G) of Ross 308 Male Broilers

|  | Control | PROVIOX | P-Value | PROVIOX effect |
|---|---|---|---|---|
| n[1] | 6 | 6 | — | — |
| Mortality, % | 4.0 | 5.0 | — | 0.063 |
| BW 0 d, g | 49.0 | 48.5 | 0.43 | 0.790 | ns |
| BW 34 d, g | 2491 | 2523 | 35.03 | 0.580 | ns |
| CV 0 d, % | 7 | 7 | 0.62 | 0.491 | ns |
| CV 34 d, % | 7.1 | 7.4 | 1.01 | 0.911 | ns |
| EPI | 476 | 472 | 10.29 | 0.183 | ns |
| EPI excl mortality | 495 | 501 | 8.48 | 0.456 | ns |
| ADG 0-14 d, g | 37.8 | 37.5 | 0.65 | 0.545 | ns |
| ADG 14-34 d, g | 95.6 | 97.5 | 1.40 | 0.379 | ns |
| ADG 0-34 d, g | 71.8 | 72.8 | 1.03 | 0.575 | ns |
| ADFI 0-14 d, g | 44.2 | 43.6 | 0.82 | 0.416 | ns |
| ADFI 14-34 d, g | 149.7 | 152.9 | 2.01 | 0.570 | ns |
| ADFI 0-34 d, g | 106.3 | 107.9 | 1.44 | 0.782 | ns |
| F:G 0-14 d | 1.169 | 1.162 | 0.008 | 0.346 | ns |
| F:G 14-34 d | 1.565 | 1.569 | 0.011 | 0.696 | ns |
| F:G 0-34 d | 1.479 | 1.482 | 0.009 | 0.617 | ns |
| F:G Corrected for BW[2] | 1.479 | 1.476 | 0.013 | 0.422 | ns |

Mortality = percentage of total mortality and culling relative to the number of birds at day 0;
EPI = ((Final Body Wt(g) × (100% − Mortality %))/((10 × period in days) × overall FCR));
EPI excl. mortality = ((Final Body Wt (g) × 100%)/((10 × period in days) × overall FCR));
F:G = g feed intake:g gain
[1]Individual pen with 21 birds
[2]F:G corrected for BW = F:G corrected to 2,491 gram bodyweight at 34 d of age. Correction of −0.02 for each 100 g extra weight
NS = P > 0.10;
* = P < 0.05,
*** = P < 0.01.

When evaluating dissection parameters and excreta results (Table 40) no significant differences were found.

TABLE 40

Broiler Breeder Treatment Effects on Dissection Parameters, Litter Scores, and Excreta Content of Ross 308 Male Broilers.

|  | Control | PROVIOX |  | P-Value | PROVIOX effect |
|---|---|---|---|---|---|
| n[1] | 6 | 6 | — | — | — |
| BW at 36 d | 2581 | 2560 | 40 | 0.656 | ns |
| Carcass, g | 1766 | 1728 | 25 | 0.414 | ns |
| Carcass, % of BW | 68.3 | 67.5 | 0.44 | 0.640 | ns |
| Breast 36 d, g | 725 | 710 | 11.3 | 0.192 | ns |
| Breast, % of carcass | 41.1 | 41.1 | 0.28 | 0.180 | ns |
| Breast as % of carcass, corrected for BW[2] | 40.9 | 40.9 | 0.28 | 0.269 | ns |
| Abdominal fat pad 36 d, g | 18 | 20 | 1.14 | 0.524 | ns |
| Abdominal fat pad, % of carcass | 1.0 | 1.2 | 0.07 | 0.529 | ns |
| Liver weight, g | 62.0 | 62.2 | 1.314 | 0.062 | ns |
| Liver weight, % of carcass | 2.40 | 2.44 | 0.048 | 0.001 | ns |
| Spleen weight, g | 2.7 | 2.6 | 0.261 | 0.775 | ns |
| Spleen weight, % of carcass | 0.10 | 0.10 | 0.010 | 0.695 | ns |
| Probability of a generally lower litter score[3] | 33.4 | 35.3 | — | 0.784 | ns |
| Excreta free water content, % | 28.4 | 29.7 | 2.71 | 0.847 | ns |
| Excreta, analyzed with NIRS, g/kg | | | | | |
| N | 12.1 | 12.6 | 0.62 | 0.365 | ns |
| NDF | 42.2 | 43.9 | 5.03 | 0.546 | ns |
| Ca | 3.82 | 3.70 | 0.195 | 0.428 | ns |
| P | 0.19 | 0.18 | 0.017 | 0.716 | ns |
| Moisture | 794 | 793 | 4.88 | 0.732 | ns |

[1]Average of 5 birds per pen, n is number of pens
[2]Breast meat % corrected to 2,491 gram bodyweight at 42 days of age. Correction of 0.2% for each 100 gram extra weight
[3]Average score per treatment (based on pen level)

HuSA IgA titers were reported to be very low and therefore not reliable and so these results are not discussed. No significant interactions were found between breeder treatment and day for the HuSA specific plasma titers (see Table 41).

TABLE 41

Interaction Effects Between Broiler Breeder Treatment and Collection Day Effects on Blood Plasma HuSA and LPS Titers

|  | Treatment | | | | | | | | | |
|---|---|---|---|---|---|---|---|---|---|---|
|  | Control | | | | PROVIOX | | | | | |
|  | Day | | | | | | | | | |
|  | 14 | 21 | 28 | 34 | 14 | 21 | 28 | 34 | SEM | P-Value |
| n[1] | 6 | 6 | 6 | 6 | 6 | 6 | 6 | 6 | — | — |
| HuSaIgA | −1.6 | 0.1 | 1.4 | 1.5 | −1.6 | 0.5 | 0.9 | 1.8 | 0.230 | 0.079 |
| HuSaIgG | 4.2 | 9.1 | 8.9 | 8.5 | 3.6 | 9.4 | 8.9 | 8.8 | 0.399 | 0.400 |
| HuSaIgM | 0.8 | 3.7 | 4.0 | 2.9 | 0.7 | 4.4 | 3.7 | 3.2 | 0.194 | 0.149 |
| HuSaIgT | 1.7 | 6.0 | 5.8 | 5.1 | 1.3 | 6.3 | 5.9 | 5.2 | 0.344 | 0.634 |
| LPSIgA | −2.0 | −1.5 | −0.3 | 0.6 | −2.1 | −1.1 | −0.3 | 0.7 | 0.173 | 0.115 |
| LPSIgG | 0.9 | 0.5 | 0.8 | 1.9 | 1.3 | 0.7 | 1.3 | 1.8 | 0.115 | 0.014 |
| LPSIgM | −0.5 | 1.0 | 2.5 | 3.8 | 0.0 | 1.3 | 2.8 | 3.6 | 0.128 | 0.138 |
| LPSIgT | 1.0 | 1.1 | 1.8 | 2.7 | 1.3 | 1.6 | 2.2 | 2.6 | 0.111 | 0.367 |

[1]Average of 6 birds per pen

Figure 9:
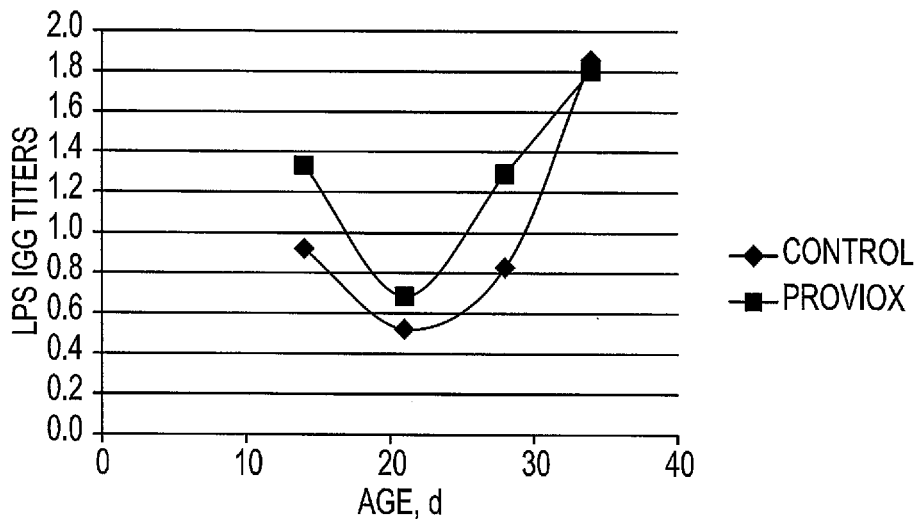
FIG. 9 is a graph showing the response of LPS IgG titers in relation to broiler breeder treatment and age for Example 9.

For the LPS IgG titer a significant interaction was found, which was due to a relatively higher increase at 34 days of age for the offspring of breeders receiving the control diet (FIG. 9).

Figure 10:
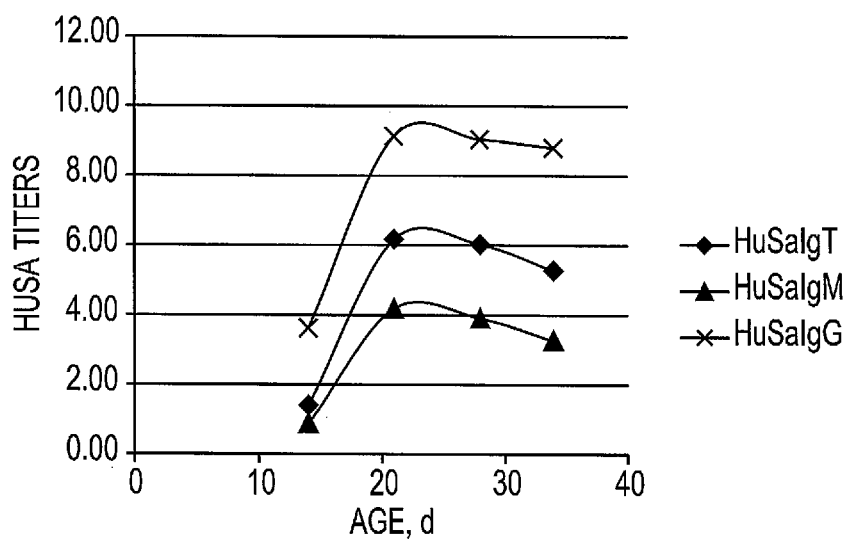
FIG. 10 is a graph showing the response of HuSA-specific titers in relation to the age of the chicks for Example 9.

HuSA specific titers were significantly affected by day, indicating that before HuSA inoculation values were lower, and increased after inoculation, to decrease again when the chicks were older (see FIG. 10). This is in accordance with what was expected. LPS titers increased when chicks were older, this is also in accordance with what was expected.

Figure 11:
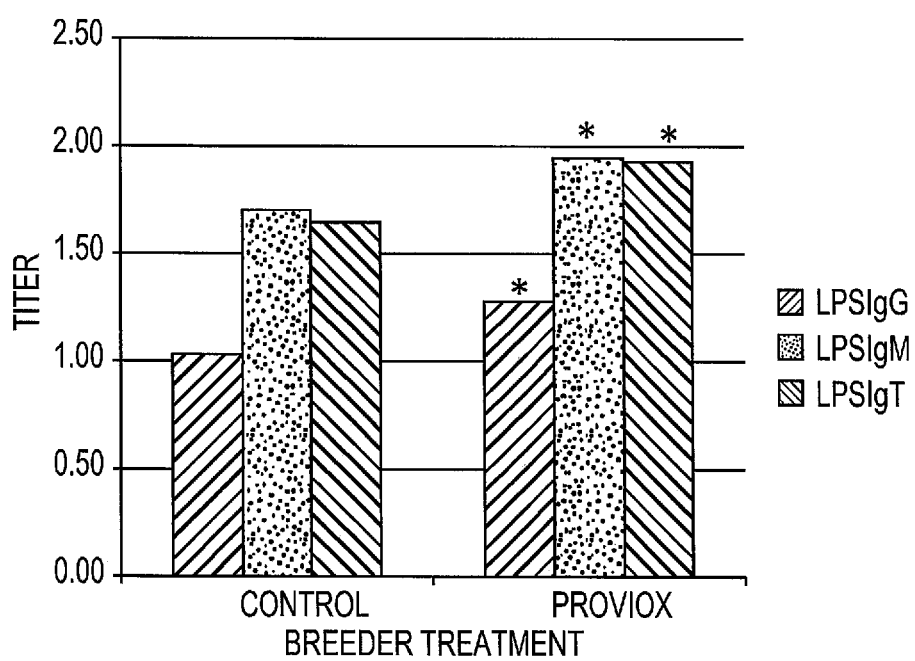
FIG. 11 a graph showing the response of LPS titers in relation to broiler breeder treatment for Example 9.

Referring to FIG. 11, LPS titers (IgG, IgM, and IgT) were significantly higher for offspring of breeders receiving the partially replacement of vitamin E by PROVIOX 50. These results suggest that immune activity was higher for offspring of broiler breeder receiving PROVIOX 50.

Results of the instant and previous grow out studies suggest that offspring growth performance is improved when a combination of antioxidants in the broiler breeder diet is fed. The effects seem to be most pronounced for offspring of younger broiler breeders and with a basal vitamin E level of 80 ppm. Analysis of immune blood plasma parameters showed an increase in non-specific titers when vitamin E was partially (50%) replaced by PROVIOX 50 in the broiler breeder diet.

Example 10—Method of Feeding a Porcine Animal

The aim of this Example was to prove efficacy of the PROVIOX 50 in pigs. The efficacy of the product was evaluated by comparing the PROVIOX 50 supplemented group in view of sows response criteria, litter response criteria, antioxidant and vitamin E status to negative control group and groups with different content of vitamin E.

The trial was conducted at a farm in Poland. In general the housing and management conditions on the chosen workplace were considered representative for the geographical region. The breeding, gestation, and farrowing facilities of the farm were fully enclosed buildings with rooms that were ventilated and heated to maintain a minimum comfort zone temperature for the sows.

The ambient temperature in the gestation sow accommodation and the farrowing house was kept at a fairly constant 18-20° C. and 60% relative humidity. Generally, all workplaces meet requirements for group comparative trials and requirements of valid rules concerning protection of animals.

Testing was performed on sows (primiparous and multiparous) of the same type of crossing (PIC). The trial comprised 52 sows in a system of continuous farrowing. Each group was consist of 13 animals. The trial ran from day 1 of pregnancy to remating in the next cycle.

There were two dietary compositions: LP 0-90 d, LK-90 d of gestation-weaning. Feed fed throughout the study was manufactured in the feed mill of the farm. The feed produced was complete feeds according to the standard feeding management procedures on the participating farm. Feed consistency was mash. All diets were analyzed for nutrients and vitamin E content (AOAC, 2000). The feeds are shown in TABLE 42.

TABLE 42

|  |  | LP | LK |
|---|---|---|---|
| Specification |  |  |  |
| Barley | % | 40.0 | 10.0 |
| Triticale | % | 25.5 | 20.5 |
| Wheat | % | 5.0 | 10.0 |
| Corn | % | 15.0 | 32.5 |
| Soybean meal | % | 9.0 | 19.0 |
| Vegetable oil (EVO) | % | — | 2.5 |
| Lonocel (lignocellulose product) | % | 3.0 | 1.5 |
| Premix LP | % | 2.5 | — |
| Premix LK | % | — | 4.0 |
| Nutritive value |  |  |  |
| Net energy | kcal/kg | 2155 | 2320 |
| Crude protein | % | 14.0 | 17.0 |
| Lysine | % | 0.70 | 1.05 |
| Methionine + cystine | % | 0.51 | 0.62 |
| Threonine | % | 0.51 | 0.69 |
| Tryptophan | % | 0.16 | 0.20 |
| Calcium | % | 0.70 | 0.95 |
| Digestible phosphorus | % | 0.36 | 0.47 |
| Sodium | % | 0.14 | 0.25 |

Name of tested product: PROVIOX 50

Each group was fed with complete diets for pregnant sows (0-90 d) and for lactation sows (90 d of gestation-weaning) with different inclusion of vitamin E and tested product (see TABLE 43A) and lactation diets (see TABLE 43B)

TABLE 43A

Gestation diets (0-90 d o: "gestation) - LP diets

Inclusion of vitamin E and PROVIOX 50

| Group 1 | Vitamin E - 0 mg/kg |
| Group 2 | Vitamin E - 50 mg/kg |
| Group 3 | Vitamin E - 100 mg/kg |
| Group 4 | Vitamin E 50 mg/kg + PROVIOX 50 mg/kg |

TABLE 43B

Lactation diets (90 d of gestation-28 d of lactation) - LK diets

Inclusion of vitamin E and PROVIOX 50

| Group 1 | Vitamin E - 0 mg/kg |
| Group 2 | Vitamin E - 75 mg/kg |
| Group 3 | Vitamin E - 150 mg/kg |
| Group 4 | Vitamin E 75 mg/kg + PROVIOX 50 75 mg/kg |

The performance following criteria were monitored during the trial: (i) Sows response criteria (actual parity, farrowing rate, culled sows—number and reasons, wean-to-mating interval, farrowing rate in the next cycle); (ii) litter response criteria (number of piglets, total, alive, stillborn, mummies; weight of piglets and litters; survival). The following biochemical (blood) criteria were monitored during the trial for the sows (mating, farrowing and weaning), piglets $21^{st}$ day: (i) glutathione peroxidase (GPx) activity; (ii) superoxide dismutase (SOD) activity; (iii) total antioxidant status (TAS); (iv) vitamin E content; (v) vitamin A content.

To determine the oxidative status, the blood samples were collected from sows and piglets into tubes with lithium anticoagulant—received whole blood for analysis. At the same time blood samples were taken for blood clot. They were centrifuged (1500 rpm, 15 Temp. 4° C.) and obtained serum was pipetted into separate tubes.

In studies of oxidative status of sows and piglets were used suitable to each of the indicators, the reagent kits from Sigma-Aldrich. Determination was made in accordance with the descriptions of the rules and procedures specified by the manufacturer.

The content of the TAS (total antioxidant status) were determined using the Antioxidant assay kit (Cat. No CS0790), the activity of SOD (superoxide dismutase) was determined using SOD determination kit 19160, the activity of GPx (glutathione Peroxide assai Cellular Activity Kit) Cat. No CGP1. The content of vitamins A and E by McMurray and Blanchflower 1979 (Journal of Chromatography 178, 525-531.). TAS Serum samples (10 ul) in duplicate were incubated at room temperature for 5 minutes with the working solution of ABTS (2,2-azino-bis (3-ethylbenzthiazoline-6-sulfonic acid) (150 pl) and the solution with myoglobin (20 pl). Simultaneously the calibration curve was performed based on serial dilutions of Trolox equivalent in the range of 0.015 to 0.42 mM (mmol).

The formed a ferryl radical from myoglobin and hydrogen peroxide causes oxidation of ABTS and production of radical cation ABTS*. The resulting chromogen has a blue-green color. In the presence of antioxidants the radical cation is suppressed to an extent dependent on the activity of the antioxidant and the color intensity is decreased proportionally. The color was measured with a spectrophotometer at a wavelength of 405 nm.

Serum samples (20 ul) in duplicate were incubated at 37° C. for 20 minutes with the working solution WST (tetrazolium sodium salt, 2-(4-Iodophenyl)-3 (4-nitrophenyl0-5-(2, 4-disulfophenyl) 2H-tetrazolium, monosodium salt) (200 pl) and the enzyme working solution (20 pl). Simultaneously sample blanks were performed (two reagents, and blank for each sample) and a calibration curve based on serial dilutions of SOD in a range of 200 to 0,001 U/ml. Absorbance of the blank, standards and test samples read on a spectrophotometer at a wavelength of 450 nm. WST produces a water-soluble formazan dye upon reduction with a superoxide anion. The rate of the reduction with $O_2$ are linearly related to the xanthine oxidase (XO) activity. The SOD activity is measured as the degree of blocking the formation of the formazan dye.

Whole blood samples (blood collection from animals to tubes with lithium anticoagulant) in duplicate (10 pl) was added to 930 ml of buffer (pH 8), mixed (vortex—10'), then added 10 pl of a 70% aqueous solution of tert-butyl Hydroperoxide, mixed (by inversion) and the absorbance was measured immediately in a spectrophotometer at a wavelength of 340 nm. After 1 minute the measurement was repeated. Simultaneously blank samples (reagent) were performed and a calibration curve based on GPx serial dilutions in the range of 20 to 50 U/ml. The decrease in NADPH absorbance (during 1 minute) measured at 340 nm during the oxidation of NADPH to NADP+ is indicative of GPx activity.

Serum samples (1 ml) was deproteinized with anhydrous ethanol (1 ml), extracted with 5 ml of n-hexane (Vortex 5'), then centrifuged (3000 rpm, 10', temp. 4° C.). The resulting 4 ml of the supernatant were evaporated to dryness under nitrogen, and then dissolved in 1 ml of 96% ethanol and analyzed by high performance liquid chromatography (HPLC).

The contents of retinol and tocopherol was determined by reversed-phase high performance liquid chromatography (HPLC) with chromatograph SHIMADZU. Nucleosil C18 column is used, the carrier phase was methanol-water (95:5, v:v). The measurement was performed using a UV detector at a wavelength of 326 nm to determine the amount of retinol and a fluorescence detector (excitation wavelength—295 nm, emission wavelength—330 nM) to determine the tocopherol content. The concentration of retinol and tocopherol were calculated on the basis of the peak external standards (Sigma-Aldrich (□)-a-Tocopherol, Retinol Vitamin-A-alcohol).

Experimental results were processed statistically with the use of the one-way analysis of variance and Duncan's test. The results obtained were characterized with an arithmetic mean (x), a standard error of the mean (SEM) and the level of significance (P). All calculations were made with STATISTICA 10 software.

The results of the sow reproductive performance are presented in Table 44 and Table 45.

TABLE 44

Table 44. Sow performance

| | Groups | | | | SEM | P |
|---|---|---|---|---|---|---|
| | 1 | 2 | 3 | 4 | | |
| Sows, n | 13 | 13 | 13 | 13 | | |
| primiparous | 1 | 1 | 1 | 1 | | |
| multiparous | 12 | 12 | 12 | 12 | | |
| Average sow parity | 3.23 | 3.85 | 3.46 | 3.50 | 0.183 | 0.690 |

TABLE 44-continued

Table 44. Sow performance

| | Groups | | | | SEM | P |
|---|---|---|---|---|---|---|
| | 1 | 2 | 3 | 4 | | |
| Sows not pregnant after 1 matings, n | 5 | 3 | 2 | 2 | — | — |
| Sows not pregnant after 2 matings, n | 3 | 2 | 2 | 2 | — | — |
| Farrowing rate (%) | 76.92 | 84.62 | 84.62 | 84.62 | 5.143 | 0.999 |
| Culled sows, n reproductive failure | 3 | 2 | 2 | 2 | | |
| Subsequent performance | 3 | 2 | 2 | 2 | | |
| Weaning-to-estrus interval, d | 5.40 | 5.09 | 5.64 | 5.00 | 0.102 | 0.093 |
| Wean-to-remate interval, d | 14.86 | 9.89 | 7.70 | 5.10 | 1.373 | 0.100 |
| Farrowing rate (%) | 70.00 | 80.00 | 90.91 | 90.91 | 5.820 | 0.544 |

TABLE 45

Table 45. Litter performance

| | Groups | | | | SEM | P |
|---|---|---|---|---|---|---|
| | 1 | 2 | 3 | 4 | | |
| Lactation length, d | 28.00 | 28.00 | 28.00 | 28.00 | | |
| Litter response criteria 1$^{st}$ day Number of piglets per litter | | | | | | |
| Born alive | 11.50 | 12.82 | 13.18 | 13.00 | 0.308 | 0.224 |
| Weak | 0.80 | 0.36 | 0.40 | 0.45 | 0.104 | 0.450 |
| Stillborn | 1.70 | 1.36 | 1.09 | 1.27 | 0.173 | 0.677 |
| Mummies | 0.20 | 0.18 | 0.20 | 0 | 0.055 | 0.500 |
| Litter weight, kg | 15.59$^b$ | 18.50$^a$ | 19.07$^a$ | 19.34$^a$ | 0.522 | 0.037 |
| Piglet weight, kg | 1.36 | 1.44 | 1.45 | 1.49 | 0.023 | 0.223 |
| Weaning Number of piglets per litter | 9.80 | 11.73 | 11.82 | 11.55 | 0.173 | 0.055 |
| Litter weight, kg | 67.85$^b$ | 83.96$^b$ | 84.33$^b$ | 85.98$^b$ | 2.329 | 0.014 |
| Piglet weight, kg | 6.94 | 7.16 | 7.31 | 7.48 | 0.152 | 0.657 |
| Mortality, % | 13.25 | 8.37 | 10.64 | 11.06 | 0.852 | 0.261 |

$^{a,b}$p < 0.05

As shown in TABLES 44 and 45, the average parities of the treatment and control sows were 3.85, 3.46, 3.50 and 3.23, respectively. The sows received diets with the vitamin E or with vitamin E and PROVIOX 50 addition were characterised by better fertility and mating effectiveness compared to the negative control group sows (number sows not pregnant after first and second matings, farrowing rate). The differences observed were, however, not statistically significant. In this experiment, polyphenols product (PROVIOX 50) supplementation had no significant effect on number of culled sows, but showed a tendency to shorter wean-remating interval. Addition of the different level of vitamin E and PROVIOX 50 to sows diet improved farrowing rate in the next cycle, but the differences between groups were statistically not significant. Considering the results it can be concluded that the sows received diets with the PROVIOX 50 supplement were characterised by similar fertility and mating effectiveness compared to the group sows fed diets with vitamin E.

There were no differences (P<0.05) in total number of pigs born alive, weak or born mummified (Table 45). Depending on the treatments, the average number of piglets born alive of the analysed sows varied between 11.50 and 13.18, and the average number of weak piglets ranged from 0.36 to 0.8. Experimental groups had higher number born alive piglets per litter (12.82, 13.18, 13.00) than the control (11.50). The differences observed were, not statistically significant (P<0.05). The mean number of mummies varied between 0 and 0.2. Number weaned piglets per litter tended to be higher (P=0.06) in sows fed diets with vitamin E and PROVIOX 50 supplementation (11.73, 11.82, 11.55 vs. 9.80). Experimental groups had significantly (P<0.05) higher litter weight (18.50, 19.07, 19.34 kg) than the control (15.59 kg). The piglets weight at birth in the experimental group reached 1.44 (group 2), 1.45 (group 3), and 1.49 (group 4), respectively, whereas that of the control animals (group 1) was 1.46 kg, on average. The differences observed were, not statistically significant (P<0.05). Groups with vitamin E and PROVIOX 50 addition had significantly (P<0.05) higher litter weight at weaning (85.05, 84.33, 85.98 kg) than the control (67.85 kg). After lactation period, the final body weight of piglets from treatments 2, 3 and 4 reached 7.16, 7.31 and 7.48 kg, respectively, whereas the animals from the control group (1) weighed 6.94 kg, on average. The differences in weaning weight between groups were statistically not significant. The application of the vitamin E and PROVIOX 50 in diets for sows decrease mortality of the experimental piglets, but the differences between groups were statistically not significant. The three leading causes of death were: weak, crushing by the sow and dehydratation.

Considering the results it can be concluded that the sows received diets with the PROVIOX 50 supplement were characterised by similar fertility, mating effectiveness and litter performance compared to the group sows fed diets with vitamin E addition.

At each measurement period during gestation and lactation serum a-tocopherol (vitamin E) concentrations were higher (P<0.001) when vitamin E was added to the sow diets. As the supplemental vitamin E level increased, the serum α-tocopherol concentrations increased (Table 46). Although an increase in serum vitamin E was demonstrated in both periods (farrowing and weaning) results demonstrated a greater increase at farrowing than later. (In the group IV (vitamin E 50/75 mg/kg+PROVIOX 50) the serum a-tocopherol concentrations at farrowing and at weaning were similar to the group III (vit. E 100/150 mg/kg). There was a decline in serum a-tocopherol from breeding to farrowing, but only in the group 1 and 2. When the basal diet was fed, serum vitamin A (retinol) concentrations declined from breeding to farrowing. When supplemental vitamin E was provided, there was a linear (P<0.001) increase in serum vitamin A concentrations at farrowing. Compared with pigs fed 50/75 mg vitamin E/kg diet (group 2) the pigs fed the diet 3 (100/150 mg vit. E/kg) and 4 (vit. E+PROVIOX 50) had higher serum concentrations of vitamin A. Diet supplementation with vitamin E and PROVIOX 50 had positive effect (P<0.05) on the levels vitamin A in the serum of the sows. Vitamin E had no effect on serum vitamin A concentration at weaning.

Various analyses were conducted to evaluate the antioxidative effect of dietary vitamin E and PROVIOX 50 as shown in TABLE 46.

TABLE 46

Table 46. The content of vitamins E and A (pg/ml) in the serum of sows

| Specification | Groups | | | | SEM | P |
|---|---|---|---|---|---|---|
| | 1 | 2 | 3 | 4 | | |
| Vitamin E | | | | | — | — |
| Breeding | 1.04 | 1.09 | 1.11 | 1.06 | 0.012 | 0.106 |
| Farrowing | $0.42^C$ | $0.74^B$ | $1.16^A$ | $1.14^A$ | 0.050 | <0.001 |
| Weaning | $0.75^C$ | $1.02^B$ | $1.13^A$ | $1.06^{AB}$ | 0.026 | <0.001 |
| Vitamin A | | | | | | |
| Breeding | 0.14 | 0.15 | 0.16 | 0.16 | 0.003 | 0.100 |
| Farrowing | $0.07^C$ | $0.11^B$ | $0.15^{Ab}$ | $0.17^{Aa}$ | 0.007 | <0.001 |
| Weaning | 0.16 | 0.15 | 0.15 | 0.16 | 0.002 | 0.091 |

$^{a,b}p < 0.05$
$^{A,B}p < 0.01$

Serum total antioxidant status (TAS) has been used as an indication of animal antioxidant status. Addition of the different level of vitamin E and PROVIOX 50 modify the TAS. For TAS, there were differences between control (0 vit. E) and experimental groups. Serum TAS increased more in sows fed vitamin E with PROVIOX 50 than in sows fed only vitamin E. Serum SOD (superoxide dismutase) values ranged from 70.99 to 73.28 enzyme units (U/ml) at breeding. Serum SOD activities were influenced by dietary vitamin E level at farrowing and weaning (P<0.001). Highest activities of SOD were observed in sows fed vitamin E and PROVIOX 50, especially at weaning (P<0.001). GPx (glutathione peroxidase) activity in the blood from sows in the control group was significantly lower (P<0.001) than from sows receiving vitamin E. The highest activities of GPx were observed in sows fed vitamin E and PROVIOX 50 in both periods (farrowing and weaning) (P<0.001).

Piglets serum α-tocopherol concentration at 21 d of age was influenced by both antioxidant source (vitamin E and PROVIOX 50) and vitamin E level fed to the reproducing female (see TABLE 47 & 48).

TABLE 47

Table 47. The total antioxidant status (TAS mmol/L serum), the activity of superoxide dismutase (SOD U/ml of serum) and glutathione peroxidase (GPx U/ml of blood) in the serum and blood of sows

| Specification | Groups | | | | SEM | P |
|---|---|---|---|---|---|---|
| | 1 | 2 | 3 | 4 | | |
| TAS | | | | | — | — |
| Breeding | 1.27 | 1.26 | 1.29 | 1.29 | 0.007 | 0.304 |
| Farrowing | $1.14^{Bb}$ | $1.18^a$ | $1.19^a$ | $1.20^A$ | 0.007 | 0.007 |
| Weaning | $1.16^{Bb}$ | $1.18^B$ | $1.20^{Ba}$ | $1.29^A$ | 0.010 | <0.001 |
| SOD | | | | | | |
| Breeding | 70.99 | 71.43 | 73.28 | 71.53 | 0.676 | 0.610 |
| Farrowing | $61.13^C$ | $77.14^B$ | $79.60^{AB}$ | $82.82^A$ | 1.458 | <0.001 |
| Weaning | $61.88^D$ | $79.50^C$ | $90.93^B$ | $140.27^A$ | 4.715 | <0.001 |
| GPx | | | | | | |
| Breeding | 37.24 | 37.73 | 38.85 | 38.92 | 0.271 | 0.059 |
| Farrowing | $27.00^D$ | $32.77^C$ | $37.64^B$ | $40.11^A$ | 0.835 | <0.001 |
| Weaning | $27.23^D$ | $34.78^C$ | $36.48^B$ | $40.27^A$ | 0.766 | <0.001 |

TABLE 48

Vitamin E and A (mg/ml serum), total antioxidant status (TAS mmol/L serum), the activity of superoxide dismutase (SOD U/ml of serum) and glutathione peroxidase (GPx U/ml of blood) in the serum and in blood piglets at 21 days

| Specification | Groups | | | | SEM | P |
|---|---|---|---|---|---|---|
| | 1 | 2 | 3 | 4 | | |
| Vitamin E | $0.52^D$ | $1.41^C$ | $1.61^A$ | $1.48^B$ | 0.070 | <0.001 |
| Vitamin A | $0.078^D$ | $0.16^C$ | $0.20^B$ | $0.25^A$ | 0.011 | <0.001 |
| TAS | $0.86^C$ | $1.16^B$ | $1.18^{AB}$ | $1.24^A$ | 0.026 | <0.00 |
| SOD | $98.01^B$ | $100.61^B$ | $129.54^{Ab}$ | $134.80^{Aa}$ | 2.743 | <0.00 |
| GPx | $27.40^C$ | $29.12^B$ | $29.91^B$ | $34.58^A$ | 0.457 | <0.001 |

$^{a,b}P \leq 0.05$;
$^{A,B}P \leq 0.01$

The addition of vitamin E to the diets of sows resulted in increased (P<0.001) serum a-tocopherol concentrations. When lactation sows were fed 150 mg/kg of vitamin E, their piglets had higher (P<0.001) serum a-tocopherol concentrations than piglets from sows fed 75 mg/kg vitamin E. Piglets from sows fed PROVIOX 50 had higher (P<0.001) serum a-tocopherol concentrations at 21 d than pigs nursing sows fed vit. E 75 mg/kg. Serum retinol (vitamin A) concentrations increased (P<0.001) as the dietary level of vitamin E in sows diets increased. The highest concentrations of serum vitamin A were observed in piglets from sows fed vitamin E and PROVIOX 50 (P<0.001).

Addition of the different level of vitamin E and PROVIOX 50 modify the TAS. For TAS, there were difference between control and experimental groups (P<0.001). Mean serum TAS concentrations were higher in vitamin E supplemented groups compared to non-supplemented groups. Serum SOD activities were highest in piglets of vitamin E and PROVIOX 50 supplemented sows compared to piglets from only vitamin E supplemented sows. GPx (glutathione peroxidase) activity in the blood from piglets in the control group was significantly lower (P<0.001) than from piglets from sows receiving vitamin E. When lactation sows were fed 75 mg/kg of vitamin E and PROVIOX 50, their piglets had higher (P<0.001) blood GPx activity than piglets from sows fed 75 or 150 mg vitamin. E/kg diet.

Considering the results it can be concluded that the sows received diets with the PROVIOX 50 supplement were characterised by similar or better vitamin E status and better antioxidant status compared to the group sows fed diets only with vitamin E addition. It is concluded that PROVIOX 50 can replace 50% of vitamin E with the same (performance) or better (antioxidant status) effect.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

What is claimed is:

1. A method of improving performance in an avian animal, the method comprising:
   feeding to the avian animal as a part of its feed ration a composition comprising:
   vitamin E; and
   a polyphenol source;
   wherein the vitamin E is present in the feed ration at an inclusion level of about 10 ppm to about 200 ppm and the ratio of the vitamin E inclusion level to an inclusion level of the polyphenol source in the composition is about 1:1 vitamin E to polyphenol source,
   collecting a fertilized egg produced by the avian animal about 8 weeks alter the start of feeding of the composition to the avian animal;
   incubating the fertilized egg until it hatches to provide the offspring; and
   growing out the offspring,
   wherein performance is improved compared to an avian animal fed a feed ration not containing the composition.

2. The method of claim 1, wherein the avian animal is selected from the group consisting of a chicken, a turkey, a duck, a goose, and combinations thereof.

3. The method of claim 1, wherein the vitamin E is present in the feed ration at an inclusion level of about 20 ppm to about 100 ppm.

4. The method of claim 1, wherein the ratio of the vitamin E inclusion level to an inclusion level of the polyphenol source in the composition is in the range from 1:2 to 1:5 vitamin E to polyphenol source.

5. The method of claim 1, wherein the polyphenol source comprises at least one of onion extract, gape seed extract, and rosemary extract.

6. The method of claim 1, wherein feeding of the composition to the avian animal begins when the avian animal is hatched.

7. The method of claim 1, wherein the collecting a fertilized egg produced by the avian animal is about 8 weeks after the start of feed of the composition.

8. The method of claim 1, wherein the performance is improved performance in offspring or breeder performance and wherein the improved offspring performance is at least one of improved offspring weight at hatch, improved offspring final bodyweight, improved offspring average daily gain, improved offspring feed conversion ratio, and improved offspring feed intake and antioxidant status.

9. The method of claim 1, wherein the performance is improved performance in breeder performance and wherein the improved breeder performance is at least one of improved hatchability or reduction in number of egg shells breaking.

10. A method of improving porcine animal productivity comprising:
  feeding to the porcine animal as a part of its feed ration a composition comprising:
    vitamin E; and
    a polyphenol source;
  wherein the vitamin E is present in the feed ration at an inclusion level of about 1 ppm to about 300 ppm and the ratio of the vitamin E inclusion level to an inclusion level of the polyphenol source in the composition is about 1:1 vitamin E to polyphenol source.

11. The method of claim 10, wherein the porcine animal productivity comprises reproductive performance, litter performance and antioxidant status.

12. The method of claim 11, wherein antioxidant status is superoxide dismutase, glutathione peroxidase and vitamin A and vitamin E.

13. The method of claim 10, wherein the porcine animal is a feeder pig, breeding pig, piglets, sows, gilts, barrows and boars.

14. The method of claim 10, wherein the animal is fed during gestation, lactation, breeding or before breeding.

15. The method of claim 10, wherein the polyphenol source comprises at least one of onion extract, grape seed extract, and rosemary extract.

16. The method of claim 10, wherein the ratio of the vitamin E inclusion level to an inclusion level of the polyphenol source in the composition is at least 1:1 vitamin E to polyphenol source.

17. The method of claim 10, wherein the ratio of the vitamin E inclusion level to an inclusion level of the polyphenol source in the composition is in the range from 1:2 to 1:5 vitamin E to polyphenol source.

* * * * *